US008871709B2

(12) United States Patent
Upton et al.

(10) Patent No.: US 8,871,709 B2
(45) Date of Patent: Oct. 28, 2014

(54) SYNTHETIC CHIMERIC PROTEINS COMPRISING EPIDERMAL GROWTH FACTOR AND VITRONECTIN

(75) Inventors: Zee Upton, Indooroopilly (AU); Christopher Luke Towne, Tingalpa (AU)

(73) Assignee: Queensland University of Technolgy, Brisbane, Queensland (AU)

( * ) Notice: Subject to any disclaimer, the term of this patent is extended or adjusted under 35 U.S.C. 154(b) by 811 days.

(21) Appl. No.: 12/793,386

(22) Filed: Jun. 3, 2010

(65) Prior Publication Data
US 2010/0303884 A1 Dec. 2, 2010

Related U.S. Application Data

(63) Continuation-in-part of application No. 12/627,647, filed on Nov. 30, 2009, which is a continuation-in-part of application No. 10/544,796, filed as application No. PCT/AU2004/000117 on Feb. 5, 2004, now Pat. No. 7,659,367.

(30) Foreign Application Priority Data

Feb. 5, 2003 (AU) ............................... 2003900481

(51) Int. Cl.
| A61K 38/18 | (2006.01) |
| C07K 14/00 | (2006.01) |
| C07K 16/28 | (2006.01) |
| C07K 14/475 | (2006.01) |
| C07K 14/435 | (2006.01) |
| C07K 14/50 | (2006.01) |
| A61K 38/00 | (2006.01) |

(52) U.S. Cl.
CPC .............. *C07K 14/50* (2013.01); *C07K 16/2839* (2013.01); *C07K 14/475* (2013.01); *C07K 2319/00* (2013.01); *A61K 38/00* (2013.01); *C07K 14/435* (2013.01); *C07K 2317/76* (2013.01); *C07K 2319/50* (2013.01)
USPC ............... 514/7.6; 514/9.1; 514/9.4; 514/9.6; 530/350

(58) Field of Classification Search
None
See application file for complete search history.

(56) References Cited

U.S. PATENT DOCUMENTS
7,514,398 B2    4/2009   Upton et al.

FOREIGN PATENT DOCUMENTS
| AU | WO 99/54359 | * 4/1999 | ............. C07K 19/00 |
| WO | WO-00/55206 A1 | 9/2000 | |
| WO | WO-02/24219 A1 | 3/2002 | |

OTHER PUBLICATIONS

Nandagopal et al., Protein Engineering, 1996; 9: 781-788.*
Vogel et al., JCB, 1993; 121: 461-468.*
Cloning Vector Map downloaded on Nov. 30, 2012 from the QIAGEN website (2 pages total).*
Phillips, A., J Pharm Pharmacology 53: 1169-1174, 2001.*
van de Poll et al., JBC, 1998; 273: 16075-16081.*
Souriau et al., Biol. Chem., 1998; 380: 451-458.*
Zhao et al., Biochem Biophys Res Comm, 1993; 192: 575-582.*
Cherny et al., JBC, 1993; 268: 9725-9729.*
The website downloaded on Jul. 18, 2013 showing human Vn Hbd domain; from kerafast.com/p-779-human-vitronectin-n-gstheparin-binding-domain.aspx: 2 pp. total.*
Sharma et al., The EMBO Journal, 1999; 18: 1468-1479.*
Kawase et al., FEBS Letters, 1992; 298: 126-128.*
Kornblihtt et al., EMBO Journal, 1985; 4: 1755-1759.*
Schultz et al., Acta Opthalmologica, 1992; 70: 60-66.*
Bell et al., Nucleic Acids Research, 1986; 14: 8427-8446.*
Suzuki et al., The EMBO journal, 1985; 4: 2519-2524.*
Uhlén and Moks, Methods Enzymol. 1990; 185: 129-43.*
Huston et al., Methods in Enzymology, 1991; 203: 46-88.*
Vella et al., J. Peptide Res, 1999; 415-426.*
Schoppet et al., Lab Invest. 2002; 82: 37-46.*
Chillakuri et al., FEBS Letters, 2010; 584: 3287-3291.*
Eatock et al., "Tumour Vasculature as a Target for Anticancer Therapy", *Cancer Treatment Reviews* 26:191-204 (2000).
Gui et al., "Insulin-Like Growth Factor (IGF)-Binding Protein-3 (IGFBP-3) Binds to Fibronectin (FN): Demonstration of IGF-I/IGFBP-3/FN Ternary Complexes in Human Plasma", *The Journal of Clinical Endocrinol. Metab.*, 86:2104-2110 (2001).
Jones et al., "Cell Migration: Interactions Among Integrins, IGFs and IGFBPs", *Progress in Growth Factor Research*, 6:319.327 (1995).
Jones et al., "Ligand Occupancy of the αVβ3 Integrin is Necessary for Smooth Muscle Cells to Migrate in Response to Insulin-Like Growth Factor I", *Proc. Natl. Acad. Sci. USA*, 93:2482-2487 (1996).
Klemke, et al., "Receptor Tyrosine Kinase Signaling Required for Integrin αvβ5-Directed Cell Motility but Not Adhesion on Vitronectin", *The Journal of Cell Biology*, 127:859-866 (1994).

(Continued)

*Primary Examiner* — Christina Borgeest
(74) *Attorney, Agent, or Firm* — Tarolli, Sundheim, Covell & Tummino LLP

(57) ABSTRACT

Isolated protein complexes are provided comprising growth factors such as IGF-I, IGF-II, EGF, bFGF, KGF, VEGF or PDGF, or at least domains thereof that enable binding to and activation of both a growth factor receptor, and an integrin receptor-binding domain of vitronectin or fibronectin. These protein complexes may be in the form of oligo-protein complexes or single, synthetic proteins where the growth factor and vitronectin or fibronectin sequences are joined by a linker sequence. In particular forms, vitronectin or fibronectin sequences do not include a heparin binding domain and/or polyanionic domain. Also provided are uses of these protein complexes for stimulating or inducing cell migration and/or proliferation which may have use in wound healing, tissue engineering, cosmetic and therapeutic treatments such as skin replacement and skin replenishment and treatment of burns where epithelial cell migration is required. In other embodiments, the invention provides inhibition of cancer cell metastasis, particularly in relation to breast cancer.

26 Claims, 25 Drawing Sheets

(56) References Cited

OTHER PUBLICATIONS

Kricker et al., "Structural and Functional Evidence for the Interaction of Insulin-Like Growth Factors (IGFs) and IGF Binding Proteins with Vitronectin", *Endocrinology*, 144:2807-2815 (2003).

Maile et al., "The Heparin Binding Domain of Vitronectin is the Region that is Required to Enhance Insulin-Like Growth Factor-I Signaling", *Molecular Endocrinology*, 20:881-892 (2006).

Murphy et al., "Purified Yolk Vitronectin Forms Complexes with IGFs and IGFBPs that Enhance Cell Migration and Growth", *Growth Hormone & IGF Research*, 14:166; Abstract #209 (2004).

Nagano et al., "Yolk Vitronectine Purification and Differences from its Blood Homologue in Molecular Size, Heparin, Binding, Collagen Binding and Bound Carbohydrate", *The Journal of Biological Chemistry*, 267:24863-24870 (1992).

Noble et al., "Insulin-Like Growth Factor-II Bound to Vitronectin Enhances MCF-7 Breast Cancer Cell Migration", *Endocrinology*, 144:2417-2424 (2003).

Schvartz et al., "Vitronectin", *The International Journal of Biochemistry & Cell Biology*, 31:539-544 (1999).

Upton et al., Indentification of Vitronectin as a Novel Insulin-Like Growth Factor-II Binding Protein, *Endocrinology*, 140:2928-2931 (1999).

Upton et al., "Vitronectin: Growth Factor Complexes Hold Potential as a Wound Therapy Approach", *Journal of Investigative Dermatology*, 128:1535-1544 (2008).

Van Lonkhuyzen et al., "Chimeric Vitronectin: Insulin-Like Growth Factor Proteins Enhance Cell Growth and MIgraiton Through Co-Activation of Receptors", *Growth Factors*, 25:295-308 (2007).

Xu et al., "Model for the Three-Dimensional Structure of Vitronectin: Predictions for the Multi-Domain Protein from Threading and Docking", *Proteins: Structure, Function, and Genetics*, 44:312-320 (2001).

Xu et al., "Fibronectin Binds Insulin-Like Growth Factor-Binding Protein 5 and Abolishes its Ligand-Dependent Action on Cell Migration", *The Journal of Biological Chemistry*, 279:4269-4277 (2004).

\* cited by examiner

Amino acid sequence of full length vitronectin (including signal peptide)

```
  1  maplrpllil  allawvalad  qesckgrcte  gfnvdkkcqc  delcsyyqsc  ctdytaeckp
 61  cvtrgdvftm  pedeytvydd  geeknnatvh  eqvggpslts  dlqagskgnp  eqtpvlkpee
121  eapapevgas  kpegidsrpe  tlhpgrpqpp  aeeelcsgkp  fdaftdlkng  slfafrgqyc
181  yeldekavrp  gypklirdvw  giegpidaaf  trincqgkty  lfkgsqywrf  edgvldpdyp
241  rnisdgfdgi  pdnvdaalal  pahsyegrer  vyffkgkqyw  eyqfqhqpsq  eecegsslsa
301  vfehfammqr  dswedifell  fwgrtsagtr  qpqfisrdwh  gvpgqvdaam  agriyisgma
361  prpslakkqr  frhrnrkgyr  sqrghsrgrn  qnsrrpsram  wlslfssees  nlgannyddy
421  rmdwlvpatc  epiqsvfffs  gdkyyrvnlr  trrvdtvdpp  yprsiaqywl  gcpapghl
```

| Domain Structure | Residues[1] | Residues[2] |
|---|---|---|
| Signal Peptide |  | 1-19 |
| Somatomedin B domain | 1-44 | 20-63 |
| RGD Motif | 45-47 | 64-66 |
| Polyanionic (acidic) region | 53-64 | 72-83 |
| Hemopexin-like repeats (x2) | 131-459 | 150-478 |
| - Central 4-bladed propeller domain | 131-342 | 150-361 |
| - C-terminal heparin binding domain | 347-459 | 366-478 |
| Polycationic (basic) region | 348-379 | 367-398 |

| Residue Modification Sites | Residues[1] | Residues[2] |
|---|---|---|
| cAMP-dependant PK phosphorylation site | 378 | 397 |
| Sulphated tyrosine residues (x2) | 56, 59 | 75, 78 |
| PKC phosphorylation site | 362 | 381 |
| Casein kinase phosphorylation site (x2) | 50, 57 | 69, 76 |

| Protease Recognition Sites | Residues[1] | Residues[2] |
|---|---|---|
| Endogenous cleavage site (unidentified protease) | 379-380 | 398-399 |
| Thrombin cleavage site | 305-306 | 324-325 |
| Thrombin cleavage site | 370-371 | 389-390 |
| Elastase cleavage site | 330-331 | 349-350 |
| Elastase cleavage site | 383-384 | 402-403 |
| Plasmin cleavage site | 361-362 | 380-381 |

| Substrate Binding Sites | Residues[1] | Residues[2] |
|---|---|---|
| PAI-1 |  | 12-30 |
| PAI-1 |  | 348-370 |
| uPAR |  | SomB region |
| Integrin |  | 45-47 |
| Collagen |  | Polycationic region |
| Collagen |  | Polyanionic region |
| Thrombin antithrombin III complex |  | Polycationic region |
| Plasminogen |  | 332-348 |
| Glycosaminoglycan |  | 348-361 |

[1] Residues numbered according to their position on the mature protein
[2] Residues numbered according to their position on the pro-protein (with signal peptide)

FIGURE 7

A) VN AA sequence

```
dqesckgrct egfnvdkkcq cdelcsyyqs cctdytaeck pqvtrgdvft mpedeytvyd
dgeeknnatv heqvggpslt sdlqaqskgn peqtpvlkpe eeapapevga skpegidsrp
etlhpgrpqp paeeelcsgk pfdaftdlkn gslfafrgqy cyeldekavr pgypklirdv
wgiegpidaa ftrincqgkt ylfkgsqywr fedgvldpdy prnisdgfdg ipdnvdaala
lpahsysgre rvyffkgkqy weyqfqhqps qeecegssls avfehfammq rdswedifel
lfwgrtsagt rqpqfisrdw hgvpgqvdaa magriyisgm aprpslakkq rfrhrnrkgy
rsqrghsrgr nqnsrrpsra twlslfssee snlgannydd yrmdwlvpat cepiqsvfff
sgdkyyrvnl rtrrvdtvdp pyprsiaqyw lgcpapghl
```

B) IGF-I AA sequence

```
gpetlcgael vdalqfvcgd rgfyfnkptg ygsssrrapq tgivdeccfr scdlrrlemy
caplkpaksa
```

C) Linker Sequences

1) Gly$_4$ Ser

2) Gly$_4$ Ser$_3$ 3) (Gly$_4$ Ser)$_3$

4) Leu Ile Lys Met Lys Pro    Plasmin Cleavage Recognition Site
   Ref: FASEB (2001) 15: 1300-2

5) Gln Pro Gln Gly Leu Ala Lys    Collagenase-3 Cleavage Recognition Site
   Ref: Biomacromolecules (2003) 4: 1214-23

FIGURE 13

A) VN (1...459) IGF-I (1...70)

```
dqesckgrct  egfnvdkkcq  cdelcsyyqs  cctdytaeck  pqvtrgdvft  mpedeytvyd
dgeeknnatv  heqvggpslt  sdlqaqskgn  peqtpvlkpe  eeapapevga  skpegidsrp
etlhpgrpqp  paeeelcsgk  pfdaftdlkn  gslfafrgqy  cyeldekavr  pgypklirdv
wgiegpidaa  ftrincqgkt  ylfkgsqywr  fedgvldpdy  prnisdgfdg  ipdnvdaala
lpahsysgre  rvyffkgkqy  weyqfqhqps  qeecegssls  avfehfammq  rdswedifel
lfwgrtsagt  rqpqfisrdw  hgvpgqvdaa  magriyisgm  aprpslakkq  rfrhrnrkgy
rsqrghsrgr  nqnsrrpsra  twlslfssee  snlgannydd  yrmdwlvpat  cepiqsvfff
sgdkyyrvnl  rtrrvdtvdp  pyprsiaqyw  lgcpapghl   -- LINK --  gpetlcgael
vdalqfvcgd  rgfyfnkptg  ygsssrrapq  tgivdeccfr  scdlrrlemy  caplkpaksa
```

B) VN (1...379) IGF-I (1...70)

```
dqesckgrct  egfnvdkkcq  cdelcsyyqs  cctdytaeck  pqvtrgdvft  mpedeytvyd
dgeeknnatv  heqvggpslt  sdlqaqskgn  peqtpvlkpe  eeapapevga  skpegidsrp
etlhpgrpqp  paeeelcsgk  pfdaftdlkn  gslfafrgqy  cyeldekavr  pgypklirdv
wgiegpidaa  ftrincqgkt  ylfkgsqywr  fedgvldpdy  prnisdgfdg  ipdnvdaala
lpahsysgre  rvyffkgkqy  weyqfqhqps  qeecegssls  avfehfammq  rdswedifel
lfwgrtsagt  rqpqfisrdw  hgvpgqvdaa  magriyisgm  aprpslakkq  rfrhrnrkgy
rsqrghsrgr  nqnsrrpsr   -- LINK --  gpetlcgael  vdalqfvcgd  rgfyfnkptg
ygsssrrapq  tgivdeccfr  scdlrrlemy  caplkpaksa
```

C) VN (1...52) IGF-I (1...70)

```
dqesckgrct  egfnvdkkcq  cdelcsyyqs  cctdytaeck  pqvtrgdvft  mp
-- LINK --  gpetlcgael  vdalqfvcgd  rgfyfnkptg  ygsssrrapq  tgivdeccfr
scdlrrlemy  caplkpaksa
```

D) VN (1...130) IGF-I (1...70)

```
dqesckgrct  egfnvdkkcq  cdelcsyyqs  cctdytaeck  pqvtrgdvft  mpedeytvyd
dgeeknnatv  heqvggpslt  sdlqaqskgn  peqtpvlkpe  eeapapevga  skpegidsrp
etlhpgrpqp  -- LINK --  gpetlcgael  vdalqfvcgd  rgfyfnkptg  ygsssrrapq
tgivdeccfr  scdlrrlemy  caplkpaksa
```

E) VN (1...130, 347...459) IGF-I (1...70)

```
dqesckgrct  egfnvdkkcq  cdelcsyyqs  cctdytaeck  pqvtrgdvft  mpedeytvyd
dgeeknnatv  heqvggpslt  sdlqaqskgn  peqtpvlkpe  eeapapevga  skpegidsrp
etlhpgrpqp  ammqrdswed  ifellfwgrt  sagtrqpqfi  srdwhgvpgq  vdaamagriy
isgmaprpsl  akkqrfrhrn  rkgyrsqrgh  srgrnqnsrr  psratwlslf  sseesnlgan
nyddyrmdwl  vpatcepiqs  vfffsgdkyy  rvnlrtrrvd  tvdppyprsi  aqywlgcpap
ghl         -- LINK --  gpetlcgael  vdalqfvcgd  rgfyfnkptg  ygsssrrapq
tgivdeccfr  scdlrrlemy  caplkpaksa
```

FIGURE 14A

F) VN (1...130, 347..379) IGF-I (1...70)

```
dqesckgrct  egfnvdkkcq  cdelcsyyqs  cctdytaeck  pqvtrgdvft  mpedeytvyd
dgeeknnatv  heqvggpslt  sdlqaqskgn  peqtpvlkpe  eeapapevga  skpegidsrp
etlhpgrpqp  ammqrdswed  ifellfwgrt  sagtrqpqfi  -- LINK --  gpetlcgael
vdalqfvcgd  rgfyfnkptg  ygsssrrapq  tgivdeccfr  scdlrrlemy  caplkpaksa
```

G) VN (1...346) IGF-I (1...70)

```
dqesckgrct  egfnvdkkcq  cdelcsyyqs  cctdytaeck  pqvtrgdvft  mpedeytvyd
dgeeknnatv  heqvggpslt  sdlqaqskgn  peqtpvlkpe  eeapapevga  skpegidsrp
etlhpgrpqp  paeeelcsgk  pfdaftdlkn  gslfafrgqy  cyeldekavr  pgypklirdv
wgiegpidaa  ftrincqgkt  ylfkgsqywr  fedgvldpdy  prnisdgfdg  ipdnvdaala
lpahsysgre  rvyffkgkqy  weyqfqhqps  qeecegssls  avfehfammq  rdswedifel
lfwgrtsagt  rqpqfisrdw  hgvpgqvdaa  magriyisgm  aprpsla     -- LINK --
gpetlcgael  vdalqfvcgd  rgfyfnkptg  ygsssrrapq  tgivdeccfr  scdlrrlemy
caplkpaksa
```

H) VN (T50A, T57A) IGF-I (1...70)

```
dqesckgrct  egfnvdkkcq  cdelcsyyqs  cctdytaeck  pqvtrgdvfA  mpedeyAvyd
dgeeknnatv  heqvggpslt  sdlqaqskgn  peqtpvlkpe  eeapapevga  skpegidsrp
etlhpgrpqp  paeeelcsgk  pfdaftdlkn  gslfafrgqy  cyeldekavr  pgypklirdv
wgiegpidaa  ftrincqgkt  ylfkgsqywr  fedgvldpdy  prnisdgfdg  ipdnvdaala
lpahsysgre  rvyffkgkqy  weyqfqhqps  qeecegssls  avfehfammq  rdswedifel
lfwgrtsagt  rqpqfisrdw  hgvpgqvdaa  magriyisgm  aprpslakkq  rfrhrnrkgy
rsqrghsrgr  nqnsrrpsra  twlslfssee  snlgannydd  yrmdwlvpat  cepiqsvfff
sgdkyyrvnl  rtrrvdtvdp  pyprsiaqyw  lgcpapghl   -- LINK --  gpetlcgael
vdalqfvcgd  rgfyfnkptg  ygsssrrapq  tgivdeccfr  scdlrrlemy  caplkpaksa
```

I) VN (T50E, T57E) IGF-I (1...70)

```
dqesckgrct  egfnvdkkcq  cdelcsyyqs  cctdytaeck  pqvtrgdvfE  mpedeyEvyd
dgeeknnatv  heqvggpslt  sdlqaqskgn  peqtpvlkpe  eeapapevga  skpegidsrp
etlhpgrpqp  paeeelcsgk  pfdaftdlkn  gslfafrgqy  cyeldekavr  pgypklirdv
wgiegpidaa  ftrincqgkt  ylfkgsqywr  fedgvldpdy  prnisdgfdg  ipdnvdaala
lpahsysgre  rvyffkgkqy  weyqfqhqps  qeecegssls  avfehfammq  rdswedifel
lfwgrtsagt  rqpqfisrdw  hgvpgqvdaa  magriyisgm  aprpslakkq  rfrhrnrkgy
rsqrghsrgr  nqnsrrpsra  twlslfssee  snlgannydd  yrmdwlvpat  cepiqsvfff
sgdkyyrvnl  rtrrvdtvdp  pyprsiaqyw  lgcpapghl   -- LINK --  gpetlcgael
vdalqfvcgd  rgfyfnkptg  ygsssrrapq  tgivdeccfr  scdlrrlemy  caplkpaksa
```

FIGURE 14B

J) VN (S378E) IGF-I (1...70)

```
dqesckgrct egfnvdkkcq cdelcsyyqs cctdytaeck pqvtrgdvft mpedeytvyd
dgeeknnatv heqvggpslt sdlqaqskgn peqtpvlkpe eeapapevga skpegidsrp
etlhpgrpqp paeeelcsgk pfdaftdlkn gslfafrgqy cyeldekavr pgypklirdv
wgiegpidaa ftrincqgkt ylfkgsqywr fedgvldpdy prnisdgfdg ipdnvdaala
lpahsysgre rvyffkgkqy weyqfqhqps qeecegssls avfehfammq rdswedifel
lfwgrtsagt rqpqfisrdw hgvpgqvdaa magriyisgm aprpslakkq rfrhrnrkgy
rsqrghsrgr nqnsrrpEra twlslfssee snlgannydd yrmdwlvpat cepiqsvfff
sgdkyyyrvnl rtrrvdtvdp pyprsiaqyw lgcpapghl  -- LINK --  gpetlcgael
vdalqfvcgd rgfyfnkptg ygsssrrapq tgivdeccfr scdlrrlemy caplkpaksa
```

K) VN (S378A) IGF-I (1...70)

```
dqesckgrct egfnvdkkcq cdelcsyyqs cctdytaeck pqvtrgdvft mpedeytvyd
dgeeknnatv heqvggpslt sdlqaqskgn peqtpvlkpe eeapapevga skpegidsrp
etlhpgrpqp paeeelcsgk pfdaftdlkn gslfafrgqy cyeldekavr pgypklirdv
wgiegpidaa ftrincqgkt ylfkgsqywr fedgvldpdy prnisdgfdg ipdnvdaala
lpahsysgre rvyffkgkqy weyqfqhqps qeecegssls avfehfammq rdswedifel
lfwgrtsagt rqpqfisrdw hgvpgqvdaa magriyisgm aprpslakkq rfrhrnrkgy
rsqrghsrgr nqnsrrpAra twlslfssee snlgannydd yrmdwlvpat cepiqsvfff
sgdkyyyrvnl rtrrvdtvdp pyprsiaqyw lgcpapghl  -- LINK --  gpetlcgael
vdalqfvcgd rgfyfnkptg ygsssrrapq tgivdeccfr scdlrrlemy caplkpaksa
```

L) VN (S362E) IGF-I (1...70)

```
dqesckgrct egfnvdkkcq cdelcsyyqs cctdytaeck pqvtrgdvft mpedeytvyd
dgeeknnatv heqvggpslt sdlqaqskgn peqtpvlkpe eeapapevga skpegidsrp
etlhpgrpqp paeeelcsgk pfdaftdlkn gslfafrgqy cyeldekavr pgypklirdv
wgiegpidaa ftrincqgkt ylfkgsqywr fedgvldpdy prnisdgfdg ipdnvdaala
lpahsysgre rvyffkgkqy weyqfqhqps qeecegssls avfehfammq rdswedifel
lfwgrtsagt rqpqfisrdw hgvpgqvdaa magriyisgm aprpslakkq rfrhrnrkgy
rEqrghsrgr nqnsrrpsra twlslfssee snlgannydd yrmdwlvpat cepiqsvfff
sgdkyyyrvnl rtrrvdtvdp pyprsiaqyw lgcpapghl  -- LINK --  gpetlcgael
vdalqfvcgd rgfyfnkptg ygsssrrapq tgivdeccfr scdlrrlemy caplkpaksa
```

M) VN (1...459) IGF-I (4...70)

```
dqesckgrct egfnvdkkcq cdelcsyyqs cctdytaeck pqvtrgdvft mpedeytvyd
dgeeknnatv heqvggpslt sdlqaqskgn peqtpvlkpe eeapapevga skpegidsrp
etlhpgrpqp paeeelcsgk pfdaftdlkn gslfafrgqy cyeldekavr pgypklirdv
wgiegpidaa ftrincqgkt ylfkgsqywr fedgvldpdy prnisdgfdg ipdnvdaala
lpahsysgre rvyffkgkqy weyqfqhqps qeecegssls avfehfammq rdswedifel
lfwgrtsagt rqpqfisrdw hgvpgqvdaa magriyisgm aprpslakkq rfrhrnrkgy
rsqrghsrgr nqnsrrpsra twlslfssee snlgannydd yrmdwlvpat cepiqsvfff
sgdkyyyrvnl rtrrvdtvdp pyprsiaqyw lgcpapghl  -- LINK --  tlcgaelvda
lqfvcgdrgf yfnkptgygs ssrrapqtgi vdeccfrscd lrrlemycap lkpaksa
```

FIGURE 14C

N) VN (1...52, 65...459) IGF-I (1...70)

```
dqesckgrct egfnvdkkcq cdelcsyyqs cctdytaeck pqvtrgdvft mpknnatvhe
qvggpsltsd lqaqskgnpe qtpvlkpeee apapevgask pegidsrpet lhpgrpqppa
eeelcsgkpf daftdlkngs lfafrgqycy eldekavrpg ypklirdvwg iegpidaaft
rincqgktyl fkgsqywrfe dgvldpdypr nisdgfdgip dnvdaalalp ahsysgrerv
yffkgkqywe yqfqhqpsqe ecegsslsav fehfammqrd swedifellf wgrtsagtrq
pqfisrdwhg vpgqvdaama griyisgmap rpslakkqrf rhnrkgyrs qrghsrgrnq
nsrrpsratw lslfsseesn lgannyddyr mdwlvpatce piqsvfffsg dkyyrvnlrt
rrvdtvdppy prsiaqywlg cpapghl    -- LINK -- gpetlcgael vdalqfvcgd
rgfyfnkptg ygsssrrapq tgivdeccfr scdlrrlemy caplkpaksa
```

FIGURE 14D

A) VN (1...459) PDGF (1...210)

```
dqesckgrct egfnvdkkcq cdelcsyyqs cctdytaeck pqvtrgdvft mpedeytvyd
dgeeknnatv heqvggpslt sdlqaqskgn peqtpvlkpe eeapapevga skpegidsrp
etlhpgrpqp paeeelcsgk pfdaftdlkn gslfafrgqy cyeldekavr pgypklirdv
wgiegpidaa ftrincqgkt ylfkgsqywr fedgvldpdy prnisdgfdg ipdnvdaala
lpahsysgre rvyffkgkqy weyqfqhqps qeecegssls avfehfammq rdswedifel
lfwgrtsagt rqpqfisrdw hgvpgqvdaa magriyisgm aprpslakkq rfrhrnrkgy
rsqrghsrgr nqnsrrpsra twlslfssee snlgannydd yrmdwlvpat cepiqsvfff
sgdkyyrvnl rtrrvdtvdp pyprsiaqyw lgcpapghl  -- LINK --
(PDGF Accession # P04085)
```

B) VN (1...459) VEGF (1...102)

```
dqesckgrct egfnvdkkcq cdelcsyyqs cctdytaeck pqvtrgdvft mpedeytvyd
dgeeknnatv heqvggpslt sdlqaqskgn peqtpvlkpe eeapapevga skpegidsrp
etlhpgrpqp paeeelcsgk pfdaftdlkn gslfafrgqy cyeldekavr pgypklirdv
wgiegpidaa ftrincqgkt ylfkgsqywr fedgvldpdy prnisdgfdg ipdnvdaala
lpahsysgre rvyffkgkqy weyqfqhqps qeecegssls avfehfammq rdswedifel
lfwgrtsagt rqpqfisrdw hgvpgqvdaa magriyisgm aprpslakkq rfrhrnrkgy
rsqrghsrgr nqnsrrpsra twlslfssee snlgannydd yrmdwlvpat cepiqsvfff
sgdkyyrvnl rtrrvdtvdp pyprsiaqyw lgcpapghl  -- LINK -- gqnhhevvkf
mdvyqrsych pietlvdifq eypdeieyif kpscvplmrc ggcndegle cvpteesnit
mqimrikphq gqhigemsfl qhnkcecrpk kd
```

FIGURE 15

```
   1  mlrgpgpgll llavqclgta vpstgasksk rqaqqmvqpq spvavsqskp gcydngkhyq
  61  inqqwertyl gnalvctcyg gsrgfncesk peaeetcfdk ytgntyrvgd tyerpkdsmi
 121  wdctcigagr grisctianr cheggqsyki gdtwrrphet ggymlecvcl gngkgewtck
 181  piaekcfdha agtsyvvget wekpyqgwmm vdctclgegs gritctsrnr cndqdtrtsy
 241  rigdtwskkd nrgnllqcic tgngrgewkc erhtsvqtts sgsgpftdvr aavyqpqphp
 301  qpppyghcvt dsgvvysvgm qwlktqgnkq mlctclgngv scqetavtqt yggnsngepc
 361  vlpftyngrt fyscttegrq dghlwcstts nyeqdqkysf ctdhtvlvqt qggnsngalc
 421  hfpflynnhn ytdctsegrr dnmkwcgttq nydadqkfgf cpmaaheeic ttnegvmyri
 481  gdqwdkqhdm ghmmrctcvg ngrgewtcia ysqlrdqciv dditynvndt fhkrheeghm
 541  lnctcfgqgr grwkcdpvdq cqdsetgtfy qigdswekyv hgvryqcycy grgigewhcq
 601  plqtypsssg pvevfitetp sqpnshpiqw napqpshisk yilrwrpkns vgrwkeatip
 661  ghlnsytikg lkpgvvyegq lisiqqyghq evtrfdfttt ststpvtsnt vtgettpfsp
 721  lvatsesvte itassfvvsw vsasdtvsgf rveyelseeg depqyldlps tatsvnipdl
 781  lpgrkyivnv yqisedgeqs lilststqtta pdappdptvd qvddtsivvr wsrpqapitg
 841  yrivyspsve gsstelnlpe tansvtlsdl qpgvqyniti yaveenqest pvviqqettg
 901  tprsdtvpsp rdlqfvevtd vkvtimwtpp esavtgyrvd vipvnlpgeh gqrlpisrnt
 961  faevtglspg vtyyfkvfav shgreskplt aqqttkldap tnlqfvnetd stvlvrwtpp
1021  raqitgyrlt vgltrrgqpr qynvgpsvsk yplrnlqpas eytvslvaik gnqespkatg
1081  vfttlqpgss ippyntevte ttivitwtpa prigfklgvr psqggeapre vtsdsgsivv
1141  sgltpgveyv ytiqvlrdgq erdapivnkv vtplspptnl hleanpdtgv ltvswerstt
1201  pditgyritt tptngqqgns leevvhadqs sctfdnlspg leynvsvytv kddkesvpis
1261  dtiipavppp tdlrftnigp dtmrvtwapp psidltnflv ryspvkneed vaelsispsd
1321  navvltnllp gteyvvsvss vyeqhestpl rgrqktglds ptgidfsdit ansftvhwia
1381  pratitgyri rhhpehfsgr predrvphsr nsitltnltp gteyvvsiva lngreesppll
1441  igqqstvsdv prdlevvaat ptslliswda pavtvryyri tygetggnsp vqeftvpgsk
1501  statisglkp gvdytitvya vtgrgdspas skpisinyrt eidkpsqmqv tdvqdnsisv
1561  kwlpssspvt gyrvtttpkn gpgptktkta gpdqtemtie glqptveyvv svyaqnpsge
1621  sqplvqtavt nidrpkglaf tdvdvdsiki awespqgqvs ryrvtyysspe dgihelfpap
1681  dgeedtaelq glrpgseytv svvalhddme sqpligtqst aipaptdlkf tqvtptslsa
1741  qwtppnvqlt gyrvrvtpke ktgpmkeinl apdsssvvvs glmvatkyev svyalkdtlt
1801  srpaqgvvtt lenvspprra rvtdatetti tiswrtktet itgfqvdavp angqtpiqrt
1861  ikpdvrsyti tglqpgtdyk iylytlndna rsspvvidas taidapsnlr flattpnsll
1921  vswqpprari tgyiikyekp gspprevvpr prpgvteati tglepgteyt iyvialknnq
1981  ksepligrkk tdelpqlvtl phpnlhgpei ldvpstvqkt pfvthpgydt gngiqlpgts
2041  gqqpsvgqqm ifeehgfrrt tppttatpir hrprpypppnv geeiqighip redvdyhlyp
2101  hgpglnpnas tgqealsqtt iswapfqdts eyiischpvg tdeeplqfrv pgtstsatlt
2161  gltrgatyni ivealkdqqr hkvreevvtv gnsvneglnq ptddscfdpy tvshyavgde
2221  wermsesgfk llcqclgfgs ghfrcdssrw chdngvnyki gekwdrqgen gqmmsctclg
2281  ngkgefkcdp heatcyddgk tyhvgeqwqk eylgaicsct cfggqrgwrc dncrrpggep
2341  spegttgqsy nqysqryhqr tntnvncpie cfmpldvqad redsre
```

FIG. 16

1-64VN:(G4S)4:1-53EGF:G4SG4:6H

DQESCKGRCTEGFNVDKKCQCDELCSYYQSCCTDYTAECKPQVTRGDVFTMPEDEYTVYD
DGEEGGGGSGGGGSGGGGSGGGGSNSDSECPLSHDGYCLHDGVCMYIEALDKYACNCVVG
YIGERCQYRDLKWWELRGGGGSGGGGHHHHHH

FIG. 18A

1-64VN:(G4S)4:1-146bFGF:G4SG4:6H

DQESCKGRCTEGFNVDKKCQCDELCSYYQSCCTDYTAECKPQVTRGDVFTMPEDEYTVYD
DGEEGGGGSGGGGSGGGGSGGGGSPALPEDGGSGAFPPGHFKDPKRLYCKNGGFFLRIHPD
GRVDGVREKSDPHIKLQLQAEERGVVSIKGVCANRYLAMKEDGRLLASKCVTDECFFFER
LESNNYNTYRSRKYTSWYVALKRTGQYKLGSKTGPGQKAILFLPMSAKSGGGGSGGGGHH
HHHH

FIG. 18B

1-64VN:(G4S)4:1-163KGF:G4SG4:6H

DQESCKGRCTEGFNVDKKCQCDELCSYYQSCCTDYTAECKPQVTRGDVFTMPEDEYTVYD
DGEEGGGGSGGGGSGGGGSGGGGSCNDMTPEQMATNVNCSSPERHTRSYDYMEGGDIRV
RRLFCRTQWYLRIDKRGKVKGTQEMKNNYNIMEIRTVAVGIVAIKGVESEFYLAMNKEGK
LYAKKECNEDCNFKELILENHYNTYASAKWTHNGGEMFVALNQKGIPVRGKKTKKEQKT
AHFLPMAITGGGGSGGGGHHHHHH

FIG. 18C

SYNTHETIC CHIMERIC PROTEINS COMPRISING EPIDERMAL GROWTH FACTOR AND VITRONECTIN

CROSS-REFERENCE TO RELATED APPLICATIONS

This application is a continuation-in-part of U.S. application Ser. No. 12/627,647, filed Nov. 30, 2009, which is a continuation-in-part of U.S. application Ser. No. 10/544,796, now U.S. Pat. No. 7,659,367, which is the National Stage of International Application No. PCT/AU2004/000117, filed Feb. 5, 2004, which claims the benefit of Australian Application No. 2003900481, filed Feb. 5, 2003, each of which is hereby incorporated in its entirety by reference herein.

FIELD OF THE INVENTION

This invention relates to protein complexes having respective domains that enable binding to and activation of both a growth factor receptor, such as the type 1 insulin-like growth factor receptor, and an integrin receptor for vitronectin or fibronectin. In particular embodiments, this invention relates to chimeric proteins comprising insulin-like growth factor-I, insulin-like growth factor-II, platelet-derived growth factor or vascular endothelium-derived growth factor receptor-binding domains and an integrin receptor-binding domain of vitronectin or fibronectin. More particularly, this invention relates to protein complexes that stimulate cell migration and to compositions and methods that promote or induce cell migration and/or proliferation. These compositions and methods may have use in wound healing, tissue engineering, cosmetic and therapeutic treatments such as skin replacement and skin replenishment and treatment of burns where epithelial cell migration and/or proliferation is required. In other embodiments, the invention provides treatment provided by the present invention related to prevention or inhibition of cancer cell metastasis, particularly in relation to breast cancer. Chimeric proteins of the invention may also be useful for the production of agonists and antagonists of the biological actions of protein complexes comprising insulin-like growth factors, vitronectin and insulin-like growth factor binding proteins.

BACKGROUND OF THE INVENTION

The insulin-like growth factors (IGFs), IGF-I and IGF-II, are mitogenic peptide growth factors involved in a broad range of cellular processes including hyperplasia, DNA synthesis, differentiation, cell cycle progression and inhibition of apoptosis (Keiss et al., 1994, Hormone Research 41 66; Wood & Yee, 2000, J. Mammary Gland Biology and Neoplasia 5 1; Jones & Clemmons, 1995, Endocrine Rev. 16 3). These effects are mediated through binding to their tyrosine-kinase linked cell surface receptor, the type 1 IGF receptor (IGF-IR). The IGFs are also tightly regulated by a family of specific binding proteins, termed IGFBPs, whose primary role is to bind free IGFs and thereby moderate their half-life, specificity and activity (Clemmons, 1998, Mol. Cell. Endocrinol. 140 19).

Recently, vitronectin (VN) has been shown to bind directly to IGF-II (Upton et al., 1999. Endocrinology 140 2928-31) while IGF-I can bind to VN in the presence of certain IGFBPs, as described in International Publication WO 02/24219. The finding that VN, an ECM organization and adhesion molecule, binds IGF-II with an affinity that is similar to that of IGF-II for IGF-IR (Upton et al., 1999, supra), its biologically relevant receptor, reveals a specific physical link between IGF action and VN in the ECM. In addition, IGF-II bound to VN can stimulate synergistic functional responses in human keratinocytes in vitro (International Publication WO 02/24219).

VN is a glycoprotein that is highly abundant in the blood and in the ECM. Primarily synthesized in the liver, but expressed by many other cell types, VN circulates in the blood in a closed conformation and is deposited in the ECM in an open, or extended, conformation (Schvartz et al., 1999, The International Journal of Biochemistry and Cell Biology 31 531-44). Both conformations are believed to bind IGF-II (Upton et al., 1999, supra; International Publication WO 02/24219; McMurty et al., 1996, Endocrinology 150:149-60) and also bind multiple other ligands including collagen (Morris et al., 1994, Journal of Biological Chemistry 269 23845-52), glycosaminoglycans (Francois et al., 1999, Journal of Biological Chemistry 274: 37611-19), many other ECM proteins and a wide variety of integrins, particularly the $\alpha_v$ integrins. Indeed, the primary role of vitronectin is as an ECM organization molecule that provides adhesive links to these cell surface integrin receptors via an RGD binding motif. The VN receptors ($\alpha_v$ integrins) have been shown to regulate the actin cytoskeleton rearrangement required for growth and invasion, hence, VN binding coordinates cell adhesion and movement (DePasquale, 1998, Histochemistry and Cell Biology 110: 485-94; Huang, 2000, Oncogene 19 1915-23).

However, the respective, relative contributions of IGFs and VN present in protein complexes, in terms of stimulating biological responses such as cell migration and/or proliferation, has remained elusive, as has the site of protein-protein interaction between IGFs/IGFBPs and VN.

SUMMARY OF THE INVENTION

The present inventors have discovered that protein complexes comprising IGF-II and VN, IGF-I and IGFBP and VN or FN, and EGF, bFGF and KGF and VN or FN stimulate cell migration and/or proliferation by binding and synergistically co-activating cognate growth factor receptors and VN-binding integrin receptors.

Furthermore, a polyanionic domain of VN has been identified as a proposed binding site of either IGFs or IGFBPs.

Therefore, the invention is broadly directed to isolated protein complexes that comprise a receptor-binding domain of a growth factor domain and a domain of vitronectin or fibronectin that is capable of binding an integrin receptor, wherein the isolated protein complex can co-activate the growth factor and integrin receptor to thereby elicit a biological response.

In a first aspect, the invention provides an isolated protein complex comprising:
 (i) a growth factor, or at least a domain of a growth factor which is capable of binding a cognate growth factor receptor; and
 (ii) vitronectin (VN) or fibronectin (FN), or at least an integrin-binding domain of VN or FN.

In a second aspect, the invention provides an isolated protein complex in the form of a synthetic chimeric protein comprising an amino acid sequence of:
 (i) a growth factor, or at least a domain of a growth factor which is capable of binding a cognate growth factor receptor; and
 (ii) vitronectin (VN) or fibronectin (FN), or at least an integrin-binding domain of VN or FN.

Preferably, according to the aforementioned aspects the growth factor is IGF-I, IGF-II, EGF, bFGF, or KGF.

More preferably, the growth factor is EGF, bFGF or KGF.

In embodiments where the growth factor is IGF-I, suitably said at least a domain of IGF-I includes residue 24 of IGF-I.

In embodiments where the growth factor is IGF-II, suitably said at least a domain of IGF-II includes residue 27 of IGF-II.

In alternative embodiments, the growth factor is VEGF or PDGF.

Preferably, in embodiments relating to VN, the integrin receptor is an $\alpha_v$ integrin.

More preferably, the integrin receptor is an $\alpha_v\beta_3$ integrin or an $\alpha_v\beta_5$ integrin.

Preferably, in embodiments relating to FN, the integrin receptor is an $\alpha_I$ or an $\alpha_4$ integrin.

This aspect of the invention also includes within its scope amino acid deletions, additions, substitutions and/or mutations of amino acid sequences corresponding to (i) and (ii) above.

In a third aspect, the invention provides an isolated nucleic acid encoding the isolated protein complex of the second aspect.

In a fourth aspect, the invention provides a genetic construct comprising the isolated nucleic acid of the third aspect operably linked to one or more regulatory sequences in an expression vector.

Preferably, the genetic construct is an expression construct.

In a fifth aspect, the invention provides a host cell comprising the genetic construct of the fourth aspect.

In sixth aspect, the invention provides a pharmaceutical composition comprising the isolated protein complex of the first aspect or the synthetic protein of the second aspect and a pharmaceutically-acceptable carrier, diluent or excipient.

This aspect of the invention also contemplates a pharmaceutical composition comprising the host cell of the fifth aspect, which cell expresses said synthetic protein(s).

In a seventh aspect, the invention provides an antibody specific for the synthetic protein of the second aspect.

In an eighth aspect, the invention provides a method of promoting cell migration including the step of using a synthetic protein to bind both a growth factor receptor and an integrin receptor.

Preferably, the growth factor receptor is EGF receptor, bFGF receptor or KGF receptor.

Preferably, in embodiments relating to VN, the integrin receptor is an $\alpha_v$ integrin.

More preferably, the integrin receptor is an $\alpha_v\beta_3$ integrin or an $\alpha_v\beta_5$ integrin.

Preferably, in embodiments relating to FN, the integrin receptor is an $\alpha_1$ or an $\alpha_4$ integrin.

In a preferred embodiment, this aspect of the invention relates to promotion or induction of epithelial/keratinocyte/fibroblast cell migration and/or proliferation to facilitate wound healing in mammals, preferably humans.

Preferably, said synthetic protein is as according to the first aspect of the invention.

In an ninth aspect, the invention provides a method of preventing cell migration and/or proliferation, including the step of preventing, inhibiting or otherwise reducing binding of both a growth factor receptor and an integrin receptor by a complex comprising a growth factor and vitronectin or fibronectin.

Preferably, the growth factor receptor is EGF receptor, bFGF receptor or KGF receptor.

Preferably, in embodiments relating to VN, the integrin receptor is an $\alpha_v$ integrin.

More preferably, the integrin receptor is an $\alpha_v\beta_3$ integrin or an $\alpha_v\beta_5$ integrin.

Preferably, in embodiments relating to FN, the integrin receptor is an $\alpha_1$ or an $\alpha_4$ integrin.

In a preferred embodiment, this aspect of the invention relates to prevention or inhibition of metastatic cancer cell migration and/or proliferation in mammals, preferably humans.

A particular example contemplated by this aspect of the invention is prevention or inhibition of breast cancer metastasis.

It will also be appreciated that the methods of the eighth and ninth aspects may encompass prophylactic and therapeutic methods of treatment.

In a tenth aspect, the invention provides use of the isolated protein complex of the first aspect or the synthetic protein of the second aspect to produce a molecule that:
(i) is an agonist of protein complexes comprising a growth factor and vitronectin or fibronectin; or
(ii) is an antagonist of protein complexes comprising a growth factor and vitronectin or fibronectin.

In a preferred embodiment, the invention provides use of the synthetic protein of the first aspect to produce a molecule that:
(i) is an agonist of IGF-II:VN or IGF-I:IGFBP:VN protein complexes;
(ii) is an antagonist of IGF-II:VN or IGF-I:IGFBP:VN protein complexes;
(iii) is an agonist of IGF-II:FN or IGF-I:IGFBP:FN protein complexes; or
(iv) is an antagonist of IGF-II:FN or IGF-I:IGFBP:FN protein complexes.

Agonists and/or antagonists produced according to this aspect of the invention may have particular efficacy in promoting wound healing, tissue engineering, skin regeneration and/or prevention of cancer cell metastasis or hyperproliferative disorders of the skin such as scarring and psoriasis.

In an eleventh aspect, the invention provides a biomaterial that comprises the isolated protein complex of the first or second aspect.

In particular embodiments, the biomaterial may be a surgical implant, prosthesis, scaffold, wound or burn dressing or the like suitably impregnated, coated or otherwise comprising an isolated protein complex of the invention.

BRIEF DESCRIPTION OF THE FIGURES AND TABLES

FIG. 1 illustrates migration of HaCAT human skin keratinocyte cells seeded into the upper chamber of 12 μm pore Transwells™ to the lower surface, in response to the lower chamber being coated with IGF-II prebound to VN (black bars), or IGF-II "bound" to the dishes in the absence of VN (grey bars). Each bar represents the average number of cells on the lower membrane after 5 hours incubation and are obtained from three replicate experiments in which treatments were analyzed in triplicate wells.

FIG. 2 illustrates migration of MCF-7 human breast cancer cells seeded into the upper chamber of 12 μm pore Transwells™ to the lower surface, in response to the lower chamber being coated with IGF-II prebound to VN (striped bars), or IGF-II "bound" to the dishes in the absence of VN (white bars). Each bar represents the average number of cells on the lower membrane after 5 hours incubation and are obtained from three replicate experiments in which treatments were analyzed in triplicate wells. Data points where the effect of the complex is significantly different to that of VN alone are indicated by an asterisk.

FIG. 3 illustrates migration of MCF-7 human breast cancer cells seeded into the upper chamber of 12 μm pore Transwells™ to the lower chamber that had been coated with VN, native IGF-II bound to VN (striped bars) or $L^{27}$-IGF-II bound to VN (black bars). Each data point is paired with a VN free control (white bars) containing the same amount of IGF-II in the absence of VN. Each bar represents the average number of cells on the lower membrane after 5 hours incubation obtained from two replicate experiments in which treatments were analyzed in triplicate wells.

FIG. 4 illustrates migration of MCF-7 human breast cancer cells seeded into the upper chamber of 12 μm pore Transwells™ to the lower chamber that had been prebound with VN only, native IGF-II bound to VN (striped bars) or Des(1-6) IGF-II bound to VN (black bars). Each data point is paired with a VN free control (white bars) containing the same amount of IGF-II in the absence of VN. Each bar represents the average number of cells on the lower membrane after 5 hours incubation obtained from two replicate experiments in which treatments were analyzed in triplicate wells.

FIG. 5 illustrate migration of MCF-7 human breast cancer cells through Transwells™ in response to IGF-II in the presence of mAb2021Z, an $α_v$ function blocking Ab. MCF-7 cells that had been treated with the $α_v$ function blocking Ab were seeded onto Transwells™ that had been coated with VN+/−IGF-II and allowed to migrate through the porous membrane for five hours. The number of cells transversing the membrane were then determined by extracting the stain from the fixed cells and reading optical density. Treatments were then expressed as a percentage of cells migrating on VN alone in the presence or absence of Ab. The data was pooled from quadruplicate treatments of a single experiment. Bars, SEM. Asterisk indicates significant differences between treatments of the untreated or Ab treated cells with the Ab ($P<0.1$).

FIG. 6 illustrates migration of MCF-7 human breast cancer cells seeded into the upper chamber of 12 μm pore Transwells™ to the lower chamber that had been coated with VN (white bar); VN+IGFBP-5 (grey bar); native IGF-I+VN (lighter solid bar), or native IGF-I+IGFBP-5+VN (darker solid bar); $L^{24}$-IGF-I+VN (left striped bar) or $L^{24}$-IGF-I+IGFBP-5+VN (right striped bar). Each bar represents the average number of cells on the lower membrane after 5 hours incubation obtained from two replicate experiments in which treatments were analyzed in triplicate wells.

FIG. 7 illustrates the amino acid sequence of vitronectin (SEQ ID NO:1), including residue references for the various domains within vitronectin, as well as residue modification sites, ligand binding sites and protease recognition sites.

FIG. 8 illustrates the structural relationship of (a) full-length VN (75 kDa) and (b) yolk VN (54 kDa) showing ligand binding sites. Both mammalian and avian serum VN have the same domain structure, however, there are differences in the amino acid sequence. Yolk VN (54 kDa) is a truncated form of these proteins. The abbreviations used are: Som B, Somatomedin B; Connecting, Connecting domain; Hemopexin, Hemopexin-like repeat; HBD, Heparin binding domain; PAI-1, plasminogen activator inhibitor-1; uPAR, urokinase plasminogen activator receptor; TAT, thrombin-antithrombin III complex; uPA, urokinase plasminogen activator; ----, polyanionic region (basic region); +++, polycationic region (acidic region).

FIG. 9 illustrates purification of 54 kDa yolk VN from chicken egg yolk. SDS-PAGE analysis of protein sample loaded onto Q-Sepharose matrix (lane L) and the purified product eluted (lane E). Lane M indicates molecular weight markers (BioRad Low Range Markers) (BioRad, Richmond, Calif., USA). Pre-cast polyacrylamide 4-20% gradient gels (Gradipore, Frenchs Forest, NSW, Australia) were used to analyse the proteins.

FIG. 10 illustrates solid plate binding assay assessing the ability of [$^{125}$I]–IGF-I/IGFBP-3 to bind to the purified VNs. The solid plate binding assay was carried out as previously described by Kricker, et al., 2003 Endocrinology 144 2807-2815. Briefly, purified VNs were pre-coated to Immulon 96 well plates at 4° C. overnight. Radiolabelled IGF-I/IGFBP-3 complexes were then added and allowed to bind to the VN overnight after which unbound material was removed. Binding of [$^{125}$I]–IGF-I/IGFBP-3 to VN bound to the wells was determined in a γ-counter (n=18). Human VN: VN purified from human serum; Yolk VN 75: purified 75 kDa yolk VN; Yolk VN 54: purified 54 kDa yolk VN.

FIG. 11 illustrates Cell Growth Assay (MTT) (48 hr): HaCAT cell growth in response IGF:VN complexes. The IGF:VN complexes were pre-coated to wells with HaCAT cells seeded and allowed to grow for 48 hr. After this time they were assessed for cell growth by metabolic activity using the MTT method (Denizot & Lang, 1986 The Journal of Immunological Methods 89 271-277) (n=3). Human VN: VN purified from human serum; Yolk VN 75: purified 75 kDa yolk VN; Yolk VN 54: purified 54 kDa yolk VN; IGF-I/BP3: Insulin-like growth factor-I and insulin-like growth factor binding protein 3.

FIG. 12 illustrates Transwell™ migration assay (5 hr): HaCAT migration in response to IGF:VN complexes. HaCAT cells were seeded into a Transwell™ coated with IGF-I:IGFBP-3:VN complexes and allowed to migrate for 5 hr as described previously (Kricker, et al., 2003, supra). Cells which had migrated were stained with crystal violet and optical density read at 595 nm. Each treatment was completed in duplicate (n=2). Human VN: VN purified from human serum; Yolk VN 75: purified 75 kDa yolk VN; Yolk VN 54: purified 54 kDa yolk VN; IGF-I/BP3: Insulin-like growth factor-I and insulin-like growth factor binding protein 3.

FIG. 13 illustrates amino acid sequence of (A) the mature vitronectin protein (SEQ ID NO:2), (B) IGF-I (SEQ ID NO:3) and (C) preferred linker sequences (SEQ ID NOS:4-8).

FIG. 14 shows the amino acid sequences of various embodiments of IGF-I and VN-containing chimeric proteins (SEQ ID NOS:9-22). FIG. 14A shows embodiments (A) to (E) of IGF-I and VN-containing chimeric proteins (SEQ ID NOS:9-13). FIG 14B illustrates embodiments (F) to (I) of IGF-I and VN-containing chimeric proteins (SEQ ID NOS: 14-17) FIG. 14C illustrates embodiments (J) to (M) of IGF-I and VN-containing chimeric proteins (SEQ ID NOS: 18-21). FIG. 14D illustrates embodiment (N) of an IFG-I and VN-containing chimeri protein (SEQ ID NO:22).

FIG. 15 illustrates Amino acid sequences of embodiments of (A) PDGF and VN containing chimeric-protein (SEQ ID NO:23) and (B) VEGF and VN-containing chimeric protein (SEQ ID NO:24).

FIG. 16 illustrates Amino acid sequence of mature human fibronectin (FN) (SEQ ID NO:25).

Figure 17:
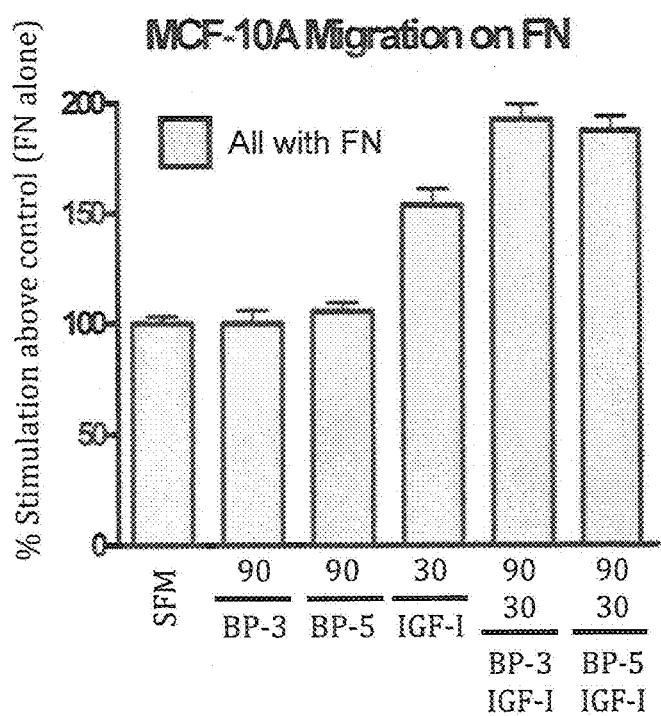

FIG. 17 illustrates IGF-I, IGFBP and FN protein complexes stimulate breast cancer cell migration. MCF-10A cells were seeded onto Transwells that had been coated with FN (1 μg/mL) and increasing concentrations of IGF-I prebound in the presence of IGFBP-3 or -5. The cells where allowed to migrate for 5 hours. The number of cells traversing the membrane in response to each treatment was then expressed as a percentage of those that migrated on FN only (SFM). MCF-10 data are pooled from three experiments with treatments tested in four wells in each replicate experiment. Error bars indicate SEM. SFM=Serum-free media.

FIG. 18 illustrates (A) to (C) Amino acid sequences of embodiments of EGF, bFGF and KGF, respectively, and VN-containing chimeric proteins (SEQ ID NOs:27-29).

Figure 19:
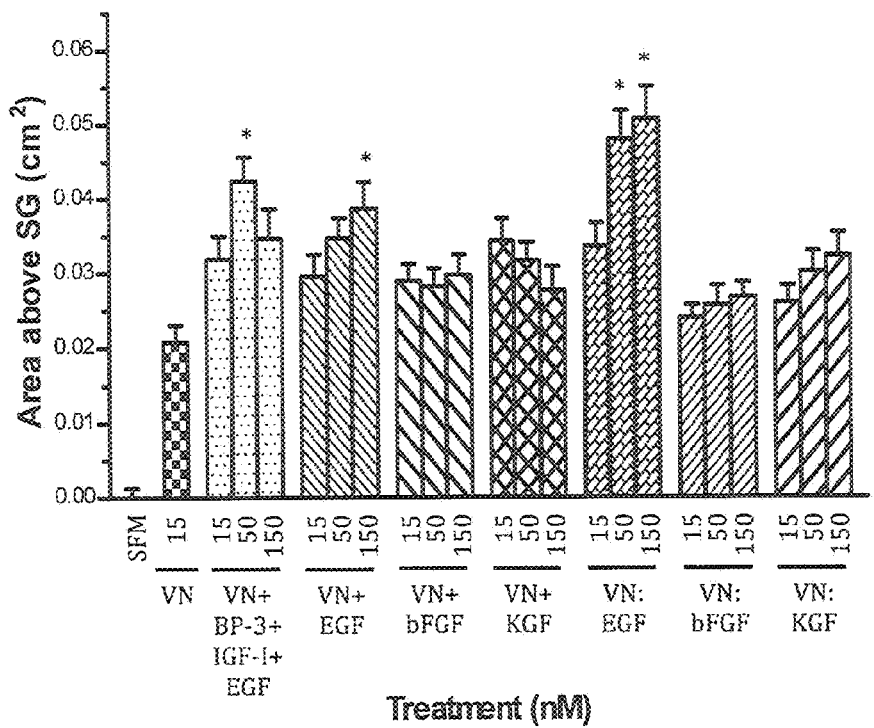

FIG. 19 illustrates EGF, bFGF and KGF VN chimeric proteins stimulate primary keratinocyte cell migration. Migration of isolated skin keratinocyte cells seeded within the inner chamber of a seeding insert which was removed to allow outward migration, in response to the culture well being coated with VN:EGF, VN:bFGF and VN:KGF chimeras, and controls. Each bar represents the average area (+/−SEM) of cell coverage after 24 hours incubation and are obtained from at least three replicate experiments in which treatments were analysed in triplicate wells. *=p≤0.05 compared to VN alone.

Figure 20:
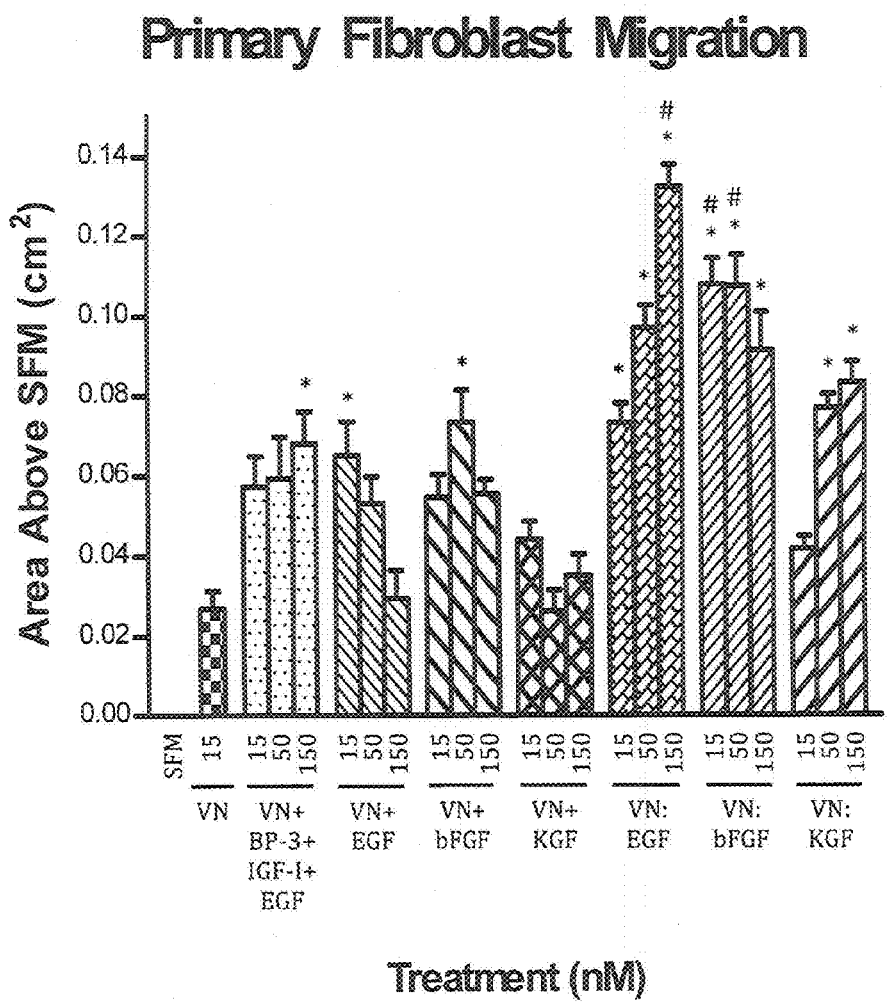

FIG. 20 illustrates EGF, bFGF and KGF VN chimeric proteins stimulate primary fibroblast cell migration. Migration of isolated skin fibroblast cells seeded within the inner chamber of a seeding insert which was removed to allow outward migration, in response to the culture well being coated with VN:EGF, VN:bFGF and VN:KGF chimeras, and controls. Each bar represents the average area (+/−SEM) of cell coverage after 24 hours incubation and are obtained from at least three replicate experiments in which treatments were analysed in triplicate wells. *=p≤0.05 compared to VN alone. #=p≤0.05 compared to VN:BP-3:IGF-I:EGF 150 (Best VG treatment).

Figure 21:
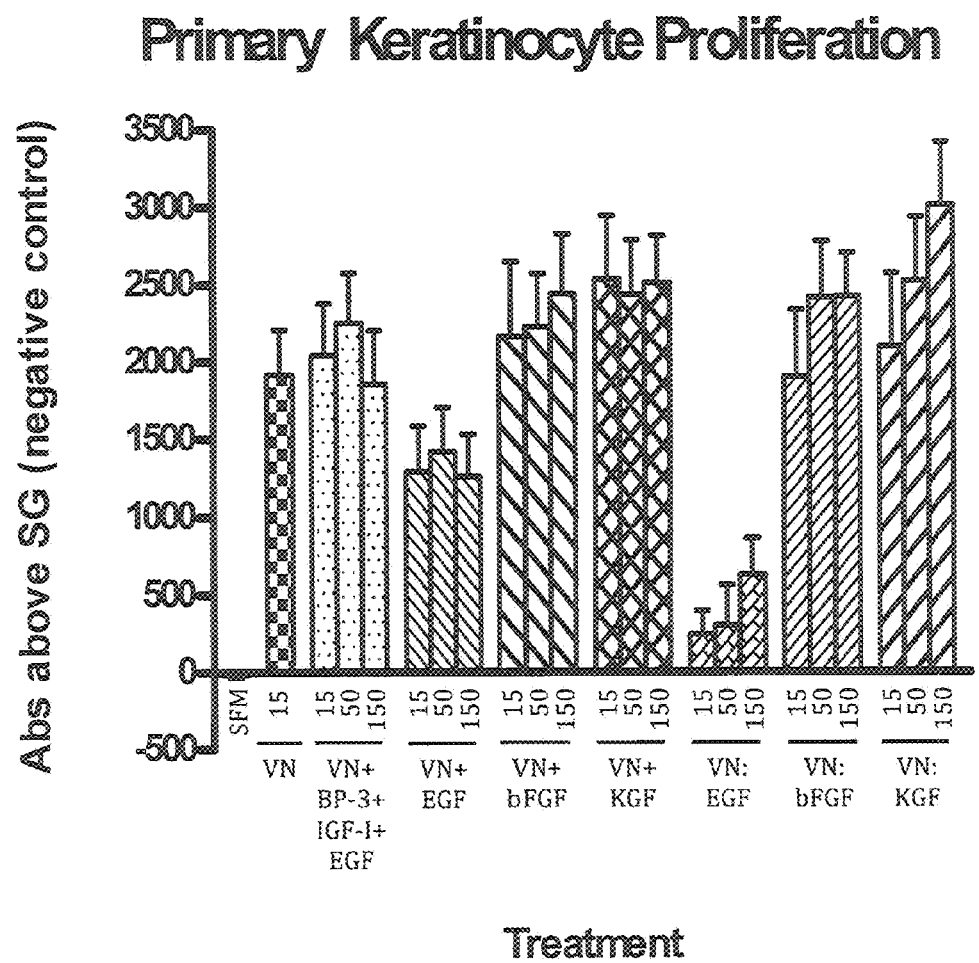

FIG. 21 illustrates EGF, bFGF and KGF VN chimeric proteins stimulate primary keratinocyte cell proliferation. Proliferation of isolated skin keratinocyte cells in response to the culture well being coated with VN:EGF, VN:bFGF and VN:KGF chimeras, and controls. Each bar represents the average absorbance (+/−SEM) of DNA-binding GR dye (representative of cell number) after 72 hours incubation and are obtained from at least three replicate experiments in which treatments were analysed in triplicate wells.

Figure 22:
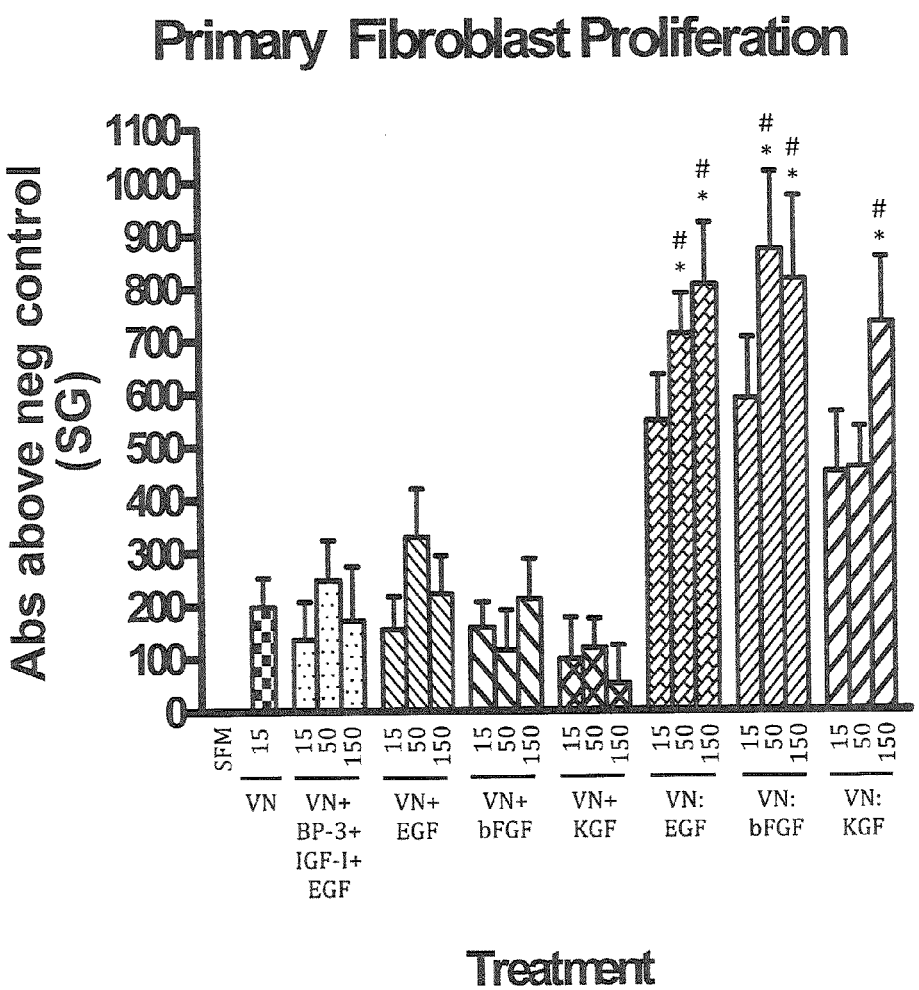

FIG. 22 illustrates EGF, bFGF and KGF VN chimeric proteins stimulate primary fibroblast cell proliferation. Proliferation of isolated skin fibroblast cells in response to the culture well being coated with VN:EGF, VN:bFGF and VN:KGF chimeras, and controls. Each bar represents the average absorbance (+/−SEM) of DNA-binding GR dye (representative of cell number) after 24 hours incubation and are obtained from at least three replicate experiments in which treatments were analysed in triplicate wells. *=p≤0.05 compared to VN alone. #=p≤0.05 compared to VN:BP-3:IGF-I:EGF 50 (Best VG treatment).

DETAILED DESCRIPTION OF THE INVENTION

The present invention has arisen from the discovery that protein complexes comprising IGF-II and VN or IGF-I and IGFBP and VN bind and exert their biological effect on cell migration through the IGF-IR receptor and the VN-binding integrin receptor expressed by responsive cells. More particularly, this dual binding event synergistically stimulates cell migration and/or proliferation, as has been shown by the present inventors in both a keratinocyte model and a breast cancer cell model.

Furthermore, it has surprisingly been discovered that the domain of VN which appears to interact or bind with IGF-II and IGFBPs is a polyanionic region corresponding to amino acids 53-64 of mature VN.

This discovery has led the present inventors to provide an isolated protein complex that comprises at least the minimal domain or region of IGF-I or IGF-II capable of binding the IGF-IR in combination with the integrin-binding domain of VN. Even more particularly, a single, contiguous protein may be produced which comprises these domains.

Such protein complexes, whether comprising multiple proteins or in the form of a single synthetic protein, are expected to coordinately bind or co-ligate the IGF-IR and the VN-binding integrin receptor and thereby be a useful agent for the promotion of cell migration and/or proliferation and wound healing. Analogously, it is proposed by the present inventors that prevention of the IGF-IR and the VN-binding integrin receptor co-ligation could be used to prevent cancer cell metastasis. It is also proposed that this discovery may be extendible to protein complexes comprising other growth factors such as PDGF and VEGF, although without limitation thereto, and to other integrin-binding proteins such as fibronectin (FN).

In this regard, the present inventors have shown that isolated protein complexes comprising IGF-I, IGFBPs and FN stimulate cell migration.

Throughout this specification, unless otherwise indicated, "comprise", "comprises" and "comprising" are used inclusively rather than exclusively, so that a stated integer or group of integers may include one or more other non-stated integers or groups of integers.

In the particular context of growth factor receptor-binding domains and integrin-binding domains, such a domain will comprise an amino acid sequence of the domain, together with other, additional amino acids as desired.

It will be understood also that such a domain may "consist essentially of" the amino acid sequence of the domain, together with no more than ten, preferably no more than five or even more preferably no more than four, three, two or one additional amino acids.

It will be understood also that such a domain may "consist of" the amino acid sequence of the domain, in the absence of any additional amino acids.

For the purposes of this invention, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in native, chemical synthetic or recombinant form.

As used herein, by "synthetic" is meant not naturally occurring but made through human technical intervention. In the context of synthetic proteins and nucleic acids, this encompasses molecules produced by recombinant, chemical synthetic or combinatorial techniques as are well understood in the art.

By "protein" is meant an amino acid polymer. The amino acids may be natural or non-natural amino acids, D- or L-amino acids as are well understood in the art. The term "protein" also includes and encompasses such terms as "glycoprotein", "lipoprotein" and the like, as are commonly used in the art.

A "peptide" is a protein having less than fifty (50) amino acids.

A "polypeptide" is a protein having fifty (50) or more amino acids.

As hereinbefore described, the present invention provides, in one particular aspect, an isolated protein complex comprising:
  (i) a growth factor or at least a domain of a growth factor which is capable of binding a cognate growth factor receptor; and (ii) at least an integrin-binding domain of vitronectin or fibronectin.

As used herein, a "growth factor" is a biologically active protein that is capable of regulating cell growth, differentiation, survival and/or migration in vitro and/or in vivo.

Preferably, the growth factor is selected from the group consisting of IGF-I, IGF-II, VEGF and PDGF.

More preferably, the growth factor is selected from IGF-I and IGF-II.

However, the invention also contemplates other biologically active proteins that regulate cell growth, differentiation, survival and/or migration such as epidermal growth factor (EGF; Heldin et al., 1981, Science 4 1122-1123; UniProtKB/Swiss-Prot: #P01133), fibroblast growth factor (FGF; Nurcombe et al., 2000, J. Biol. Chem. 275 30009-30018), basic fibroblast growth factor (bFGF; Taraboletti et al., 1997, Cell Growth. Differ. 8 471-479; UniProtKB/Swiss-Prot: #P09038), osteopontin (Nam et al., 2000, Endocrinol. 141 1100), thrombospondin-1 (Nam et al., 2000, supra), tenascin-C (Arai et al., 1996, J. Biol. Chem. 271 6099), PAI-1 (Nam et al., 1997, Endocrinol. 138 2972), plasminogen (Campbell et al., 1998, Am. J. Physiol. 275 E321), fibrinogen (Campbell et al., 1999, J. Biol. Chem 274 30215), fibrin (Campbell et al., 1999, supra), transferrin (Weinzimer et al., 2001, J. Clin. Endocrinol. Metab. 86 1806), or keratinocyte growth factor (KGF; Marchese et al., 1990, J. Cell Physiol. 144 326-32; UniProtKB/Swiss-Prot: #P21781).

Isolated protein complexes of the invention comprise a growth factor or at least a domain of a growth factor of a growth factor which is capable of binding a cognate growth factor receptor.

In this context, by "domain" is meant at least that portion or region of a growth factor that is capable of binding a cognate growth factor receptor. Typically, although not exclusively, the cognate growth factor receptor is expressed by a cell and binding or ligation of said cognate growth factor receptor by said at least a domain of a growth factor elicits a cellular response such as cell growth, differentiation, survival and/or migration.

With particular regard to IGF-I, said domain suitably comprises amino acid residue 24, which is not a leucine residue.

Typically, said residue is tyrosine.

With particular regard to IGF-II, said domain suitably comprises amino acid residue 27, which is not a leucine residue.

Typically, said residue is tyrosine.

With particular regard to IGF-I, in one embodiment said domain consists of residues 1 to 70 of IGF-I.

In another embodiment, said domain consists of residues 4 to 70 of IGF-I.

It will also be understood that another component of isolated protein complexes of the invention is at least an integrin-binding domain of vitronectin or fibronectin.

Preferably, in embodiments relating to VN, the integrin receptor is an $\alpha_v$ integrin.

More preferably, the integrin receptor is an $\alpha_v\beta_3$ integrin or an $\alpha_v\beta_5$ integrin.

Preferably, in embodiments relating to FN, the integrin receptor is an $\alpha_1$ or an $\alpha_4$ integrin.

As will be described in more detail hereinafter, the present inventors show that the HBD of VN is not required for the full biological activity of isolated protein complexes.

Further to this, the present inventors have shown that isolated protein complexes comprising IGF-I, IGFBPs and FN stimulate cell migration.

It will be readily appreciated from the foregoing that isolated protein complexes of the invention may be in the form of non-covalently associated oligo-protein complexes, oligoprotein complexes that have been covalently cross-linked (reversibly or irreversibly) or in the form of synthetic, chimeric proteins.

Accordingly, in a particular aspect the invention provides an isolated protein complex in the form of a synthetic chimeric protein comprising an amino acid sequence of:
  (i) a growth factor, or at least a domain of a growth factor which is capable of binding a cognate growth factor receptor; and
  (ii) vitronectin (VN) or fibronectin (FN), or at least an integrin-binding domain of VN or FN.

As used herein, a "chimeric protein", comprises a contiguous sequence of amino acids derived from an integrin-receptor binding domain of VN or FN and a growth factor or at least a receptor-binding domain of a growth factor.

Although not wishing to be bound by any particular theory, it is proposed that synthetic chimeric proteins may be able to co-ligate and co-activate a cognate receptor for said growth factor and an integrin receptor for VN or FN to thereby stimulate, induce, augment or otherwise promote cell migration.

An advantage of chimeric proteins according to the invention is that they are readily produced by chemical synthetic or recombinant means and are expected to be more stable in vivo, as they do not rely on maintaining the protein-protein interactions that are required in non-covalent oligo-protein complexes.

In this regard, although isolated protein complexes that comprise receptor binding domains of IGF-I would also comprise an IGFBP, it is proposed that according to the aforementioned mode of action, an IGFBP is preferably not present in an IGF-I/VN or in an IGF-I/FN synthetic chimera.

Also with regard to VN, as will be described in more detail hereinafter, the present inventors show that it is most likely the polyanionic region of VN that is required for interaction with IGF-II or IGF-I/IGFBP complexes.

Figure 8:
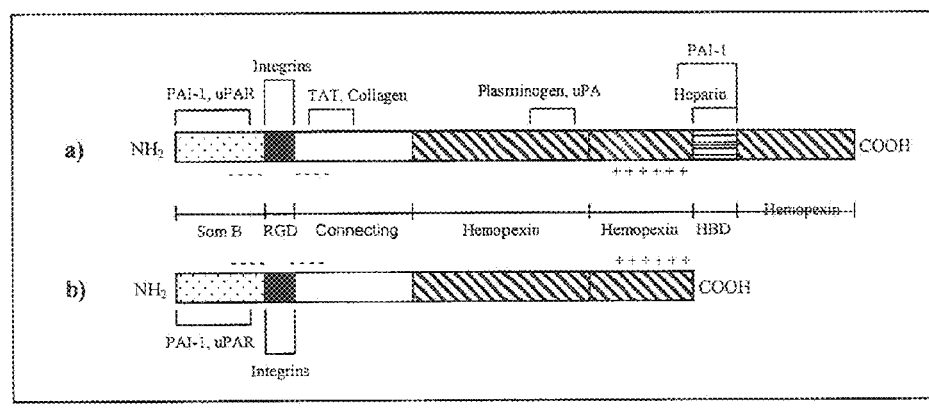

Referring to FIG. 7 and FIG. 8, the polyanionic region is residues 53-64 of the mature VN sequence (SEQ ID NO:2).

In light of the foregoing, the present invention contemplates embodiments of synthetic chimeric proteins that do not include the HBD and/or the polyanionic region of VN.

With regard to VN proteins and amino acid sequences thereof that do not include the HBD and/or the polyanionic region, these may be naturally occurring proteins such as the 54kD chicken yolk VN (lacking a HBD) or may be engineered by deletion, mutation or truncation of a VN protein or amino acid sequence so that the HBD and/or the polyanionic region are absent or at least substantially non-functional.

Techniques such as proteolytic digestion and site directed mutagenesis may be utilized for this purpose, as are well understood in the art.

In particular embodiments, said at least an integrin-binding domain of VN has an amino acid sequence selected from the group consisting of:
  (i) amino acid residues 1 to 459 of VN;
  (ii) amino acid residues 1 to 379 of VN;
  (iii) amino acid residues 1 to 311 of VN;
  (iv) amino acid residues 1 to 130 of VN;
  (v) amino acid residues 1 to 125 of VN;
  (vi) amino acid residues 1 to 64 of VN; and
  (vii) amino acid residues 1 to 52 of VN.

Additional amino acid sequences which also may be included are selected from the group consisting of:
  (v) amino acid residues 65 to 459 of VN;
  (vi) amino acid residues 347 to 459 of VN; and
  (vii) amino acid residues 347 to 379 of VN.

The aforementioned sequences may be used in combination, for example amino acid residues 1 to 130 of VN and amino acid residues 347 to 459 of VN or amino acid residues 1 to 52 of VN and amino acid residues 65 to 459 of VN.

Particular, non-limiting examples of chimeric proteins comprising IGF-1 and VN are set forth in FIG. 14.

Furthermore, particular non-limiting examples of chimeric proteins comprising VEGF and VN or PDGF and VN are set forth in FIG. 15.

Additionally, particular non-limiting examples of chimeric proteins comprising EGF and VN, bFGF and VN or KGF and VN are set forth in FIG. 18, and include: 1-64 VN:(Gly$_4$ Ser)$_4$:1-53 EGF:Gly$_4$ Ser Gly$_4$:6 His (SEQ ID NO:27), 1-64 VN:(Gly$_4$ Ser)$_4$: 1-146 bFGF:Gly$_4$ Ser Gly$_4$:6 His (SEQ ID NO:28) and 1-64 VN:(Gly$_4$ Ser)$_4$: 1-163 KGF:Gly$_4$ Ser Gly$_4$:6 His (SEQ ID NO:29).

Further non-limiting examples of chimeric proteins comprising EGF and VN include: 1-125 VN:(Gly$_4$ Ser)$_4$:1-53 EGF:Gly$_4$ Ser Gly$_4$:6 His; 1-311 VN:(Gly$_4$ Ser)$_4$:1-53 EGF: Gly$_4$ Ser Gly$_4$:6 His; and 1-459 VN:(Gly$_4$ Ser)$_4$:1-53 EGF: Gly$_4$ Ser Gly$_4$:6 His.

Further non-limiting examples of chimeric proteins comprising bFGF and VN include: 1-125 VN:(Gly$_4$ Ser)$_4$:1-146 bFGF:Gly$_4$ Ser Gly$_4$:6 His; 1-311 VN:(Gly$_4$ Ser)$_4$:1-146 bFGF:Gly$_4$ Ser Gly$_4$:6 His; and 1-459 VN:(Gly$_4$ Ser)$_4$:1-146 bFGF:Gly$_4$ Ser Gly$_4$:6 His.

Further non-limiting examples of chimeric proteins comprising KGF and VN include: 1-125 VN:(Gly$_4$ Ser)$_4$:1-163 KGF:Gly$_4$ Ser Gly$_4$:6 His; 1-311 VN:(Gly$_4$ Ser)$_4$:1-163 KGF: Gly$_4$ Ser Gly$_4$:6 His; and 1-459 VN:(Gly$_4$ Ser)$_4$:1-163 KGF: Gly$_4$ Ser Gly$_4$:6 His.

In other embodiments, the invention provides isolated protein complexes, such as in the form of synthetic chimeric proteins, comprising IGF-I, IGF-II, EGF, bFGF, or KGF and VN or FN, or a fragment of VN or FN that comprises at least an integrin-binding domain of VN or FN.

Preferably, in embodiments relating to FN, the integrin receptor is an $\alpha_1$ or an $\alpha_4$ integrin receptor.

In this context, by "fragment" is meant a domain, subsequence or portion of VN or FN. The fragment preferably constitutes less than 500, less than 400, less than 300 or more preferably about 80-280 contiguous amino acids of a mature VN or FN sequence.

The integrin binding domain of FN suitably comprises an RGD sequence. The RGD sequence is located in fibronectin type III domains 8 to 10 (amino acids 1299-1572 of a mature FN sequence). More specifically, the RGD sequence is present in the fibronectin type III domain defined by amino acids 1479-1572 of the mature FN sequence, although secondary integrin-binding sites may be present across the larger 8 to 10 domain region.

Accordingly, in one particular embodiment, the synthetic chimera comprises an FN fragment comprising an RGD sequence, wherein the fragment comprises or consists of at least 6, at least 10, at least 20, at least 50, at least 60, at least 70, at least 80 at least 90 or all of amino acids 1479-1572 of a mature FN amino acid sequence.

In another particular embodiment, the synthetic chimera comprises an FN fragment comprising an RGD sequence, said fragment comprising or consisting of an amino acid sequence of at least 6, at least 10 at least 20, at least 50, at least 100, at least 150, at least 200, at least 250, at least 260 or all of amino acids 1299-1572 of a mature FN amino acid sequence.

In yet another particular embodiment, the synthetic chimera comprises an FN fragment comprising an RGD sequence according to the aforementioned embodiments, wherein said synthetic chimera further comprises at least 10, 20, 50, 100, 200, 300, 500, 800 or 1000 of amino acid of a mature FN amino acid sequence, for example N-terminal of residues 1299 and/or C-terminal of residue 1572.

In still another particular embodiment, the synthetic chimera comprises an FN fragment comprising or consisting of an amino acid sequence of at least 6, at least 10 at least 20, at least 50, at least 100, at least 150, at least 200, at least 250, at least 300, at least 350, or all of amino acids 1142 to 1505 of a mature FN amino acid sequence.

It will be appreciated that the foregoing FN sequence numbering is made with reference to the mature FN sequence shown in FIG. 16. This FN sequence is derived from the UniProtKB Protein Database, protein accession number P02751. The mature form numbering takes into account the cleavage of the signal peptide.

Preferably, synthetic chimeras comprising FN or a fragment comprising an integrin binding domain do not comprise an IGFBP amino acid sequence.

Preferably, synthetic chimeric proteins as hereinbefore described further comprise a "linker sequence" located between and contiguous with a growth factor sequence and a VN or FN amino acid sequence.

In one embodiment, said linker sequence comprises one or more glycine residues and one or more serine residues.

Particular examples of linker sequences may be selected from; Gly$_4$ Ser (SEQ ID NO:4); Gly$_4$ Ser$_3$ (SEQ ID NO:5); (Gly$_4$ Ser)$_3$ (SEQ ID NO:6); and (Gly$_4$ Ser)$_4$ (SEQ ID NO:26), although without limitation thereto.

In another embodiment, the linker sequence includes a Plasmin Cleavage Recognition Site, such as according to the sequence:

Leu Ile Lys Met Lys Pro    (SEQ ID NO: 7)

In yet another embodiment, the linker sequence includes a Collagenase-3 Cleavage Recognition Site, such as according to the sequence:

Gln Pro Gln Gly Leu Ala Lys    (SEQ ID NO: 8)

The invention also extends to use of biologically-active fragments of the synthetic chimeric proteins of the invention and/or to use of biologically-active fragments of the particular growth factor receptor-binding domains and integrin binding domains exemplified herein.

In one embodiment, said "biologically-active fragment" has no less than 10%, preferably no less than 25%, more preferably no less than 50% and even more preferably no less than 75, 80, 85, 90 or 95% of a biological activity of a protein from which it is derived.

In another embodiment, said "biologically-active fragment" has no less than 10%, preferably no less than 25%, more preferably no less than 50% and even more preferably no less than 75, 80, 85, 90 or 95% of a contiguous amino acid sequence of a protein from which it is derived.

Specific examples of biologically active fragments of VN, for example lacking a HBD and/or polyanionic domain, are provided herein in FIG. 14.

Also contemplated are variant protein complexes of the invention.

Typically, and in relation to proteins, a "variant" protein has one or more amino acids that have been replaced by different amino acids. It is well understood in the art that some amino acids may be changed to others with broadly similar properties without changing the nature of the activity of the protein (conservative substitutions).

It will be appreciated that one or more amino acid residues of a reference sequence, such as a growth factor, receptor-binding domain of a growth factor, an integrin-binding domain of VN or FN, IGFBPs or one or more corresponding residues present in a synthetic chimeric protein, may be modified or deleted, or additional sequences added, without substantially altering the biological activity of the isolated protein complex of the invention.

Specific mutations in mature VN (SEQ ID NO:2) that are contemplated by the present invention include: (i) T50A; (ii) T57A; (iii) T50E; (iv) T57E; (v) S378E; (vi) S378A; and (v) S362E.

In one embodiment, a protein variant shares at least 70%, preferably at least 80% and more preferably at least 90%, 95%, 98% or 99% sequence identity with a reference amino acid sequence.

Preferably, sequence identify is measured over at least 60%, more preferably over at least 75%, more preferably over at least 90% or more preferably over at least 95%, 98% or substantially the full length of the reference sequence.

In order to determine percent sequence identity, optimal alignment of amino acid and/or nucleotide sequences may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e., resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference.

In another example, "sequence identity" may be understood to mean the "match percentage" calculated by the DNASIS computer program (Version 2.5 for windows; available from Hitachi Software engineering Co., Ltd., South San Francisco, Calif., USA).

A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The invention also contemplates derivatives of a receptor-binding domain of a growth factor, an integrin-binding domain of VN or FN, or an isolated protein complex comprising same.

As used herein, "derivative" proteins of the invention have been altered, for example by addition, conjugation or complexing with other chemical moieties or by post-translational modification techniques as are well understood in the art "Additions" of amino acids may include fusion of the polypeptides or variants thereof with other polypeptides or proteins. The other protein may, by way of example, assist in the purification of the protein. For instance, these include a polyhistidine tag, maltose binding protein, green fluorescent protein (GFP), Protein A or glutathione S-transferase (GST).

Other derivatives contemplated by the invention include, but are not limited to, modification to side chains, incorporation of unnatural amino acids and/or their derivatives during peptide, polypeptide or protein synthesis and the use of crosslinkers and other methods which impose conformational constraints on the polypeptides, fragments and variants of the invention. Examples of side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

Examples of incorporating non-natural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids.

An example of methods suitable for chemical derivatization of proteins is provided in Chapter 15 of CURRENT PROTOCOLS IN PROTEIN SCIENCE Eds. Coligan et. al., John Wiley & Sons NY (1995-2001).

Isolated protein complexes, and individual protein components thereof, (inclusive of fragments, variants, derivatives and homologs) may be prepared by any suitable procedure known to those of skill in the art.

In one embodiment, proteins of the invention are produced by chemical synthesis. Chemical synthesis techniques are well known in the art, although the skilled person may refer to Chapter 18 of CURRENT PROTOCOLS IN PROTEIN SCIENCE Eds. Coligan et. al., John Wiley & Sons NY (1995-2001) for examples of suitable methodology.

In another embodiment, proteins may be prepared as a recombinant protein.

Production of recombinant proteins is well known in the art, the skilled person may refer to standard protocols as for example described in Sambrook et al., MOLECULAR CLONING. A Laboratory Manual (Cold Spring Harbor Press, 1989), incorporated herein by reference, in particular Sections 16 and 17; CURRENT PROTOCOLS IN MOLECULAR BIOLOGY Eds. Ausubel et al., (John Wiley & Sons, Inc. 1995-1999), incorporated herein by reference, in particular Chapters 10 and 16; and CURRENT PROTOCOLS IN PROTEIN SCIENCE Eds. Coligan et al., (John Wiley & Sons, Inc. 1995-1999) which is incorporated by reference herein, in particular Chapters 1, 5 and 6.

In one embodiment, a recombinant protein is produced by a method including the steps of:
  (i) preparing an expression construct which comprises a nucleic acid encoding said protein, operably linked to one or more regulatory nucleotide sequences in an expression vector;
  (ii) transfecting or transforming a host cell with the expression construct; and
  (iii) expressing the recombinant protein in said host cell.

An "expression vector" may be either a self-replicating extra-chromosomal vector such as a plasmid, or a vector that integrates into a host genome.

By "operably linked" or "operably connected" is meant that said regulatory nucleotide sequence(s) is/are positioned relative to the recombinant nucleic acid of the invention to initiate, regulate or otherwise control transcription of the nucleic acid, or translation of a protein encoded by the nucleic acid.

Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, splice donor/acceptor sequences and enhancer or activator sequences.

Constitutive promoters (such as CMV, RSV, adenovirus, SV40 and human elongation factor promoters) and inducible/repressible promoters (such as tet-repressible promoters and IPTG-, metallothionine- or ecdysone-inducible promoters) are well known in the art and are contemplated by the invention. It will also be appreciated that promoters may be hybrid promoters that combine elements of more than one promoter.

The expression construct may also include a fusion partner (typically provided by the expression vector) so that the recombinant protein of the invention is expressed as a fusion polypeptide with said fusion partner. The main advantage of fusion partners is that they assist identification and/or purification of said fusion protein.

Well known examples of fusion partners include, but are not limited to, glutathione-S-transferase (GST), Fc portion of human IgG, maltose binding protein (MBP) and hexahistidine ($HIS_6$), which are particularly useful for isolation of the fusion protein by affinity chromatography. For the purposes of fusion protein purification by affinity chromatography, relevant matrices for affinity chromatography are glutathione-, amylose-, and nickel- or cobalt-conjugated resins respectively. Many such matrices are available in "kit" form, such as the QIAexpress system (Qiagen) useful with ($HIS_6$) fusion partners and the Pharmacia GST purification system.

In some cases, the fusion partners also have protease cleavage sites, such as for Factor $X_a$ or Thrombin, which allow the relevant protease to partially digest the fusion protein of the invention and thereby liberate the recombinant polypeptide of the invention therefrom. The liberated protein can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, haemagglutinin and FLAG tags.

Suitable host cells for expression may be prokaryotic or eukaryotic, such as *Escherichia coli* (DH5α for example), yeast cells, Sf9 cells utilized with a baculovirus expression system, CHO cells, COS, CV-1, NIH 3T3 and 293 cells, although without limitation thereto.

Expression constructs may also include one or more selection marker nucleotide sequences that confer transformed host cell resistance to a selection agent. Selection markers useful for the purposes of selection of transformed bacteria include bla, kanR and tetR while transformed eukaryotic cells may be selected by markers such as hygromycin, G418 and puromycin, although without limitation thereto.

With regard to introducing genetic material into host cells, the terms "transforming" and "transfecting" are used generally to describe introduction of genetic material into a host cell. There are many well known methods for introducing foreign genetic material into a host cell including but not limited to calcium phosphate precipitation, electroporation, delivery by lipofectamine, lipofectin and other lipophilic agents, calcium phosphate precipitation, DEAE-Dextran transfection, microparticle bombardment, microinjection and protoplast fusion.

Isolated Nucleic Acids

The invention provides an isolated nucleic acid that encodes a synthetic chimeric protein of the invention, including variants and homologs thereof.

The term "nucleic acid" as used herein designates single-or double-stranded mRNA, RNA, cRNA, RNAi and DNA inclusive of cDNA and genomic DNA and DNA-RNA hybrids.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

Synthetic nucleic acids of the invention may be produced by chemical synthetic approaches or by recombinant methods that utilize nucleic acid sequence amplification techniques, or a combination thereof, as are well known in the art.

Chemically synthesized primers and oligonucleotides, synthesizers and associated technologies useful according to the present invention are typically available in most laboratories or may be purchased from commercial sources.

Suitable nucleic acid amplification techniques are well known to the skilled addressee, and include polymerase chain reaction (PCR) and ligase chain reaction (LCR) as for example described in Chapter 15 of Ausubel et al. supra; strand displacement amplification (SDA) as for example described in U.S. Pat. No 5,422,252; rolling circle replication (RCR) as for example described in Liu et al., 1996, J. Am. Chem. Soc. 118 1587, International application WO 92/01813 and International Application WO 97/19193; nucleic acid sequence-based amplification (NASBA) as for example described by Sooknanan et al.,1994, Biotechniques 17 1077; and Q-β replicase amplification as for example described by Tyagi et al., 1996, Proc. Natl. Acad. Sci. USA 93 5395, although without limitation thereto.

A preferred nucleic acid sequence amplification technique is PCR. As used herein, an "amplification product" refers to a nucleic acid product generated by a nucleic acid amplification technique.

In producing and expressing nucleic acids of the invention, it will also be appreciated that advantage may be taken with respect to codon sequence redundancy, such that the nucleic acids exemplified herein may be readily modified without changing an amino acid sequence encoded thereby.

In particular embodiments, nucleic acids may be optimized according to preferred "codon usage" of a host cell to be used for recombinant expression, as is well known in the art. This can effectively "tailor" a nucleic acid for optimal expression in a particular organism, or cells thereof, where preferential codon usage affects protein expression.

Therefore, the invention includes synthetic nucleic acids that are homologous to the nucleic acids exemplified herein.

In one embodiment, nucleic acid homologs share at least 70%, preferably at least 80%, more preferably at least 90%, and even more preferably at least 95% sequence identity with a nucleic acid encoding any one of the synthetic chimeric protein constructs described herein.

Preferably, sequence identify is measured over at least 70%, more preferably at least 80%, even more preferably at least 90%, 95% or advantageously over substantially the full length of the encoding nucleic acid of the invention.

In another embodiment, nucleic acid homologs hybridize to a nucleic acid encoding any one of the synthetic chimeric protein constructs described herein under high stringency conditions.

"Hybridize and Hybridization" is used herein to denote the pairing of at least partly complementary nucleotide sequences to produce a DNA-DNA, RNA-RNA or DNA-RNA duplex. Hybridized sequences occur through base-pairing between complementary purines and pyrimidines as is well known in the art.

In this regard, it will be appreciated that modified purines (for example, inosine, methylinosine and methyladenosine) and modified pyrimidines (thiouridine and methylcytosine) may also engage in base pairing.

"Stringency" as used herein, refers to temperature and ionic strength conditions, and presence or absence of certain organic solvents and/or detergents during hybridisation. The higher the stringency, the higher will be the required level of complementarity between hybridizing nucleotide sequences.

"Stringent conditions" designates those conditions under which only nucleic acid having a high frequency of complementary bases will hybridize.

Reference herein to high stringency conditions includes and encompasses:—
  (i) from at least about 31% v/v to at least about 50% v/v formamide and from at least about 0.01 M to at least about 0.15 M salt for hybridisation at 42° C., and at least about 0.01 M to at least about 0.15 M salt for washing at 42° C.;
  (ii) 1% BSA, 1 mM EDTA, 0.5 M NaHPO$_4$ (pH 7.2), 7% SDS for hybridization at 65° C., and (a) 0.1×SSC, 0.1% SDS; or (b) 0.5% BSA, 1mM EDTA, 40 mM NaHPO$_4$ (pH 7.2), 1% SDS for washing at a temperature in excess of 65° C. for about one hour; and
  (iii) 0.2×SSC, 0.1% SDS for washing at or above 68° C. for about 20 minutes.

In general, washing is carried out at $T_m$=69.3 +0.41 (G+C) % −12° C. In general, the $T_m$ of a duplex DNA decreases by about 1° C. with every increase of 1% in the number of mismatched bases.

Notwithstanding the above, stringent conditions are well known in the art, such as described in Chapters 2.9 and 2.10 of. Ausubel et al., supra and in particular at pages 2.9.1 through 2.9.20.

Antibodies

The invention also contemplates antibodies against a synthetic chimeric protein of the invention inclusive of chimeric proteins, or fragments, variants and/or derivatives thereof. Antibodies of the invention may be polyclonal or monoclonal. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. Antibodies: A Laboratory Manual, Cold Spring Harbor, Cold Spring Harbor Laboratory, 1988, which are both herein incorporated by reference.

Generally, antibodies of the invention bind to or conjugate with a polypeptide, fragment, variant or derivative of the invention. For example, the antibodies may comprise polyclonal antibodies. Such antibodies may be prepared for example by injecting a polypeptide, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

In lieu of the polyclonal antisera obtained in the production species, monoclonal antibodies may be produced using the standard method as for example, described in an article by Köhler & Milstein, 1975, Nature 256, 495, which is herein incorporated by reference, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the polypeptides, fragments, variants or derivatives of the invention.

The invention also includes within its scope antibodies which comprise Fc or Fab fragments of the polyclonal or monoclonal antibodies referred to above. Alternatively, the antibodies may comprise single chain Fv antibodies (scFvs) against the BIXP proteins of the invention. Such scFvs may be prepared, for example, in accordance with the methods described respectively in U.S. Pat. No. 5,091,513, European Patent No 239,400 or the article by Winter & Milstein, 1991, Nature 349 293, which are incorporated herein by reference. Labels may be associated with the antibody or antibody fragment.

The label may be selected from a group including a chromogen, a catalyst, an enzyme, a fluorophore, a chemiluminescent molecule, a lanthanide ion such as Europium (Eu$^{34}$), a radioisotope and a direct visual label. In the case of a direct visual label, use may be made of a colloidal metallic or non-metallic particle, a dye particle, an enzyme or a substrate, an organic polymer, a latex particle, a liposome, or other vesicle containing a signal producing substance and the like.

A large number of enzymes useful as labels is disclosed in United States Patent Specifications U.S. Pat. Nos. 4,366,241, 4,843,000, and 4,849,338, all of which are herein incorporated by reference. Enzyme labels useful in the present invention include alkaline phosphatase, horseradish peroxidase, luciferase, b-galactosidase, glucose oxidase, lysozyme, malate dehydrogenase and the like. The enzyme label may be used alone or in combination with a second enzyme in solution.

By way of example, the fluorophore may be fluorescein isothiocyanate (FITC), oregon green, tetramethylrhodamine isothiocyanate (TRITL), allophycocyanin (APC) and R-Phycoerythrin (RPE), although without limitation thereto.

Pharmaceutical Compositions

The invention also provides pharmaceutical compositions that comprise an isolated protein complex of the invention, inclusive of variants and derivatives thereof.

Such isolated protein complex may be in any form inclusive of multi-protein complexes formed in vitro or as synthetic chimeric proteins of the invention, although without limitation thereto.

Pharmaceutical compositions of the invention may be used to promote or otherwise facilitate cell migration, tissue regeneration and wound healing. Alternatively, pharmaceutical compositions may be administered to prevent tumour metastasis by preventing or inhibiting tumour cell migration to a secondary site.

The composition may be used in therapeutic or prophylactic treatments as required. For example, pharmaceutical compositions may be applied in the form of therapeutic or cosmetic preparations for skin repair, wound healing, healing of burns and other dermatological treatments.

In this regard, pharmaceutical compositions may be administered in association with, or as a component of, a biomaterial, biopolymer, inorganic material such as hydroxyapatite or derivates thereof, surgical implant, prosthesis, wound or burn dressing, compress, bandage or the like suitably impregnated, coated or otherwise comprising the pharmaceutical composition.

Suitably, the pharmaceutical composition comprises an appropriate pharmaceutically-acceptable carrier, diluent or excipient.

Preferably, the pharmaceutically-acceptable carrier, diluent or excipient is suitable for administration to mammals, and more preferably, to humans.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

The above compositions may be administered in a manner compatible with the dosage formulation, and in such amount as is pharmacuetically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

With regard to pharmaceutical compositions for wound healing, particular reference is made to U.S. Pat. No. 5,936,064 and International Publication WO99/62536, which are incorporated herein by reference.

Pharmaceutical compositions of the invention may also include expression vectors such as viral vectors such as vaccinia, and viral vectors useful in gene therapy. The latter include adenovirus and adenovirus-associated viruses (AAV) such as described in Braun-Falco et al., 1999, Gene Ther. 6 432, retroviral and lentiviral vectors such as described in Buchshacher et al., 2000, Blood 95 2499 and vectors derived from herpes simplex virus and cytomegalovirus. A general overview of viral vectors useful in endocrine gene therapy is provided in Stone et al., 2000, J. Endocrinol. 164 103.

The present invention may also utilize specific expression vectors which target gene expression to epidermal cells, such as described in U.S. Pat. No. 5,958,764 and for in vivo wound healing applications, such as described in U.S. Pat. No. 5,962,427.

Therapeutic Uses

The invention provides methods of treatment using isolated protein complexes, inclusive of synthetic chimeric proteins of the invention. These methods are particularly aimed at therapeutic and/or prophylactic treatment of mammals, and more particularly, humans.

However, therapeutic uses according to the invention may also be applicable to mammals such as domestic and companion animals, performance animals such as horses, camels and greyhounds, livestock, laboratory animals and animals used as sources of cells, organs and tissues for xenotransplantation.

The invention also contemplates methods of cosmetic treatment where isolated protein complexes inclusive of synthetic chimeric proteins of the invention are administered to improve or enhance skin quality or skin appearance.

Such treatments may include prevention or remedediation of skin disorders such as psoriasis and hypertrophic scarring that result from aberrant skin cell proliferation.

Alternatively, methods of treatment are contemplated whereby tumour metastasis is prevented or inhibited by blocking tumour cell migration to a secondary site. In addition, methods of treating cancer by blocking cell proliferation also contemplated.

In particular embodiments, therapeutic and/or prophylactic treatments may utilize an isolated protein complex, inclusive of synthetic chimeric proteins of the invention, in association with, or as a component of, a biomaterial, biopolymer, inorganic material such as fluorohydroxyapatite, surgical implant, prosthesis, wound or burn dressing, compress, bandage or the like suitably impregnated, coated or otherwise comprising the isolated protein complex.

Such methods include administration of pharmaceutical compositions as hereinbefore defined, and may be by way of microneedle injection into specific tissue sites, such as described in U.S. Pat. No. 6,090,790, topical creams, lotions or sealant dressings applied to wounds, burns or ulcers, such as described in U.S. Pat. No. 6,054,122 or implants which release the composition such as described in International Publication WO99/47070.

Gene therapy is also applicable in this regard, such as according to methods set forth in U.S. Pat. Nos. 5,929,040 and 5,962,427.

There also exist methods by which skin cells can be genetically modified for the purpose of creating skin substitutes, such as by genetically engineering desired growth factor expression (Supp et al., 2000, J. Invest. Dermatol. 114 5). An example of a review of this field is provided in Bevan et al., Biotechnol. Gent. Eng. Rev. 16 231.

Also contemplated is "seeding" a recipient with transfected or transformed cells, such as described in International Publication WO99/11789.

These methods can be used to stimulate cell migration and thereby facilitate or progress wound and burn healing, repair of skin lesions such as ulcers, tissue replacement and grafting such as by in vitro culturing of autologous skin, re-epithelialization of internal organs such as kidney and lung and repair of damaged nerve tissue.

Skin replacement therapy has become well known in the art, and may employ use of co-cultured epithelial/keratinocyte cell lines, for example as described in Kehe et al., 1999, Arch. Dermatol. Res. 291 600 or in vitro culture of primary (usually autologous) epidermal, dermal and/or keratinocyte cells. These techniques may also utilize engineered biomaterials and synthetic polymer "scaffolds".

Examples of reviews of the field in general are provided in Terskikh & Vasiliev, 1999, Int. Rev. Cytol. 188 41 and Eaglestein & Falanga, 1998, Cutis 62 1.

More particularly, the production of replacement oral mucosa useful in craniofacial surgery is described in Izumi et al., 2000, J. Dent. Res. 79 798. Fetal keratinocytes and dermal fibroblasts can be expanded in vitro to produce skin for grafting to treat skin lesions, such as described in Fauza et al., J. Pediatr. Surg. 33 357, while skin substitutes from dermal and epidermal skin elements cultured in vitro on hyaluronic acid-derived biomaterials have been shown to be potentially useful in the treatment of burns (Zacchi et al., 1998, J. Biomed. Mater. Res. 40 187).

Polymer scaffolds are also contemplated for the purpose of facilitating replacement skin engineering, as for example described in Sheridan et al., 2000, J. Control Release 14 91 and Fauza et al., 1998, supra, as are microspheres as agents for the delivery of skin cells to wounds and burns (LaFrance & Armstrong, 1999, Tissue Eng. 5 153).

Production of Agonists and Antagonists

The invention contemplates use of isolated protein complexes inclusive of synthetic chimeric proteins of the invention to identify, screen, design or otherwise produce agonists or antagonists of complexes comprising a growth factor and vitronectin or fibronectin, such as IGF-II:VN, IGF-I:IGFBP:VN, IGF-II:FN or IGF-I:IGFBP:FN complexes. Such agents may be a "mimetic". The term "mimetic" is used herein to refer to molecules that are designed to resemble particular functional regions of proteins or peptides, and includes within its scope the terms "agonist", "analogue" and "antagonist" as are well understood in the art.

In one embodiment, agonists are produced that mimic the binding of the IGF-IR and VN/FN receptors by IGF-II:VN/FN or IGF-I:IGFBP:VN/FN complexes. Such molecules may have utility as stimulators of cell migration such as required for wound healing, skin regeneration and the like.

In another embodiment, antagonists are produced that prevent or inhibit the binding of the IGF-IR and integrin receptors by IGF-II:VN/FN or IGFII:IGFBP:VN/FN complexes. Such molecules may have utility as inhibitors of cell migration and/or cell proliferation and thereby constitute useful anti-tumour agents and also in treatments of skin disorders such as psoriasis and hypertrophic scarring that result from aberrant cell proliferation.

The aforementioned mimetics, agonists, antagonists and analogues may be peptides, polypeptides or other organic molecules, preferably small organic molecules, with a desired biological activity and half-life.

Computer-assisted structural database searching is becoming increasingly utilized as a procedure for identifying mimetics. Database searching methods which, in principle, may be suitable for identifying mimetics, may be found in International Publication WO 94/18232 (directed to producing HIV antigen mimetics), U.S. Pat. No. 5,752,019 and International Publication WO 97/41526 (directed to identifying EPO mimetics), each of which is incorporated herein by reference.

Other methods include a variety of biophysical techniques, which identify molecular interactions. These allow for the screening of candidate molecules according to whether said candidate molecule affects formation of IGF-IGFBP-VN complexes, for example. Methods applicable to potentially useful techniques such as competitive radioligand binding assays (see Upton et al., 1999, supra for a relevant method), analytical ultracentrifugation, microcalorimetry, surface plasmon resonance and optical biosensor-based methods are provided in Chapter 20 of CURRENT PROTOCOLS IN PROTEIN SCIENCE Eds. Coligan et al., (John Wiley & Sons, 1997) which is incorporated herein by reference.

So that the present invention may be more readily understood and put into practical effect, the skilled person is referred to the following non-limiting examples.

EXAMPLES

Example 1

Materials and Methods
Cell Culture

The MCF-7 (ATCC# HTB-22) human breast carcinoma cell line was grown in DMEM/Hams' F12 (DMEM/F12) media (1:1) (Life Technologies, Mulgrave, VIC, Australia) containing 10% FCS. Media was changed daily and cells passaged at 80% confluence using 0.25% trypsin/0.5 mM Ethylenediaminetetra-acetic acid (EDTA) solution (Oxoid, Hampshire, England).

The HaCAT human skin keratinocyte cell line was obtained from Prof. Norbet Fusenig (German Cancer Research Center (DKFZ) Im Neuenheimer Feld, Heidelberg). The HaCAT cell line was grown in DMEM media (Life Technologies) containing 10% FCS. Media was changed daily and cells passaged at 80% confluence using 0.25% trypsin/0.5mM EDTA solution (Oxoid).

Prebinding of IGFs to VN and IGFBPs

Most in vitro assays examining cell function add exogenous factors in solution, hence the cells are bathed in the solution containing the substance throughout the assay. This is not the environment that cells encounter in vivo. Rather, cells in tissues are supported and surrounded by an ECM synthesized by cells, in which hormones and other factors are localized. In this study, which specifically addresses the binding of a growth factor to an ECM molecule, a strategy of pre-binding VN, IGFs and IGFBPs to tissue culture plastic in 24-well plates and to the lower chamber and membrane surface of 12.0 μL pore Costar Transwells™ (Costar, New York, N.Y., USA) was employed in an attempt to more accurately reflect the in vivo environment.

Three hundred microlitres of DMEM or DMEM/F12 media containing 300-1000 ng VN (Promega, Annandale, NSW, Australia) was added to 24-well tissue culture dishes or to the lower chamber of a Transwelff and incubated at 37° C. for 2 hrs. Media containing unbound VN was removed and the wells were washed with 1 mL Hepes Binding Buffer (HBB) containing 0.5% Bovine Serum Albumin (RIA-grade) (BSA) (Sigma Aldrich). Three hundred μL HBB containing 1.0% BSA was then added to wells and incubated at 37° C. for 30 min in order to block non-specific binding sites in the tissue culture dishes. The wells were then washed again with 1 mL HBB containing 0.5% BSA. Three hundred μL HBB containing 0.5% BSA and IGF-II or IGF-I+IGFBP (GroPep, Adelaide, SA, Australia) was then added and the plates incubated again for 2 hrs. The solution containing unbound IGFs and IGFBPs was removed and the wells were washed with HBB and air dried in laminar flow hoods.

Migration Assays

Migration assays were performed essentially as described in Leavesley et al., 1993, Journal of Cell Biology 121:163-70. Fifty thousand cells which had been serum starved by incubation in serum-free media for 4 hours were seeded into the upper chamber of a 12.0 μm pore Costar Transwel™ (12 well plate format). Cells that had migrated to the lower surface of the porous membrane after 5 hrs incubation at 37° C. in 5% $CO_2$, were fixed then stained with Crystal Violet in 0.1 mM Borate Buffer (pH 9). The number of cells attached was estimated by extracting Crystal Violet in 10% acetic acid and determining the absorbance of these extracts via spectrophotometry.

Statistical Analysis

Data was analysed by first expressing all data as a percentage of the negative control (-VN, -IGF, -IGFBP). Responses where then tested for significance versus VN only controls and IGF only controls using a two tailed homoscedastic Student t-test. P values less than 0.05 indicate responses that were significantly different.

Results

Migration

Cell migration is a key process in wound healing and both VN and IGFs have established roles in the mediation of cell migration. In order to dissect the ability of IGF-II bound to VN to alter HaCAT keratinocyte function the migration of cells through Transwells™ was measured.

Figure 1:
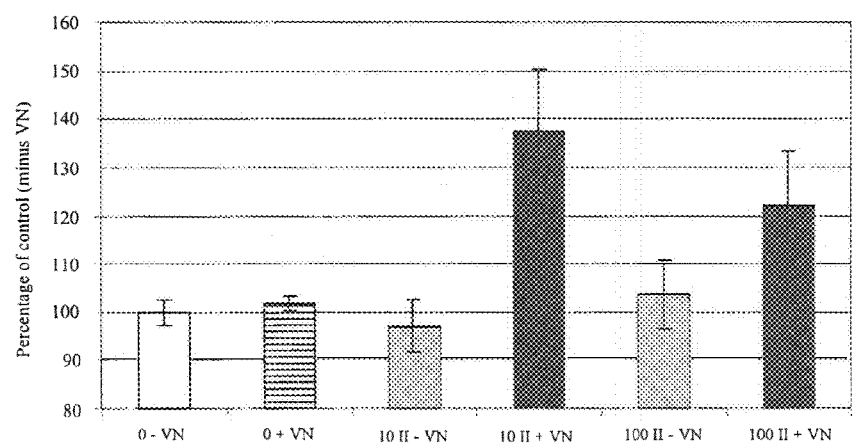

FIG. 1 shows that in the presence of VN there is enhanced IGF-II induced migration of HaCAT human keratinocytes through Transwells™, especially at lower concentrations. Each bar represents data from 3 replicate experiments, with each treatment tested in triplicate.

Figure 2:
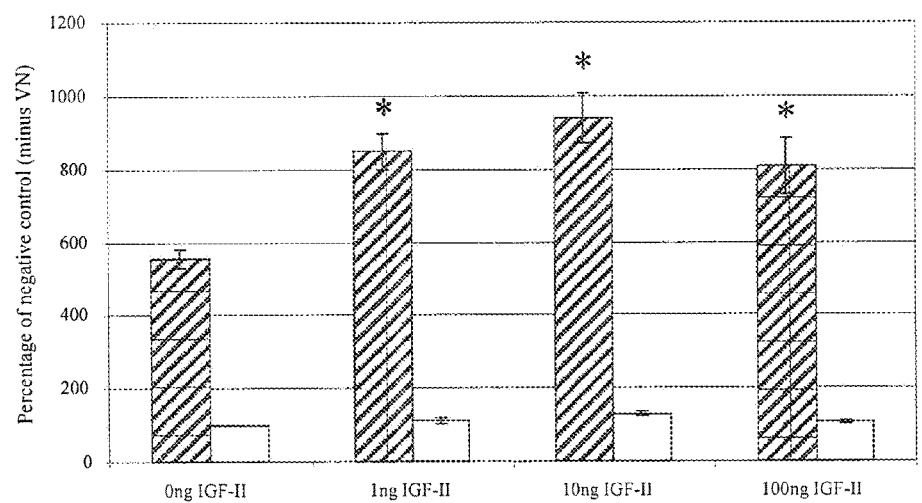

Migration of the breast cancer cell line MCF-7 was also tested. When 1 μg of VN was prebound to the lower well of 12.0 μm Transwells™ a five-fold increase in migration to the lower chamber was observed. "Prebinding" 1-100 ng of IGF-II to the wells in the absence of VN stimulated a two-fold increase in migration. However, when 1-100 ng of IGF-II was prebound to 1 μg VN in the lower chamber, eight to ten fold increases in cell migration were observed (FIG. 2). These responses were significantly higher (p<0.01) than the effects of IGF-II alone and VN alone.

Figure 3:
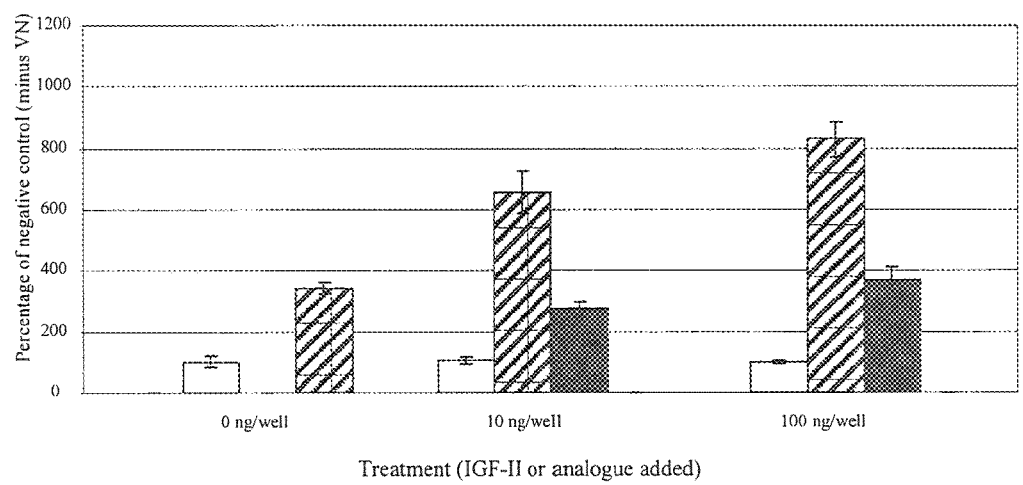

$[L^{27}]$–IGF-II is an IGF-II analogue that does not bind to the IGF-IR; the receptor through which IGF mediated migration is believed to be signaled. Hence, assays examining the ability of $[L^{27}]$–IGF-II prebound to VN to stimulate MCF-7 cell migration through Transwells™ were conducted. These revealed that VN–$[L^{27}]$ IGF-II complexes did not enhance MCF-7 migration beyond the level obtained with VN alone and that the level of migration was significantly less (p<0.01) than that observed in response to IGF-II bound to VN (FIG. 3). These results indicate that the enhanced migration arising from IGF-II bound to VN involves interaction of IGF-II with the IGF-IR.

Figure 4:
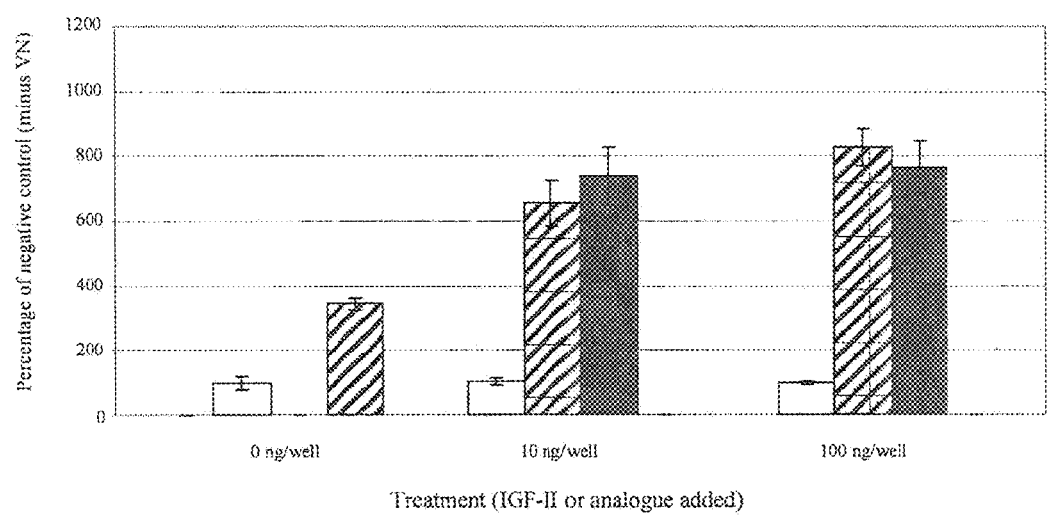

IGFBPs are key regulators of IGF exposure to cells. In order to determine if IGFBPs are involved in the migratory responses to VN:IGF-II complexes observed here, migration assays in MCF-7 cells using an IGF-II analogue that binds poorly to IGFBPs, yet retains affinity for the IGF-IR were conducted. Assays using this IGF-II analogue, des(1-6)–IGF-II, revealed no differences in the migratory responses compared to native IGF-II, suggesting that IGF-II:VN complexes act independently of IGFBPs to enhance cell migration (FIG. 4).

Figure 5:
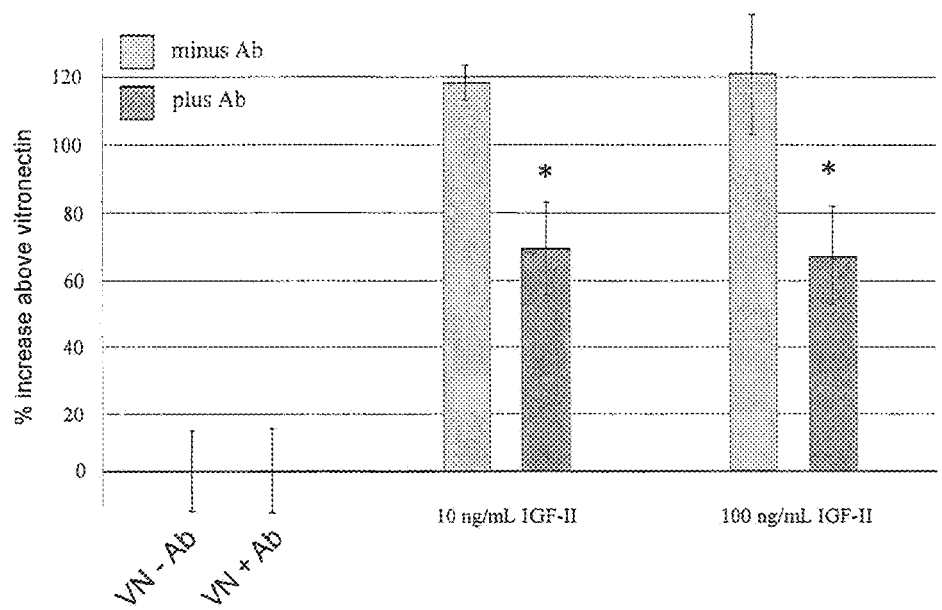

In FIG. 5, the data show that an $\alpha_v$ integrin-blocking antibody substantially reduced MCF-7 cell migration in response to VN and IGF-II complexes. These data indicate that ligation and activation of the $\alpha_v$ integrin receptor for VN appears to be necessary for optimal cell migration in response to IGF-II:VN complexes.

Figure 6:
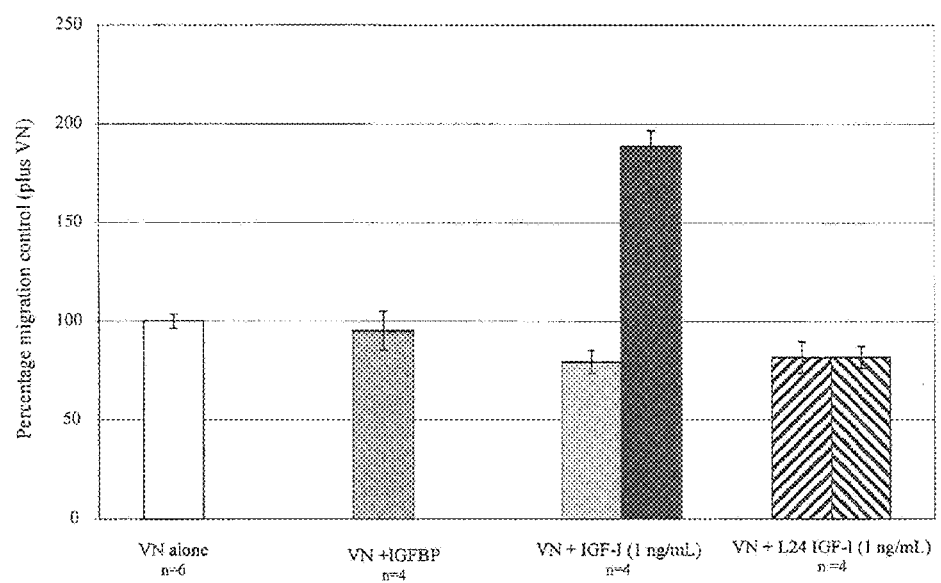

Referring to FIG. 6, in which the IGF-I analogue $L^{24}$-IGF-I that binds poorly to the IGF-IR was examined in MCF-7 cell migration assays, the data demonstrates that:

(1) $L^{24}$–IGF-I and IGF-I have the same effect in the presence of VN but no IGFBP-5; and (2) the presence of IGFBP-5 enhances the migration of cells when IGF-I and VN are present, but not when $L^{24}$–IGF-I and VN are present.

The above data suggest that activation of the IGF-IR is required for the cell migration observed in response to IGF-I:IGFBP:VN complexes and, furthermore, that co-ligation of an integrin receptor for VN is required.

The results of this study reveal for the first time that IGF-II:VN and IGF-I:IGFBP:VN complexes significantly stimulate cell migration. Taken together these data indicate that the VN:IGF complex is functionally relevant to wound healing and may indeed be a significant factor in breast cancer development and progression. Moreover, the enhanced migration involves activation of both the IGF-IR and VN-binding integrin receptors. If indeed, VN:IGF complexes do promote migration and thus metastasis of breast cancer cells, drugs directed at inhibiting VN:IGF complex formation or co-activation of growth factor and integrin receptors may prove to be highly effective therapeutics.

Example 2

Materials and Methods

Purification of Yolk Vitronectin

Yolk vitronectin (VN) was purified using a modification of the method described in Nagano et al., 1992, The Journal of Biological Chemistry 267: 24863-24870. All solutions used in this procedure were pH 7.4. Egg yolk obtained from chicken eggs (Farmland, Coles-Myer, Toowong, QLD, Australia) were suspended in an equal volume of cold Phosphate buffered saline (PBS) (0.16 M NaCl, 10 mM sodium phosphate) containing 2 mM phenylmethanesulfonyl fluoride (PMSF) and centrifuged at 18,000 g at 4° C. for 20 mins. The supernatant (yolk plasma) was dialyzed overnight at 4° C. against 1 mM sodium phosphate containing 5 mM 2-β-mercaptoethanol and centrifuged at 20,000 g at 4° C. for 20 mins. The upper solid layer (low density lipoprotein (LDL) fraction) was recovered and resuspended in 15 ml PBS.

Yolk VN was purified from the LDL fraction using three chromatographic techniques: Gel-filtration, Sepharose CL-6B (Amersham Biosciences, Uppsala, Sweden); Hydroxyapatite HTP (Bio-Rad, Richmond, Calif., USA); Ion exchange, Q Sepharose Fast Flow (Amersham Biosciences).

The Sepharose CL-6B column (10 ml bed volume, column size: 2.5 cm internal diameter (ID)×30 cm) was equilibrated in two steps using (i) PE-buffer (5 mM EDTA, 10 mM sodium phosphate) containing 2 M NaCl and (ii) PE buffer with 0.13 M NaCl. Fifty milliliters of the LDL fraction was diluted 1:1 with PE buffer and applied to the Sepharose CL-6B column, from which the unbound fraction was collected and then applied batchwise to a hydroxyapatite matrix, pre-equilibrated with 10 mM sodium phosphate containing 0.5 M NaCl. The hydroxyapatite was washed with the equilibration buffer followed by 20 ml of 10 mM sodium phosphate. The matrix was then packed into a column (1.5 cm ID×8 cm) and proteins were eluted with 200 mM sodium phosphate collecting 10×5 ml fractions. The eluted fractions were analyzed for the presence of yVN using pre-cast polyacrylamide 4-20% gradient gels (Gradipore, Frenchs Forest, NSW, Australia), SDS-PAGE (Laemmli, 1970) and Coomassie Brilliant Blue (G-250, BioRad) staining. Bio-Rad low range markers were used to determine the molecular weight of the proteins.

Fractions corresponding to the expected molecular weight of yVN (54 kDa) were pooled and dialyzed overnight at 4° C. against 10 mM sodium phosphate and then applied to a Q Sepharose Fast Flow matrix (5 ml bed volume, column size: 1 cm ID×10 cm) pre-equilibrated with 10 mM sodium phosphate. The column was washed with 0.15 M NaCl in 10 mM sodium phosphate and the yVN was eluted with 0.25 M NaCl in 10 mM sodium phosphate. Fractions were again assessed for molecular weight as above.

Preparation of IGF:VN Complexes

IGF:VN complexes were prebound to the 96 well plates and to the Transwells™ as described previously (Kricker et al., 2003, supra.).

Results

FIG. 8 shows the similarity between the full-length (75 kDa) serum VNs (a) and the truncated (54 kDa) yolk VN (b). The main similarities to note is that both these proteins have the RGD cell attachment site and the polyanionic region (the proposed IGF binding site). The main difference to note is that the yolk VN lacks the heparin binding domain.

Figure 9:
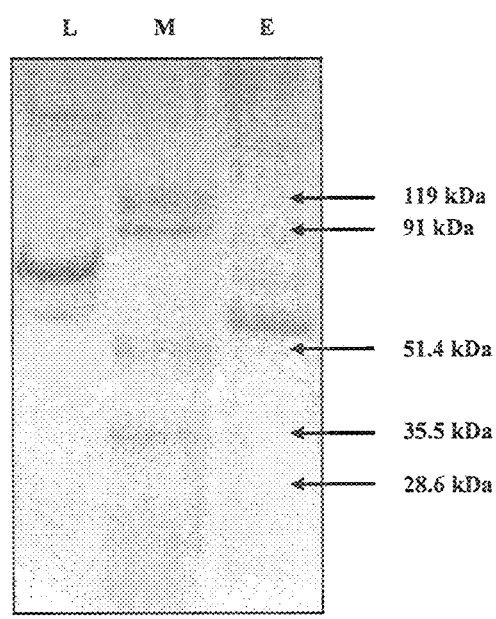

FIG. 9 indicates that the predominate protein present in the elution fraction (lane E) is of the expected size of yolk VN (54 kDa). It is also important to note that this protein was used in the subsequent assays.

Figure 10:
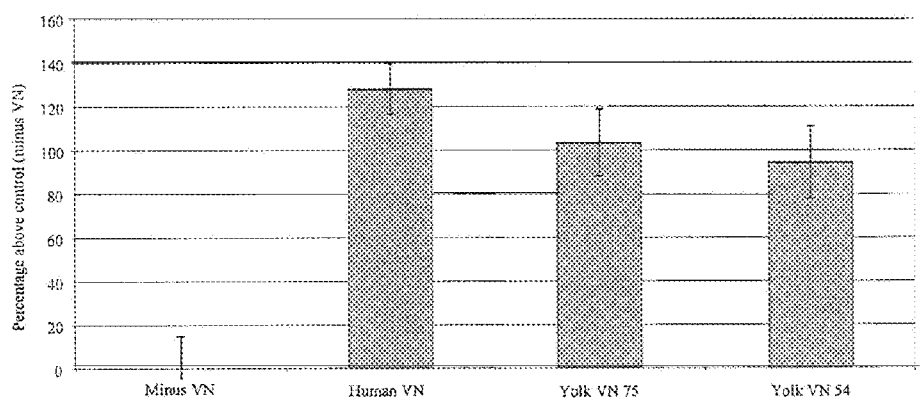

FIG. 10 demonstrates the ability of VNs to bind radiolabelled IGF-I in the presence of IGFBP-3. Therefore, this figure is showing that 54 kD yolk VN has the ability to bind IGF-I/IGFBP-3 at the same level as full-length yolk VN. This suggests that the IGF binding site is not located in the heparin binding domain (which the yolk VN (54 kDa) lacks) and strengthens the polyanionic site as the proposed IGF binding site.

Figure 11:
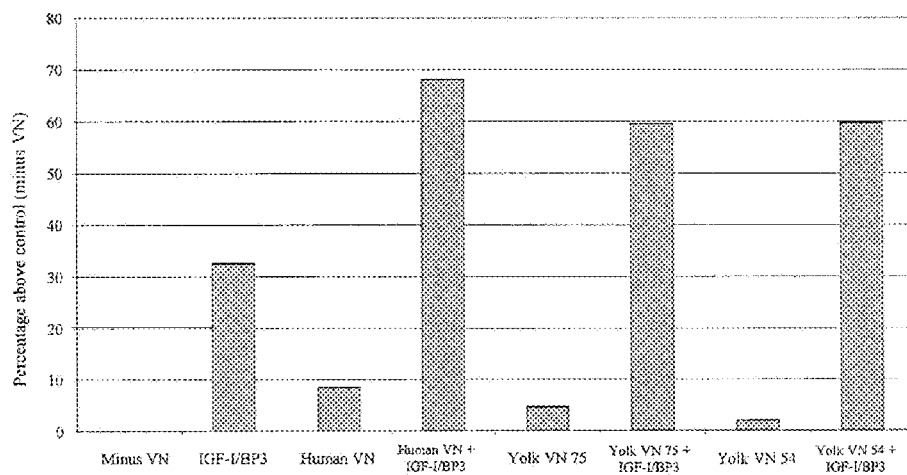

FIG. 11 shows the ability of VN (serum or yolk) when complexed with IGF-I/IFGBP-3 enhances cell proliferation (measured by the MMT technique, assessing mitochondrial dehydrogenase activity) above the controls of no treatment, IGF-I/IGFBP-3 and VN alone. This also indicates that the truncated (54 kDa) yolk VN when complexed with IGF-I/IGFBP-3 can stimulate cell proliferation to the same extent as the full length VNs.

Figure 12:
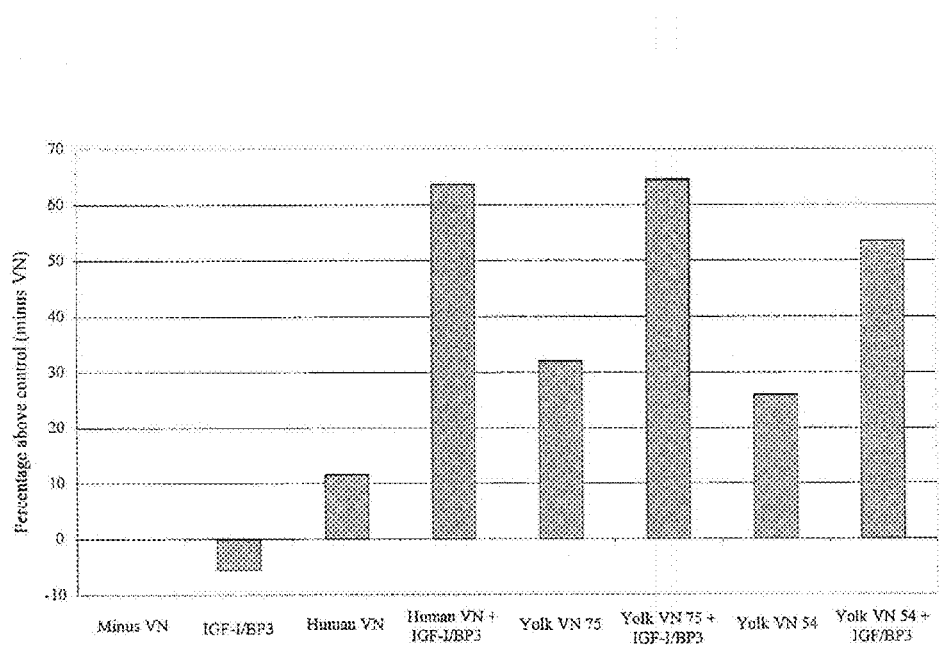

FIG. 12 demonstrates the ability of VN (serum or yolk) when in complex with IGF-I/IGFBP-3 can enhance cell migration (via the Transwell™ migration assay) over the controls of no treatment, IGF-I/IGFBP-3 and VN alone. Therefore, the same conclusions can be drawn from this figure as for FIG. 4, that the truncated (54 kDa) yolk VN when complexed with IGF-I/IGFBP-3 can stimulate cell proliferation to the same extent as the full length VNs. Taken together these figures suggest that the truncated (54 kDa) yolk VN when in complex with IGF-I/IGFBP-3 can stimulate both cell migration and proliferation to similar levels observed to the full-length (75 kDa) VN.

Example 3

Provided herein are proposed examples of synthetic chimeric proteins of the invention, in the form of VN:IGF-I chimeric proteins.

The proposed synthetic chimeric proteins variously set forth in FIG. 14 include any full-length or truncated forms of VN fused with IGF-I, with or without amino acid residue modifications. In addition, the inventors propose fusing VN and IGF-I with or without the various peptide linkers.

Additionally, the present inventors contemplate chimeric proteins comprising VN and growth factors such as VEGF and PDGF, particular embodiments of which are set forth in FIG. 15.

The complete peptide sequences for mature VN (SEQ ID NO:2) and IGF-I (SEQ ID NO:3) used herein and shown in FIG. 13 were obtained from NCBI (accession #NP_0000629 and 1BQT respectively). Annotation of residue numbers given for VN are those of the mature protein and exclude the signal peptide.

With regard to Vitronectin domain structure and Vitronectin ligand binding sites, these are described respectively in FIGS. 7 and 8.

Full-Length and Truncated Forms of VN

One example of a synthetic chimeric protein capable of modulating cell migration contains full-length mature VN and IGF-I proteins.

A) VN(1 . . . 459):IGF-I(1 . . . 70)

Another example capable of modulating cell migration contains the mature VN protein with a deletion of residues 380 to 459 (C-terminal 80 amino acids)

B) VN(1 . . . 379):IGF-I(1 . . . 70)

Monomeric VN in serum exists in two forms: a single chain 75 kDa polypeptide or an endogenously cleaved two chain form of VN consisting of a 65 kDa large fragment linked by a disulfide bond to a 10 kDa smaller fragment. Recent studies have shown that there is no functional difference between these forms suggesting that that the C-terminal 80 amino acids on VN do not confer a functional difference (Gibson and Peterson, 2001, Biochim Biophys Acta 1545 289-304). This is supported by the finding that porcine VN has lost this C-terminal region while retaining its functional activity (Yoneda et al., 1996, J Biochem (Tokyo) 120: 954-60). Thus, we propose a more compact chimeric molecule containing a C-terminal 80 amino acid truncated VN that still confers all functional properties of VN.

Yet another chimera contains only the Somatomedin B domain of VN linked to IGF-I. This region contains the plasminogen activator-1 (PAI-1), urokinase plasminogen activator receptor (uPAR) and integrin binding sites (Schvartz et al., 1999, Int J Biochem Cell Biol 31: 539-44.

This chimera would not interact with components in the ECM such as collagen and glycosaminoglycans. This incorporates a deletion of residues 53 to 459 on VN (connecting region, central beta-propeller domain and heparin binding domain)

C) VN(1 . . . 52):IGF-I(1 . . . 70)

The connecting region of VN has been speculated to play roles in binding the thrombin-antithrombin complex as well as the ECM component collagen. The chimera proposed here contains the Somatomedin B domain of VN as well as the connecting region created by deletion of residues 131 to 459 on VN (central beta-propeller domain and heparin binding domain).

D) VN (1 . . . 130):IGF-I(1 . . . 70)

In a further example the central domain on VN is the largest, but least well characterised domain of the protein in terms of function. However, it is speculated that the beta-propeller structure observed in this domain may be responsible for the multimerisation of VN (Xu et al., 2001, Proteins 44: 312-20.

We propose the deletion of this domain to result in a smaller chimera that retains the ligand binding regions within the Somatomedin B domain, polyanionic connecting region and polycationic heparin binding domain (HBD) of VN that would, however, be unable to self associate. This involves a deletion of residues 131 to 346 on VN (central beta-propeller domain).

E) VN(1 . . . 130,347-459):IGF-I(1 . . . 70)

Still yet another chimera consists of the most compact form of VN we believe capable of binding its extracellular ligands. The protein has both the central domain and the C-terminal 80 amino acids of VN removed. This requires a deletion of residues 131 to 346 and 380 to 459 on VN (central beta-propeller domain and C-terminal 80 amino acids respectively)

F) VN(1 . . . 130,347-379):IGF-I(1 . . . 70)

A further example of a chimera contains a C-terminal truncated VN without the heparin-binding domain. Thus the protein contains the Somatomedin B domain, connecting region and central beta-propeller domain of VN. Although putative secondary heparin binding sites have been proposed for VN within the central beta-propeller domain of VN, Gibson and others (Gibson et al., 1999, J Biol Chem 274 6432-42) demonstrated that these are not functional and that the heparin binding domain is responsible for total glycosaminoglycan binding activity. Thus, the chimera would not interact with heparin and heparan sulfates. This chimera has a deletion of residues 347 to 459 on VN (heparin binding domain).

G) VN(1 . . . 346):IGF-I(1 . . . 70)

Residue Modifications on VN AND IGF-I

VN can be phosphorylated by casein kinase II (CK2) at residues $T^{50}$ and $T^{57}$ to promote cell adhesion and spreading. While both CK2-phosphorlated and CK2-non-phosphorylated analogues of VN (simulated by VN mutants (T50E, T57E) and (T50A,T57A) respectively) bind $\alpha v\beta 3$ and $\alpha v\beta 5$ integrins to activate the ERK signalling pathway, only the CK2-phosphorlated analogue of VN specifically binding the $\alpha v\beta 3$ integrin activated the phosphatidylinositol 3 kinase (PI3-K) pathway (Seger et al., 1998,. J Biol Chem 273: 24805-13; Seger et al., 2001, J Biol Chem 276: 16998-7006).

It is this PI3-K pathway activation that presumably leads to increased cell adhesion and spreading. We therefore propose chimeras with mutations that would either promote or inhibit the activation of the PI3-K pathway following binding to the $\alpha v\beta 3$ integrin. Thus, a chimeric molecule with the T50A and T57A substitutions on VN would be analogous to the CK2-non phosphorylated VN and be restricted to signalling through the ERK pathway (H) whereas synthetic constructs with the T5OE and T57E substitutions on VN would mimic the CK2-phosphorylated VN and be capable of activating both the ERK and PI3-K pathway leading to altered intracellular signalling (I).

H) VN(T50A,T57A):IGF-I

I) VN(T50E,T57E):IGF-I

There is a cAMP-dependant protein kinase (PKA) phosphorylation site at residue $S^{378}$ on VN. It has been demonstrated with PKA-phosphorylated and PKA-non phosphorylated VN analogues (simulated by VN mutants S378E and S378A respectively) that phosphorylation of this site reduces the binding of PAI-1 to VN and thus modulate VN role in the urokinase system (Schvartz et al., 2002, Arch Biochem Biophys 397: 246-52.

We therefore propose chimeras containing both the S378E mutation on VN to inhibit PAI-1 binding by the chimera (J) and the S378A mutation on VN to promote PAI-1 binding and stabilisation within the chimeric protein (K). Furthermore, a S378A mutation may enhance cell migration as PAI-1 binding to VN has been shown to inhibit integrin-mediated cell migration (Kjoller et al., 1997, Exp Cell Res 232: 420-9) and uPAR- and integrin-mediated cell adhesion on VN (Deng et al., 2001, J Cell Physiol 189 23-33. Interestingly these findings were observed independently of PAI-1's function as an inhibitor of plasminogen activation.

J) VN(S378E):IGF-I

K) VN(S378A):IGF-I

Gechtman and Shaltiel, 1997, Eur J Biochem 243 493-501, have shown that protein kinase C (PKC) can phosphorylate VN at residue $S^{362}$. This phosphorylation attenuates the plasmin cleavage of VN which occurs within the heparin binding domain of VN. Thus plasmin cleavage at this site modulates the affinity of VN for its ligands that bind within this region and also modulates the half-life of VN. We therefore propose introducing a S362E substitution to mimic the phosphorylated serine and to consequently inhibit the chimera's cleavage by plasmin.

L) VN (S362E):IGF-I

IGFBPs have been shown to require the N-terminal 3 residues on IGF-I for binding this growth factor with high affinity (Tomas et al., 1991, J Endocrinol 128: 97-105.

It therefore appears unlikely that IGF-I linked to VN through its N-terminal sequence could bind IGFBPs. Despite this, we further propose a VN:IGF-I chimera containing an N-terminal-truncated IGF-I to eliminate all chance that IGFBPs could bind to IGF-I and consequently inhibit the biological activity of the VN:IGF-I chimeric protein. This construct includes a deletion of residues 1 to 3 on IGF-I (IGFBP binding region).

M) VN:IGF-I(4 . . . 70)

It has been suggested that the polyanionic region of VN is responsible for binding IGF-II and IGFBPs. We therefore propose yet another VN:IGF-I chimera that has the polyanionic domain removed from VN. This chimera may therefore be unable to IGF-II or IGFBPs.

N) VN (1 . . . 52, 65 . . . 459) IGF-I (1 . . . 70)

Fusing VN to IGF-I

We propose that VN and IGF-I cDNA can be fused together prior to expression with or without the insertion of a peptide linker sequence. Various linker sequences have been used successfully to fuse proteins, usually consisting of combinations of glycine and serine residues and/or protease cleavage sites such as for thrombin, collagenase or plasmin.

Non-limiting examples of linker sequences are

```
  (i)  Gly4 Ser;                      (SEQ ID NO: 4)

(ii)  Gly4 Ser3;                     (SEQ ID NO: 5)

(iii)  (Gly4 Ser)3;                   (SEQ ID NO: 6)

(iv)  Leu Ile Lys Met Lys Pro;       (SEQ ID NO: 7)
and (v)  Gln Pro Gln Gly Leu Ala Lys.  (SEQ ID NO: 8)
```

Fusion of VN to other Peptide Growth Factors

In addition to fusing the extracellular matrix protein, VN, with the growth factor, IGF-I, we propose the fusion of VN with other peptide growth factors. Specifically, we propose the development of the following chimeric proteins (FIG. 16).

A) VN:PDGFa(1 . . . 210) (NCBI accession #PO4085)
B) VN:VEGF(1 . . . 102) (NCBI accession #2VPFE)

We propose that respective cell surface receptors interact with integrins, and in particular, the VN receptor, the αvβ3 integrin. Specifically, it has been shown that the PDGF receptor co-immunoprecipitates with the αvβ3 integrin following stimulation with PDGF (Schneller et al., EMBO J 16: 5600-7.

It has also been demonstrated that the VEGF receptor type 2 co-immunoprecipitates with the VN receptor following stimulation with its growth factor (Soldi et al., EMBO J 18: 882-92).

The findings that the receptors for these growth factors interact with the αvβ3 integrin suggest that there is an important role for this interaction in modulating/potentiating the intracellular signalling pathways of these cell surface receptors. Therefore, the co-activation and association of these receptors initiated by the above chimeric proteins may induce profound biological responses relevant to therapeutic applications.

Example 4

IGF-I, IGFBPs and FN Stimulate Cell Migration

MCF-10A cells were seeded onto Transwells that had been coated with FN (1 μg/mL) and increasing concentrations of IGF-I prebound in the presence of IGFBP-3 or -5. The cells where allowed to migrate for 5 hours. The number of cells traversing the membrane in response to each treatment was then expressed as a percentage of those that migrated on FN only (SFM). MCF-10 data are pooled from three experiments with treatments tested in four wells in each replicate experiment and shown in FIG. 17. Error bars indicate SEM. SFM=Serum-free media. IGF-I:FN, IGF-I:IGFBP-3:FN and IGF-I:IGFBP-5:FN were able to stimulate significantly increased migration above that of FN alone control wells (responses of 153.7+/−7.3%, 192.5+/−6.8% and 187.5+/−6.5% of the FN control wells, respectively) ($p<0.05$). The response of the MCF7-10A cells to IGF-I:IGFBP-3:FN and IGF-I:IGFBP-5:FN treatments was also significantly greater than those obtained with either IGFBP or IGF-I alone with FN ($p<0.05$). This data indicates that as was found with IGF-I:IGFBP-3/5:VN complexes, maximal responses occur when the trimeric IGF-I:IGFBP-3/5:FN complexes are present. This suggests that chimeras containing IGF-I linked to FN are likely to activate the FN binding integrins and the cognate growth factor receptor in a similar manner to that proposed for VN:growth factor chimeras.

Example 5

EGF, bFGF and KGF VN Chimeras Stimulate Cell Migration and Proliferation

Isolated human keratinocyte and fibroblast cells (P1 and P3 respectively) were applied to the inner chamber of a seeding ring in culture wells pre-treated with varying doses of VN:EGF, VN:bFGF and VN:KGF chimeras, and controls. After a 4-hour period of attachment, the seeding ring was removed and cells were allowed to migrate outward in response to the pre-bound treatments over a period of 24 hours for keratinocytes and 48 hours for fibroblasts. Cell assay data were pooled from at least 3 separate experiments, each with triplicate independent tests with results expressed as percentage above SG/SFM (negative control) and shown in FIG. 19 and FIG. 20. Error bars indicate SEM. SG=Stripped Greens media, SFM=Serum-free media (both are negative controls). With reference to experiments utilizing isolated human skin keratinocytes, each chimera demonstrated functional equivalence to equimolar combinations of individual components, indicating proper protein expression, purification and processing. Furthermore, VN:EGF chimeric treatments at 50 nM and 150 nM promoted significantly (p=<0.05) enhanced responses compared to the VN alone control whilst acting to a similar efficacy as the tetrameric VN:IGFBP-3:IGF-I:EGF complex. Experiments testing the response of isolated skin fibroblasts indicated that all three chimeras induced cell migration significantly (p=<0.05) above equimolar combinations of individual components, whilst treatments of VN:EGF 150 nM, VN:bFGF 15 nM and 50 nM generated significant increases in migration compared to the highest dose of tetrameric VN:IGFBP-3:IGF-I:EGF complex.

In order to assess the proliferation inducing potential of the VN:growth factor chimeras, isolated human keratinocyte and fibroblast cells (P1 and P3 respectively) were seeded into wells pre-treated with varying doses of VN:EGF, VN:bFGF and VN:KGF chimeras, and controls at a density of 15,000 cells/$cm^2$. The cells were allowed to proliferate over 72 and 48 hours for keratinocytes and fibroblasts respectively after which the culture media was removed and the culture plates snap frozen at −80° C. Upon thawing of the plates, a mixture of cell lysis and GR-dye (Invitrogen, CYQUANT kit) was added to each well and incubated at room temperature for 5 minutes. The plates were then interrogated for fluorescence by excitation at 485 nm and absorbance was read at 520 nm. Cell assay data were pooled from at least 3 separate experiments, each with triplicate independent tests with results expressed as percentage above SG/SFM (negative control) and shown in FIG. 21 and FIG. 22. Error bars indicate SEM. SG=Stripped Greens media, SFM=Serum-free media (both are negative controls). Experiments testing proliferation in isolated human skin keratinocytes demonstrated that the VN:bFGF and VN:KGF chimeras functioned in equivalence to equimolar combinations of individual components (VN+bFGF and VN+KGF). Proliferation experiments utilising isolated skin fibroblasts indicated that all three chimeras (VN:EGF 50 nM, 150 nM, VN:bFGF 50 nM, 150 nM and VN:KGF 150 nM) induced cell proliferation significantly (p=<0.05) above equimolar combinations of individual components and tetrameric VN:IGFBP-3:IGF-I:EGF complex.

Throughout the specification, the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein are incorporated herein by reference.

---

Having described the invention, the following is claimed:

1. An isolated protein complex in the form of a synthetic chimeric protein, comprising an amino acid sequence of:
   (i) a growth factor selected from epidermal growth factor (EGF), basic fibroblast growth factor (bFGF) and keratinocyte growth factor (KGF), or at least a domain of said growth factor which is capable of binding a cognate growth factor receptor; and
   (ii) vitronectin (VN) or a fragment of VN comprising at least an integrin-binding domain, wherein said at least an integrin-binding domain comprises the sequence RGD and facilitates cell attachment.

2. The isolated protein complex of claim 1, wherein said VN or said fragment of VN comprising at least an integrin-binding domain does not comprise a heparin-binding domain (HBD).

3. The isolated protein complex of claim 1, wherein the integrin-binding domain is an $\alpha_v$ integrin-binding domain.

4. The isolated protein complex of claim 3, wherein the integrin-binding domain is an $\alpha_v\beta_3$ integrin-binding domain or an $\alpha_v\beta_5$ integrin-binding domain.

5. The isolated protein complex of claim 1, wherein said VN or said fragment of VN comprising at least an integrin-binding domain of VN does not comprise a polyanionic amino acid sequence corresponding to residues 53-64 of a mature VN protein (SEQ ID NO:2).

6. The isolated protein complex of claim 1, comprising amino acids 1-459 of a mature VN sequence (SEQ ID NO:2).

7. The isolated protein complex of claim 1, wherein the fragment of VN comprises amino acids 1-311 of a mature VN sequence (SEQ ID NO:2).

8. The isolated protein complex of claim 1, wherein the fragment of VN comprises amino acids 1-125 of a mature VN sequence (SEQ ID NO:2).

9. The isolated protein complex of claim 1, wherein the fragment of VN comprises amino acids 1-64 of a mature VN sequence (SEQ ID NO:2).

10. The isolated protein complex of claim 1, wherein the fragment of VN comprises amino acids 1-52 of a mature VN sequence (SEQ ID NO:2).

11. The isolated protein complex of claim 1, which does not comprise an IGFBP amino acid sequence.

12. The isolated protein complex of claim 1, further comprising at least one linker sequence.

13. The isolated protein complex of claim 12, wherein the linker sequence comprises a protease cleavage site.

14. The isolated protein complex of claim 12, wherein the linker sequence is selected from the group consisting of:

(i) Gly$_4$ Ser; (SEQ ID NO: 4)
   (ii) Gly$_4$ Ser$_3$; (SEQ ID NO: 5)
   (iii) (Gly$_4$ Ser)$_3$; (SEQ ID NO: 6)
   (iv) (Gly$_4$ Ser)$_4$; (SEQ ID NO: 26)
   (v) Leu Ile Lys Met Lys Pro; (SEQ ID NO: 7) and
   (vi) Gln Pro Gln Gly Leu Ala Lys. (SEQ ID NO: 8)

15. The isolated protein complex of claim 1, wherein said synthetic chimeric protein comprises an amino acid sequence selected from the group consisting of:
   (i) 1-64 VN:(Gly$_4$ Ser)$_4$:1-53 EGF:Gly$_4$ Ser Gly$_4$:6 His (SEQ ID NO:27);
   (ii) 1-64 VN:(Gly$_4$ Ser)$_4$:1-146 bFGF:Gly$_4$ Ser Gly$_4$:6 His (SEQ ID NO:28); and
   (iii) 1-64 VN:(Gly$_4$ Ser)$_4$:1-163 KGF:Gly$_4$ Ser Gly$_4$:6 His (SEQ ID NO:29).

16. An isolated nucleic acid encoding the isolated protein complex of claim 1.

17. A genetic construct, comprising the isolated nucleic acid of claim 16 operably linked to one or more regulatory nucleotide sequences in a vector.

18. The genetic construct of claim 17, which is an expression construct, wherein the isolated nucleic acid is operably linked to a promoter.

19. An isolated host cell, comprising the genetic construct of claim 17.

20. A pharmaceutical composition, comprising the isolated protein complex of claim 1 and a pharmaceutically-acceptable carrier, diluent or excipient.

21. A surgical implant, scaffold or prosthesis impregnated, coated or otherwise comprising the isolated protein complex of claim 1.

22. A wound or burn dressing, comprising the isolated protein complex of claim 1.

23. A method of treating dermatological wounds, including the step of using the isolated protein complex of claim 1 to bind both a growth factor receptor and an integrin receptor expressed by a cell to thereby induce, augment or otherwise promote migration and/or proliferation of an epithelial cell.

24. The method of claim 23, wherein the isolated protein complex is administered to an animal to promote cell migration and/or proliferation in situ.

25. The method of claim 24, wherein the animal is a human.

26. The method of claim 23, wherein the isolated protein complex is administered to one or more cells or tissues in vitro.

* * * * *

SEQUENCE LISTING

<160> NUMBER OF SEQ ID NOS: 29

<210> SEQ ID NO 1
<211> LENGTH: 478
<212> TYPE: PRT
<213> ORGANISM: Homo sapiens

<400> SEQUENCE: 1

```
Met Ala Pro Leu Arg Pro Leu Leu Ile Leu Ala Leu Leu Ala Trp Val
1               5                   10                  15

Ala Leu Ala Asp Gln Glu Ser Cys Lys Gly Arg Cys Thr Glu Gly Phe
            20                  25                  30

Asn Val Asp Lys Lys Cys Gln Cys Asp Glu Leu Cys Ser Tyr Tyr Gln
        35                  40                  45

Ser Cys Cys Thr Asp Tyr Thr Ala Glu Cys Lys Pro Gln Val Thr Arg
    50                  55                  60

Gly Asp Val Phe Thr Met Pro Glu Asp Glu Tyr Thr Val Tyr Asp Asp
65                  70                  75                  80

Gly Glu Glu Lys Asn Asn Ala Thr Val His Glu Gln Val Gly Gly Pro
                85                  90                  95

Ser Leu Thr Ser Asp Leu Gln Ala Gln Ser Lys Gly Asn Pro Glu Gln
            100                 105                 110

Thr Pro Val Leu Lys Pro Glu Glu Glu Ala Pro Ala Pro Glu Val Gly
        115                 120                 125

Ala Ser Lys Pro Glu Gly Ile Asp Ser Arg Pro Glu Thr Leu His Pro
    130                 135                 140

Gly Arg Pro Gln Pro Pro Ala Glu Glu Glu Leu Cys Ser Gly Lys Pro
145                 150                 155                 160

Phe Asp Ala Phe Thr Asp Leu Lys Asn Gly Ser Leu Phe Ala Phe Arg
                165                 170                 175

Gly Gln Tyr Cys Tyr Glu Leu Asp Glu Lys Ala Val Arg Pro Gly Tyr
            180                 185                 190

Pro Lys Leu Ile Arg Asp Val Trp Gly Ile Glu Gly Pro Ile Asp Ala
        195                 200                 205

Ala Phe Thr Arg Ile Asn Cys Gln Gly Lys Thr Tyr Leu Phe Lys Gly
    210                 215                 220

Ser Gln Tyr Trp Arg Phe Glu Asp Gly Val Leu Asp Pro Asp Tyr Pro
225                 230                 235                 240

Arg Asn Ile Ser Asp Gly Phe Asp Gly Ile Pro Asp Asn Val Asp Ala
                245                 250                 255

Ala Leu Ala Leu Pro Ala His Ser Tyr Ser Gly Arg Glu Arg Val Tyr
            260                 265                 270

Phe Phe Lys Gly Lys Gln Tyr Trp Glu Tyr Gln Phe Gln His Gln Pro
        275                 280                 285

Ser Gln Glu Glu Cys Glu Gly Ser Ser Leu Ser Ala Val Phe Glu His
    290                 295                 300

Phe Ala Met Met Gln Arg Asp Ser Trp Glu Asp Ile Phe Glu Leu Leu
305                 310                 315                 320

Phe Trp Gly Arg Thr Ser Ala Gly Thr Arg Gln Pro Gln Phe Ile Ser
                325                 330                 335

Arg Asp Trp His Gly Val Pro Gly Gln Val Asp Ala Ala Met Ala Gly
```

```
                340                 345                 350
Arg Ile Tyr Ile Ser Gly Met Ala Pro Arg Pro Ser Leu Ala Lys Lys
            355                 360                 365

Gln Arg Phe Arg His Arg Asn Arg Lys Gly Tyr Arg Ser Gln Arg Gly
        370                 375                 380

His Ser Arg Gly Arg Asn Gln Asn Ser Arg Arg Pro Ser Arg Ala Met
385                 390                 395                 400

Trp Leu Ser Leu Phe Ser Ser Glu Glu Ser Asn Leu Gly Ala Asn Asn
                405                 410                 415

Tyr Asp Asp Tyr Arg Met Asp Trp Leu Val Pro Ala Thr Cys Glu Pro
            420                 425                 430

Ile Gln Ser Val Phe Phe Ser Gly Asp Lys Tyr Tyr Arg Val Asn
        435                 440                 445

Leu Arg Thr Arg Arg Val Asp Thr Val Asp Pro Tyr Pro Arg Ser
    450                 455                 460

Ile Ala Gln Tyr Trp Leu Gly Cys Pro Ala Pro Gly His Leu
465                 470                 475

<210> SEQ ID NO 2
<211> LENGTH: 459
<212> TYPE: PRT
<213> ORGANISM: Homo sapiens

<400> SEQUENCE: 2

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
    210                 215                 220

Ser Asp Gly Phe Asp Gly Ile Pro Asp Asn Val Asp Ala Ala Leu Ala
225                 230                 235                 240
```

Leu Pro Ala His Ser Tyr Ser Gly Arg Glu Arg Val Tyr Phe Phe Lys
            245                 250                 255

Gly Lys Gln Tyr Trp Glu Tyr Gln Phe Gln His Gln Pro Ser Gln Glu
        260                 265                 270

Glu Cys Glu Gly Ser Ser Leu Ser Ala Val Phe Glu His Phe Ala Met
            275                 280                 285

Met Gln Arg Asp Ser Trp Glu Asp Ile Phe Glu Leu Leu Phe Trp Gly
        290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                325                 330                 335

Ile Ser Gly Met Ala Pro Arg Pro Ser Leu Ala Lys Lys Gln Arg Phe
            340                 345                 350

Arg His Arg Asn Arg Lys Gly Tyr Arg Ser Gln Arg Gly His Ser Arg
        355                 360                 365

Gly Arg Asn Gln Asn Ser Arg Arg Pro Ser Arg Ala Thr Trp Leu Ser
370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                405                 410                 415

Val Phe Phe Phe Ser Gly Asp Lys Tyr Tyr Arg Val Asn Leu Arg Thr
            420                 425                 430

Arg Arg Val Asp Thr Val Asp Pro Pro Tyr Pro Arg Ser Ile Ala Gln
        435                 440                 445

Tyr Trp Leu Gly Cys Pro Ala Pro Gly His Leu
450                 455

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 4
<211> LENGTH: 5
<212> TYPE: PRT
<213> ORGANISM: Artificial sequence
<220> FEATURE:
<223> OTHER INFORMATION: Synthetic linker

<400> SEQUENCE: 4

Gly Gly Gly Gly Ser
1               5

-continued

```
<210> SEQ ID NO 5
<211> LENGTH: 7
<212> TYPE: PRT
<213> ORGANISM: Artificial sequence
<220> FEATURE:
<223> OTHER INFORMATION: Synthetic linker

<400> SEQUENCE: 5

Gly Gly Gly Gly Ser Ser Ser
1               5

<210> SEQ ID NO 6
<211> LENGTH: 15
<212> TYPE: PRT
<213> ORGANISM: Artificial sequence
<220> FEATURE:
<223> OTHER INFORMATION: Synthetic linker

<400> SEQUENCE: 6

Gly Gly Gly Gly Ser Gly Gly Gly Ser Gly Gly Gly Gly Ser
1               5                   10                  15

<210> SEQ ID NO 7
<211> LENGTH: 6
<212> TYPE: PRT
<213> ORGANISM: Artificial sequence
<220> FEATURE:
<223> OTHER INFORMATION: Synthetic linker with protease cleavage site

<400> SEQUENCE: 7

Leu Ile Lys Met Lys Pro
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic linker with protease cleavage site

<400> SEQUENCE: 8

Gln Pro Gln Gly Leu Ala Lys
1               5

<210> SEQ ID NO 9
<211> LENGTH: 529
<212> TYPE: PRT
<213> ORGANISM: Artificial sequence
<220> FEATURE:
<223> OTHER INFORMATION: Chimeric sequence
<220> FEATURE:
<221> NAME/KEY: Linker
<222> LOCATION: (459)..(460)

<400> SEQUENCE: 9

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
        50                  55                  60

Lys Asn Asn Ala Thr Val His Glu Gln Val Gly Gly Pro Ser Leu Thr
65                  70                  75                  80
```

```
Ser Asp Leu Gln Ala Gln Ser Lys Gly Asn Pro Glu Gln Thr Pro Val
                85                  90                  95

Leu Lys Pro Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
            115                 120                 125

Gln Pro Pro Ala Glu Glu Leu Cys Ser Gly Lys Pro Phe Asp Ala
            130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
                180                 185                 190

Arg Ile Asn Cys Gln Gly Lys Thr Tyr Leu Phe Lys Gly Ser Gln Tyr
                195                 200                 205

Trp Arg Phe Glu Asp Gly Val Leu Asp Pro Asp Tyr Pro Arg Asn Ile
            210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
                260                 265                 270

Glu Cys Glu Gly Ser Ser Leu Ser Ala Val Phe Glu His Phe Ala Met
            275                 280                 285

Met Gln Arg Asp Ser Trp Glu Asp Ile Phe Glu Leu Leu Phe Trp Gly
            290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                325                 330                 335

Ile Ser Gly Met Ala Pro Arg Pro Ser Leu Ala Lys Lys Gln Arg Phe
                340                 345                 350

Arg His Arg Asn Arg Lys Gly Tyr Arg Ser Gln Arg Gly His Ser Arg
            355                 360                 365

Gly Arg Asn Gln Asn Ser Arg Arg Pro Ser Arg Ala Thr Trp Leu Ser
            370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                405                 410                 415

Val Phe Phe Phe Ser Gly Asp Lys Tyr Tyr Arg Val Asn Leu Arg Thr
                420                 425                 430

Arg Arg Val Asp Thr Val Asp Pro Pro Tyr Pro Arg Ser Ile Ala Gln
            435                 440                 445

Tyr Trp Leu Gly Cys Pro Ala Pro Gly His Leu Gly Pro Glu Thr Leu
            450                 455                 460

Cys Gly Ala Glu Leu Val Asp Ala Leu Gln Phe Val Cys Gly Asp Arg
465                 470                 475                 480

Gly Phe Tyr Phe Asn Lys Pro Thr Gly Tyr Gly Ser Ser Ser Arg Arg
                485                 490                 495

Ala Pro Gln Thr Gly Ile Val Asp Glu Cys Cys Phe Arg Ser Cys Asp
```

-continued

```
                        500                 505                 510

Leu Arg Arg Leu Glu Met Tyr Cys Ala Pro Leu Lys Pro Ala Lys Ser
            515                 520                 525

Ala

<210> SEQ ID NO 10
<211> LENGTH: 449
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (379)..(380)

<400> SEQUENCE: 10

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Tyr Pro Arg Asn Ile
    210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
        275                 280                 285

Met Gln Arg Asp Ser Trp Glu Asp Ile Phe Glu Leu Leu Phe Trp Gly
    290                 295                 300

Arg Thr Ser Ala Gly Thr Arg Gln Pro Gln Phe Ile Ser Arg Asp Trp
305                 310                 315                 320
```

```
His Gly Val Pro Gly Gln Val Asp Ala Ala Met Ala Gly Arg Ile Tyr
            325                 330                 335

Ile Ser Gly Met Ala Pro Arg Pro Ser Leu Ala Lys Lys Gln Arg Phe
        340                 345                 350

Arg His Arg Asn Arg Lys Gly Tyr Arg Ser Gln Arg Gly His Ser Arg
            355                 360                 365

Gly Arg Asn Gln Asn Ser Arg Arg Pro Ser Arg Gly Pro Glu Thr Leu
    370                 375                 380

Cys Gly Ala Glu Leu Val Asp Ala Leu Gln Phe Val Cys Gly Asp Arg
385                 390                 395                 400

Gly Phe Tyr Phe Asn Lys Pro Thr Gly Tyr Gly Ser Ser Ser Arg Arg
                405                 410                 415

Ala Pro Gln Thr Gly Ile Val Asp Glu Cys Cys Phe Arg Ser Cys Asp
            420                 425                 430

Leu Arg Arg Leu Glu Met Tyr Cys Ala Pro Leu Lys Pro Ala Lys Ser
            435                 440                 445

Ala

<210> SEQ ID NO 11
<211> LENGTH: 122
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (52)..(53)

<400> SEQUENCE: 11

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Gly Pro Glu Thr Leu Cys Gly Ala Glu Leu Val Asp
    50                  55                  60

Ala Leu Gln Phe Val Cys Gly Asp Arg Gly Phe Tyr Phe Asn Lys Pro
65                  70                  75                  80

Thr Gly Tyr Gly Ser Ser Ser Arg Arg Ala Pro Gln Thr Gly Ile Val
                85                  90                  95

Asp Glu Cys Cys Phe Arg Ser Cys Asp Leu Arg Arg Leu Glu Met Tyr
            100                 105                 110

Cys Ala Pro Leu Lys Pro Ala Lys Ser Ala
        115                 120

<210> SEQ ID NO 12
<211> LENGTH: 200
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (130)..(131)

<400> SEQUENCE: 12

Asp Gln Glu Ser Cys Lys Gly Arg Cys Thr Glu Gly Phe Asn Val Asp
1               5                   10                  15
```

```
Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
50                          55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Ala Pro Ala Pro Glu Val Gly Ala Ser Lys
                100                 105                 110

Pro Glu Gly Ile Asp Ser Arg Pro Glu Thr Leu His Pro Gly Arg Pro
            115                 120                 125

Gln Pro Gly Pro Glu Thr Leu Cys Gly Ala Glu Leu Val Asp Ala Leu
130                 135                 140

Gln Phe Val Cys Gly Asp Arg Gly Phe Tyr Phe Asn Lys Pro Thr Gly
145                 150                 155                 160

Tyr Gly Ser Ser Ser Arg Arg Ala Pro Gln Thr Gly Ile Val Asp Glu
                165                 170                 175

Cys Cys Phe Arg Ser Cys Asp Leu Arg Arg Leu Glu Met Tyr Cys Ala
                180                 185                 190

Pro Leu Lys Pro Ala Lys Ser Ala
            195                 200

<210> SEQ ID NO 13
<211> LENGTH: 373
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (303)..(304)

<400> SEQUENCE: 13

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Ala Pro Ala Pro Glu Val Gly Ala Ser Lys
                100                 105                 110

Pro Glu Gly Ile Asp Ser Arg Pro Glu Thr Leu His Pro Gly Arg Pro
            115                 120                 125

Gln Pro Ala Met Met Gln Arg Asp Ser Trp Glu Asp Ile Phe Glu Leu
130                 135                 140

Leu Phe Trp Gly Arg Thr Ser Ala Gly Thr Arg Gln Pro Gln Phe Ile
145                 150                 155                 160
```

-continued

Ser Arg Asp Trp His Gly Val Pro Gly Gln Val Asp Ala Ala Met Ala
                165                 170                 175

Gly Arg Ile Tyr Ile Ser Gly Met Ala Pro Arg Pro Ser Leu Ala Lys
            180                 185                 190

Lys Gln Arg Phe Arg His Arg Asn Arg Lys Gly Tyr Arg Ser Gln Arg
        195                 200                 205

Gly His Ser Arg Gly Arg Asn Gln Asn Ser Arg Pro Ser Arg Ala
    210                 215                 220

Thr Trp Leu Ser Leu Phe Ser Ser Glu Glu Ser Asn Leu Gly Ala Asn
225                 230                 235                 240

Asn Tyr Asp Asp Tyr Arg Met Asp Trp Leu Val Pro Ala Thr Cys Glu
                245                 250                 255

Pro Ile Gln Ser Val Phe Phe Phe Ser Gly Asp Lys Tyr Tyr Arg Val
            260                 265                 270

Asn Leu Arg Thr Arg Arg Val Asp Thr Val Asp Pro Pro Tyr Pro Arg
        275                 280                 285

Ser Ile Ala Gln Tyr Trp Leu Gly Cys Pro Ala Pro Gly His Leu Gly
    290                 295                 300

Pro Glu Thr Leu Cys Gly Ala Glu Leu Val Asp Ala Leu Gln Phe Val
305                 310                 315                 320

Cys Gly Asp Arg Gly Phe Tyr Phe Asn Lys Pro Thr Gly Tyr Gly Ser
                325                 330                 335

Ser Ser Arg Arg Ala Pro Gln Thr Gly Ile Val Asp Glu Cys Cys Phe
            340                 345                 350

Arg Ser Cys Asp Leu Arg Arg Leu Glu Met Tyr Cys Ala Pro Leu Lys
        355                 360                 365

Pro Ala Lys Ser Ala
    370

<210> SEQ ID NO 14
<211> LENGTH: 230
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (160)..(161)

<400> SEQUENCE: 14

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

```
Gln Pro Ala Met Met Gln Arg Asp Ser Trp Glu Asp Ile Phe Glu Leu
            130                 135                 140

Leu Phe Trp Gly Arg Thr Ser Ala Gly Thr Arg Gln Pro Gln Phe Ile
145                 150                 155                 160

Gly Pro Glu Thr Leu Cys Gly Ala Glu Leu Val Asp Ala Leu Gln Phe
                165                 170                 175

Val Cys Gly Asp Arg Gly Phe Tyr Phe Asn Lys Pro Thr Gly Tyr Gly
            180                 185                 190

Ser Ser Ser Arg Arg Ala Pro Gln Thr Gly Ile Val Asp Glu Cys Cys
        195                 200                 205

Phe Arg Ser Cys Asp Leu Arg Leu Glu Met Tyr Cys Ala Pro Leu
    210                 215                 220

Lys Pro Ala Lys Ser Ala
225                 230

<210> SEQ ID NO 15
<211> LENGTH: 417
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (347)..(348)

<400> SEQUENCE: 15

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
    210                 215                 220

Ser Asp Gly Phe Asp Gly Ile Pro Asp Asn Val Asp Ala Ala Leu Ala
225                 230                 235                 240
```

```
Leu Pro Ala His Ser Tyr Ser Gly Arg Glu Arg Val Tyr Phe Phe Lys
                245                 250                 255
Gly Lys Gln Tyr Trp Glu Tyr Gln Phe Gln His Gln Pro Ser Gln Glu
            260                 265                 270
Glu Cys Glu Gly Ser Ser Leu Ser Ala Val Phe Glu His Phe Ala Met
        275                 280                 285
Met Gln Arg Asp Ser Trp Glu Asp Ile Phe Glu Leu Leu Phe Trp Gly
    290                 295                 300
Arg Thr Ser Ala Gly Thr Arg Gln Pro Gln Phe Ile Ser Arg Asp Trp
305                 310                 315                 320
His Gly Val Pro Gly Gln Val Asp Ala Ala Met Ala Gly Arg Ile Tyr
                325                 330                 335
Ile Ser Gly Met Ala Pro Arg Pro Ser Leu Ala Gly Pro Glu Thr Leu
            340                 345                 350
Cys Gly Ala Glu Leu Val Asp Ala Leu Gln Phe Val Cys Gly Asp Arg
        355                 360                 365
Gly Phe Tyr Phe Asn Lys Pro Thr Gly Tyr Gly Ser Ser Arg Arg
    370                 375                 380
Ala Pro Gln Thr Gly Ile Val Asp Glu Cys Cys Phe Arg Ser Cys Asp
385                 390                 395                 400
Leu Arg Arg Leu Glu Met Tyr Cys Ala Pro Leu Lys Pro Ala Lys Ser
                405                 410                 415
Ala

<210> SEQ ID NO 16
<211> LENGTH: 529
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (459)..(460)

<400> SEQUENCE: 16

Asp Gln Glu Ser Cys Lys Gly Arg Cys Thr Glu Gly Phe Asn Val Asp
1               5                   10                  15
Lys Lys Cys Gln Cys Asp Glu Leu Cys Ser Tyr Tyr Gln Ser Cys Cys
            20                  25                  30
Thr Asp Tyr Thr Ala Glu Cys Lys Pro Gln Val Thr Arg Gly Asp Val
        35                  40                  45
Phe Ala Met Pro Glu Asp Glu Tyr Ala Val Tyr Asp Asp Gly Glu Glu
    50                  55                  60
Lys Asn Asn Ala Thr Val His Glu Gln Val Gly Gly Pro Ser Leu Thr
65                  70                  75                  80
Ser Asp Leu Gln Ala Gln Ser Lys Gly Asn Pro Glu Gln Thr Pro Val
                85                  90                  95
Leu Lys Pro Glu Glu Glu Ala Pro Ala Pro Glu Val Gly Ala Ser Lys
            100                 105                 110
Pro Glu Gly Ile Asp Ser Arg Pro Glu Thr Leu His Pro Gly Arg Pro
        115                 120                 125
Gln Pro Pro Ala Glu Glu Glu Leu Cys Ser Gly Lys Pro Phe Asp Ala
    130                 135                 140
Phe Thr Asp Leu Lys Asn Gly Ser Leu Phe Ala Phe Arg Gly Gln Tyr
145                 150                 155                 160
```

```
Cys Tyr Glu Leu Asp Glu Lys Ala Val Arg Pro Gly Tyr Pro Lys Leu
                165                 170                 175
Ile Arg Asp Val Trp Gly Ile Glu Gly Pro Ile Asp Ala Ala Phe Thr
            180                 185                 190
Arg Ile Asn Cys Gln Gly Lys Thr Tyr Leu Phe Lys Gly Ser Gln Tyr
        195                 200                 205
Trp Arg Phe Glu Asp Gly Val Leu Asp Pro Asp Tyr Pro Arg Asn Ile
    210                 215                 220
Ser Asp Gly Phe Asp Gly Ile Pro Asp Asn Val Asp Ala Ala Leu Ala
225                 230                 235                 240
Leu Pro Ala His Ser Tyr Ser Gly Arg Glu Arg Val Tyr Phe Phe Lys
                245                 250                 255
Gly Lys Gln Tyr Trp Glu Tyr Gln Phe Gln His Gln Pro Ser Gln Glu
            260                 265                 270
Glu Cys Glu Gly Ser Ser Leu Ser Ala Val Phe Glu His Phe Ala Met
        275                 280                 285
Met Gln Arg Asp Ser Trp Glu Asp Ile Phe Glu Leu Leu Phe Trp Gly
    290                 295                 300
Arg Thr Ser Ala Gly Thr Arg Gln Pro Gln Phe Ile Ser Arg Asp Trp
305                 310                 315                 320
His Gly Val Pro Gly Gln Val Asp Ala Ala Met Ala Gly Arg Ile Tyr
                325                 330                 335
Ile Ser Gly Met Ala Pro Arg Pro Ser Leu Ala Lys Lys Gln Arg Phe
            340                 345                 350
Arg His Arg Asn Arg Lys Gly Tyr Arg Ser Gln Arg Gly His Ser Arg
        355                 360                 365
Gly Arg Asn Gln Asn Ser Arg Arg Pro Ser Arg Ala Thr Trp Leu Ser
    370                 375                 380
Leu Phe Ser Ser Glu Glu Ser Asn Leu Gly Ala Asn Asn Tyr Asp Asp
385                 390                 395                 400
Tyr Arg Met Asp Trp Leu Val Pro Ala Thr Cys Glu Pro Ile Gln Ser
                405                 410                 415
Val Phe Phe Phe Ser Gly Asp Lys Tyr Tyr Arg Val Asn Leu Arg Thr
            420                 425                 430
Arg Arg Val Asp Thr Val Asp Pro Pro Tyr Pro Arg Ser Ile Ala Gln
        435                 440                 445
Tyr Trp Leu Gly Cys Pro Ala Pro Gly His Leu Gly Pro Glu Thr Leu
    450                 455                 460
Cys Gly Ala Glu Leu Val Asp Ala Leu Gln Phe Val Cys Gly Asp Arg
465                 470                 475                 480
Gly Phe Tyr Phe Asn Lys Pro Thr Gly Tyr Gly Ser Ser Ser Arg Arg
                485                 490                 495
Ala Pro Gln Thr Gly Ile Val Asp Glu Cys Cys Phe Arg Ser Cys Asp
            500                 505                 510
Leu Arg Arg Leu Glu Met Tyr Cys Ala Pro Leu Lys Pro Ala Lys Ser
        515                 520                 525
Ala

<210> SEQ ID NO 17
<211> LENGTH: 529
<212> TYPE: PRT
<213> ORGANISM: Artificial sequence
<220> FEATURE:
<223> OTHER INFORMATION: Synthetic chimera
<220> FEATURE:
```

```
<221> NAME/KEY: Linker
<222> LOCATION: (459)..(460)

<400> SEQUENCE: 17
```

| | | | | | | | | | | | | | | |
|---|---|---|---|---|---|---|---|---|---|---|---|---|---|---|
|Asp|Gln|Glu|Ser|Cys|Lys|Gly|Arg|Cys|Thr|Glu|Gly|Phe|Asn|Val|Asp
1| | | |5| | | | |10| | | | |15|

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Glu Met Pro Glu Asp Glu Tyr Glu Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
            85                  90                  95

Leu Lys Pro Glu Glu Ala Pro Ala Pro Glu Val Gly Ala Ser Lys
                100                 105                 110

Pro Glu Gly Ile Asp Ser Arg Pro Glu Thr Leu His Pro Gly Arg Pro
            115                 120                 125

Gln Pro Pro Ala Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
            165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
    210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
            245                 250                 255

Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
        275                 280                 285

Met Gln Arg Asp Ser Trp Glu Asp Ile Phe Glu Leu Leu Phe Trp Gly
    290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
            325                 330                 335

Ile Ser Gly Met Ala Pro Arg Pro Ser Leu Ala Lys Lys Gln Arg Phe
            340                 345                 350

Arg His Arg Asn Arg Lys Gly Tyr Arg Ser Gln Arg Gly His Ser Arg
        355                 360                 365

Gly Arg Asn Gln Asn Ser Arg Arg Pro Ser Arg Ala Thr Trp Leu Ser
    370                 375                 380

Leu Phe Ser Ser Glu Glu Ser Asn Leu Gly Ala Asn Asn Tyr Asp Asp
385                 390                 395                 400

```
Tyr Arg Met Asp Trp Leu Val Pro Ala Thr Cys Glu Pro Ile Gln Ser
            405                 410                 415

Val Phe Phe Phe Ser Gly Asp Lys Tyr Tyr Arg Val Asn Leu Arg Thr
        420                 425                 430

Arg Arg Val Asp Thr Val Asp Pro Pro Tyr Pro Arg Ser Ile Ala Gln
            435                 440                 445

Tyr Trp Leu Gly Cys Pro Ala Pro Gly His Leu Gly Pro Glu Thr Leu
        450                 455                 460

Cys Gly Ala Glu Leu Val Asp Ala Leu Gln Phe Val Cys Gly Asp Arg
465                 470                 475                 480

Gly Phe Tyr Phe Asn Lys Pro Thr Gly Tyr Gly Ser Ser Ser Arg Arg
                485                 490                 495

Ala Pro Gln Thr Gly Ile Val Asp Glu Cys Cys Phe Arg Ser Cys Asp
            500                 505                 510

Leu Arg Arg Leu Glu Met Tyr Cys Ala Pro Leu Lys Pro Ala Lys Ser
        515                 520                 525

Ala

<210> SEQ ID NO 18
<211> LENGTH: 529
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (459)..(460)

<400> SEQUENCE: 18

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205
```

```
Trp Arg Phe Glu Asp Gly Val Leu Asp Pro Asp Tyr Pro Arg Asn Ile
    210                 215                 220
Ser Asp Gly Phe Asp Gly Ile Pro Asp Asn Val Asp Ala Ala Leu Ala
225                 230                 235                 240
Leu Pro Ala His Ser Tyr Ser Gly Arg Glu Arg Val Tyr Phe Phe Lys
                245                 250                 255
Gly Lys Gln Tyr Trp Glu Tyr Gln Phe Gln His Gln Pro Ser Gln Glu
            260                 265                 270
Glu Cys Glu Gly Ser Ser Leu Ser Ala Val Phe Glu His Phe Ala Met
        275                 280                 285
Met Gln Arg Asp Ser Trp Glu Asp Ile Phe Glu Leu Leu Phe Trp Gly
    290                 295                 300
Arg Thr Ser Ala Gly Thr Arg Gln Pro Gln Phe Ile Ser Arg Asp Trp
305                 310                 315                 320
His Gly Val Pro Gly Gln Val Asp Ala Ala Met Ala Gly Arg Ile Tyr
                325                 330                 335
Ile Ser Gly Met Ala Pro Arg Pro Ser Leu Ala Lys Lys Gln Arg Phe
            340                 345                 350
Arg His Arg Asn Arg Lys Gly Tyr Arg Ser Gln Arg Gly His Ser Arg
        355                 360                 365
Gly Arg Asn Gln Asn Ser Arg Arg Pro Glu Arg Ala Thr Trp Leu Ser
    370                 375                 380
Leu Phe Ser Ser Glu Glu Ser Asn Leu Gly Ala Asn Asn Tyr Asp Asp
385                 390                 395                 400
Tyr Arg Met Asp Trp Leu Val Pro Ala Thr Cys Glu Pro Ile Gln Ser
                405                 410                 415
Val Phe Phe Phe Ser Gly Asp Lys Tyr Tyr Arg Val Asn Leu Arg Thr
            420                 425                 430
Arg Arg Val Asp Thr Val Asp Pro Pro Tyr Pro Arg Ser Ile Ala Gln
        435                 440                 445
Tyr Trp Leu Gly Cys Pro Ala Pro Gly His Leu Gly Pro Glu Thr Leu
    450                 455                 460
Cys Gly Ala Glu Leu Val Asp Ala Leu Gln Phe Val Cys Gly Asp Arg
465                 470                 475                 480
Gly Phe Tyr Phe Asn Lys Pro Thr Gly Tyr Gly Ser Ser Ser Arg Arg
                485                 490                 495
Ala Pro Gln Thr Gly Ile Val Asp Glu Cys Cys Phe Arg Ser Cys Asp
            500                 505                 510
Leu Arg Arg Leu Glu Met Tyr Cys Ala Pro Leu Lys Pro Ala Lys Ser
        515                 520                 525
Ala

<210> SEQ ID NO 19
<211> LENGTH: 529
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (459)..(460)

<400> SEQUENCE: 19

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
```

-continued

```
             20                  25                  30
Thr Asp Tyr Thr Ala Glu Cys Lys Pro Gln Val Thr Arg Gly Asp Val
             35                  40                  45

Phe Thr Met Pro Glu Asp Glu Tyr Thr Val Tyr Asp Asp Gly Glu Glu
             50                  55                  60

Lys Asn Asn Ala Thr Val His Glu Gln Val Gly Pro Ser Leu Thr
 65                  70                  75                  80

Ser Asp Leu Gln Ala Gln Ser Lys Gly Asn Pro Glu Gln Thr Pro Val
                     85                  90                  95

Leu Lys Pro Glu Glu Ala Pro Ala Pro Glu Val Gly Ala Ser Lys
                    100                 105                 110

Pro Glu Gly Ile Asp Ser Arg Pro Glu Thr Leu His Pro Gly Arg Pro
                    115                 120                 125

Gln Pro Pro Ala Glu Glu Leu Cys Ser Gly Lys Pro Phe Asp Ala
                    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                    165                 170                 175

Ile Arg Asp Val Trp Gly Ile Glu Gly Pro Ile Asp Ala Ala Phe Thr
                    180                 185                 190

Arg Ile Asn Cys Gln Gly Lys Thr Tyr Leu Phe Lys Gly Ser Gln Tyr
                    195                 200                 205

Trp Arg Phe Glu Asp Gly Val Leu Asp Pro Asp Tyr Pro Arg Asn Ile
                    210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                    245                 250                 255

Gly Lys Gln Tyr Trp Glu Tyr Gln Phe Gln His Gln Pro Ser Gln Glu
                    260                 265                 270

Glu Cys Glu Gly Ser Ser Leu Ser Ala Val Phe Glu His Phe Ala Met
                    275                 280                 285

Met Gln Arg Asp Ser Trp Glu Asp Ile Phe Glu Leu Leu Phe Trp Gly
                    290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                    325                 330                 335

Ile Ser Gly Met Ala Pro Arg Pro Ser Leu Ala Lys Lys Gln Arg Phe
                    340                 345                 350

Arg His Arg Asn Arg Lys Gly Tyr Arg Ser Gln Arg Gly His Ser Arg
                    355                 360                 365

Gly Arg Asn Gln Asn Ser Arg Arg Pro Ala Arg Ala Thr Trp Leu Ser
                    370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                    405                 410                 415

Val Phe Phe Phe Ser Gly Asp Lys Tyr Tyr Arg Val Asn Leu Arg Thr
                    420                 425                 430

Arg Arg Val Asp Thr Val Asp Pro Pro Tyr Pro Arg Ser Ile Ala Gln
                    435                 440                 445
```

```
Tyr Trp Leu Gly Cys Pro Ala Pro Gly His Leu Gly Pro Glu Thr Leu
    450                 455                 460

Cys Gly Ala Glu Leu Val Asp Ala Leu Gln Phe Val Cys Gly Asp Arg
465                 470                 475                 480

Gly Phe Tyr Phe Asn Lys Pro Thr Gly Tyr Gly Ser Ser Arg Arg
                485                 490                 495

Ala Pro Gln Thr Gly Ile Val Asp Glu Cys Cys Phe Arg Ser Cys Asp
                500                 505                 510

Leu Arg Arg Leu Glu Met Tyr Cys Ala Pro Leu Lys Pro Ala Lys Ser
            515                 520                 525

Ala

<210> SEQ ID NO 20
<211> LENGTH: 529
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (459)..(460)

<400> SEQUENCE: 20

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255
```

```
Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
        275                 280                 285

Met Gln Arg Asp Ser Trp Glu Asp Ile Phe Glu Leu Leu Phe Trp Gly
    290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                325                 330                 335

Ile Ser Gly Met Ala Pro Arg Pro Ser Leu Ala Lys Lys Gln Arg Phe
            340                 345                 350

Arg His Arg Asn Arg Lys Gly Tyr Arg Glu Gln Arg Gly His Ser Arg
        355                 360                 365

Gly Arg Asn Gln Asn Ser Arg Arg Pro Ser Arg Ala Thr Trp Leu Ser
    370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                405                 410                 415

Val Phe Phe Ser Gly Asp Lys Tyr Tyr Arg Val Asn Leu Arg Thr
            420                 425                 430

Arg Arg Val Asp Thr Val Asp Pro Pro Tyr Pro Arg Ser Ile Ala Gln
        435                 440                 445

Tyr Trp Leu Gly Cys Pro Ala Pro Gly His Leu Gly Pro Glu Thr Leu
    450                 455                 460

Cys Gly Ala Glu Leu Val Asp Ala Leu Gln Phe Val Cys Gly Asp Arg
465                 470                 475                 480

Gly Phe Tyr Phe Asn Lys Pro Thr Gly Tyr Gly Ser Ser Ser Arg Arg
                485                 490                 495

Ala Pro Gln Thr Gly Ile Val Asp Glu Cys Cys Phe Arg Ser Cys Asp
            500                 505                 510

Leu Arg Arg Leu Glu Met Tyr Cys Ala Pro Leu Lys Pro Ala Lys Ser
        515                 520                 525

Ala

<210> SEQ ID NO 21
<211> LENGTH: 526
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (459)..(460)

<400> SEQUENCE: 21

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
```

```
                65                  70                  75                  80
Ser Asp Leu Gln Ala Gln Ser Lys Gly Asn Pro Glu Gln Thr Pro Val
                        85                  90                  95
Leu Lys Pro Glu Glu Ala Pro Ala Pro Glu Val Gly Ala Ser Lys
                100                 105                 110
Pro Glu Gly Ile Asp Ser Arg Pro Glu Thr Leu His Pro Gly Arg Pro
                    115                 120                 125
Gln Pro Pro Ala Glu Glu Leu Cys Ser Gly Lys Pro Phe Asp Ala
145                 135                 140
Phe Thr Asp Leu Lys Asn Gly Ser Leu Phe Ala Phe Arg Gly Gln Tyr
145                 150                 155                 160
Cys Tyr Glu Leu Asp Glu Lys Ala Val Arg Pro Gly Tyr Pro Lys Leu
                    165                 170                 175
Ile Arg Asp Val Trp Gly Ile Glu Gly Pro Ile Asp Ala Ala Phe Thr
                180                 185                 190
Arg Ile Asn Cys Gln Gly Lys Thr Tyr Leu Phe Lys Gly Ser Gln Tyr
                    195                 200                 205
Trp Arg Phe Glu Asp Gly Val Leu Asp Pro Asp Tyr Pro Arg Asn Ile
210                 215                 220
Ser Asp Gly Phe Asp Gly Ile Pro Asp Asn Val Asp Ala Ala Leu Ala
225                 230                 235                 240
Leu Pro Ala His Ser Tyr Ser Gly Arg Glu Arg Val Tyr Phe Phe Lys
                    245                 250                 255
Gly Lys Gln Tyr Trp Glu Tyr Gln Phe Gln His Gln Pro Ser Gln Glu
                260                 265                 270
Glu Cys Glu Gly Ser Ser Leu Ser Ala Val Phe Glu His Phe Ala Met
                275                 280                 285
Met Gln Arg Asp Ser Trp Glu Asp Ile Phe Glu Leu Leu Phe Trp Gly
290                 295                 300
Arg Thr Ser Ala Gly Thr Arg Gln Pro Gln Phe Ile Ser Arg Asp Trp
305                 310                 315                 320
His Gly Val Pro Gly Gln Val Asp Ala Ala Met Ala Gly Arg Ile Tyr
                    325                 330                 335
Ile Ser Gly Met Ala Pro Arg Pro Ser Leu Ala Lys Lys Gln Arg Phe
                340                 345                 350
Arg His Arg Asn Arg Lys Gly Tyr Arg Ser Gln Arg Gly His Ser Arg
                355                 360                 365
Gly Arg Asn Gln Asn Ser Arg Arg Pro Ser Arg Ala Thr Trp Leu Ser
370                 375                 380
Leu Phe Ser Ser Glu Glu Ser Asn Leu Gly Ala Asn Asn Tyr Asp Asp
385                 390                 395                 400
Tyr Arg Met Asp Trp Leu Val Pro Ala Thr Cys Glu Pro Ile Gln Ser
                    405                 410                 415
Val Phe Phe Phe Ser Gly Asp Lys Tyr Tyr Arg Val Asn Leu Arg Thr
                420                 425                 430
Arg Arg Val Asp Thr Val Asp Pro Pro Tyr Pro Arg Ser Ile Ala Gln
                    435                 440                 445
Tyr Trp Leu Gly Cys Pro Ala Pro Gly His Leu Thr Leu Cys Gly Ala
                450                 455                 460
Glu Leu Val Asp Ala Leu Gln Phe Val Cys Gly Asp Arg Gly Phe Tyr
465                 470                 475                 480
Phe Asn Lys Pro Thr Gly Tyr Gly Ser Ser Arg Arg Ala Pro Gln
                    485                 490                 495
```

-continued

```
Thr Gly Ile Val Asp Glu Cys Cys Phe Arg Ser Cys Asp Leu Arg Arg
                500                 505                 510

Leu Glu Met Tyr Cys Ala Pro Leu Lys Pro Ala Lys Ser Ala
            515                 520                 525

<210> SEQ ID NO 22
<211> LENGTH: 517
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (447)..(448)

<400> SEQUENCE: 22

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Lys Asn Asn Ala Thr Val His Glu Gln Val Gly Gly
    50                  55                  60

Pro Ser Leu Thr Ser Asp Leu Gln Ala Gln Ser Lys Gly Asn Pro Glu
65                  70                  75                  80

Gln Thr Pro Val Leu Lys Pro Glu Glu Glu Ala Pro Ala Pro Glu Val
                85                  90                  95

Gly Ala Ser Lys Pro Glu Gly Ile Asp Ser Arg Pro Glu Thr Leu His
            100                 105                 110

Pro Gly Arg Pro Gln Pro Pro Ala Glu Glu Glu Leu Cys Ser Gly Lys
        115                 120                 125

Pro Phe Asp Ala Phe Thr Asp Leu Lys Asn Gly Ser Leu Phe Ala Phe
    130                 135                 140

Arg Gly Gln Tyr Cys Tyr Glu Leu Asp Glu Lys Ala Val Arg Pro Gly
145                 150                 155                 160

Tyr Pro Lys Leu Ile Arg Asp Val Trp Gly Ile Glu Gly Pro Ile Asp
                165                 170                 175

Ala Ala Phe Thr Arg Ile Asn Cys Gln Gly Lys Thr Tyr Leu Phe Lys
            180                 185                 190

Gly Ser Gln Tyr Trp Arg Phe Glu Asp Gly Val Leu Asp Pro Asp Tyr
        195                 200                 205

Pro Arg Asn Ile Ser Asp Gly Phe Asp Gly Ile Pro Asp Asn Val Asp
    210                 215                 220

Ala Ala Leu Ala Leu Pro Ala His Ser Tyr Ser Gly Arg Glu Arg Val
225                 230                 235                 240

Tyr Phe Phe Lys Gly Lys Gln Tyr Trp Glu Tyr Gln Phe Gln His Gln
                245                 250                 255

Pro Ser Gln Glu Glu Cys Glu Gly Ser Ser Leu Ser Ala Val Phe Glu
            260                 265                 270

His Phe Ala Met Met Gln Arg Asp Ser Trp Glu Asp Ile Phe Glu Leu
        275                 280                 285

Leu Phe Trp Gly Arg Thr Ser Ala Gly Thr Arg Gln Pro Gln Phe Ile
    290                 295                 300

Ser Arg Asp Trp His Gly Val Pro Gly Gln Val Asp Ala Ala Met Ala
305                 310                 315                 320
```

-continued

```
Gly Arg Ile Tyr Ile Ser Gly Met Ala Pro Arg Pro Ser Leu Ala Lys
                325                 330                 335

Lys Gln Arg Phe Arg His Arg Asn Arg Lys Gly Tyr Arg Ser Gln Arg
            340                 345                 350

Gly His Ser Arg Gly Arg Asn Gln Asn Ser Arg Arg Pro Ser Arg Ala
        355                 360                 365

Thr Trp Leu Ser Leu Phe Ser Ser Glu Glu Ser Asn Leu Gly Ala Asn
    370                 375                 380

Asn Tyr Asp Asp Tyr Arg Met Asp Trp Leu Val Pro Ala Thr Cys Glu
385                 390                 395                 400

Pro Ile Gln Ser Val Phe Phe Ser Gly Asp Lys Tyr Tyr Arg Val
                405                 410                 415

Asn Leu Arg Thr Arg Arg Val Asp Thr Val Asp Pro Pro Tyr Pro Arg
            420                 425                 430

Ser Ile Ala Gln Tyr Trp Leu Gly Cys Pro Ala Pro Gly His Leu Gly
        435                 440                 445

Pro Glu Thr Leu Cys Gly Ala Glu Leu Val Asp Ala Leu Gln Phe Val
    450                 455                 460

Cys Gly Asp Arg Gly Phe Tyr Phe Asn Lys Pro Thr Gly Tyr Gly Ser
465                 470                 475                 480

Ser Ser Arg Arg Ala Pro Gln Thr Gly Ile Val Asp Glu Cys Cys Phe
                485                 490                 495

Arg Ser Cys Asp Leu Arg Arg Leu Glu Met Tyr Cys Ala Pro Leu Lys
            500                 505                 510

Pro Ala Lys Ser Ala
        515

<210> SEQ ID NO 23
<211> LENGTH: 670
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (459)..(460)

<400> SEQUENCE: 23

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
    130                 135                 140
```

```
Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
            165                 170                 175

Ile Arg Asp Val Trp Gly Ile Glu Gly Pro Ile Asp Ala Ala Phe Thr
        180                 185                 190

Arg Ile Asn Cys Gln Gly Lys Thr Tyr Leu Phe Lys Gly Ser Gln Tyr
    195                 200                 205

Trp Arg Phe Glu Asp Gly Val Leu Asp Pro Asp Tyr Pro Arg Asn Ile
210                 215                 220

Ser Asp Gly Phe Asp Gly Ile Pro Asp Asn Val Asp Ala Ala Leu Ala
225                 230                 235                 240

Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
        275                 280                 285

Met Gln Arg Asp Ser Trp Glu Asp Ile Phe Glu Leu Leu Phe Trp Gly
    290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                325                 330                 335

Ile Ser Gly Met Ala Pro Arg Pro Ser Leu Ala Lys Lys Gln Arg Phe
            340                 345                 350

Arg His Arg Asn Arg Lys Gly Tyr Arg Ser Gln Arg Gly His Ser Arg
        355                 360                 365

Gly Arg Asn Gln Asn Ser Arg Arg Pro Ser Arg Ala Thr Trp Leu Ser
    370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                405                 410                 415

Val Phe Phe Phe Ser Gly Asp Lys Tyr Tyr Arg Val Asn Leu Arg Thr
            420                 425                 430

Arg Arg Val Asp Thr Val Asp Pro Pro Tyr Pro Arg Ser Ile Ala Gln
        435                 440                 445

Tyr Trp Leu Gly Cys Pro Ala Pro Gly His Leu Met Arg Thr Leu Ala
    450                 455                 460

Cys Leu Leu Leu Gly Cys Gly Tyr Leu Ala His Val Leu Ala Glu
465                 470                 475                 480

Glu Ala Glu Ile Pro Arg Glu Val Ile Glu Arg Leu Ala Arg Ser Gln
                485                 490                 495

Ile His Ser Ile Arg Asp Leu Gln Arg Leu Glu Ile Asp Ser Val
            500                 505                 510

Gly Ser Glu Asp Ser Leu Asp Thr Ser Leu Arg Ala His Gly Val His
        515                 520                 525

Ala Thr Lys His Val Pro Glu Lys Arg Pro Leu Pro Ile Arg Arg Lys
    530                 535                 540

Arg Ser Ile Glu Glu Ala Val Pro Ala Val Cys Lys Thr Arg Thr Val
545                 550                 555                 560
```

```
Ile Tyr Glu Ile Pro Arg Ser Gln Val Asp Pro Thr Ser Ala Asn Phe
                565                 570                 575

Leu Ile Trp Pro Pro Cys Val Glu Val Lys Arg Cys Thr Gly Cys Cys
            580                 585                 590

Asn Thr Ser Ser Val Lys Cys Gln Pro Ser Arg Val His His Arg Ser
            595                 600                 605

Val Lys Val Ala Lys Val Glu Tyr Val Arg Lys Lys Pro Lys Leu Lys
        610                 615                 620

Glu Val Gln Val Arg Leu Glu Glu His Leu Glu Cys Ala Cys Ala Thr
625                 630                 635                 640

Thr Ser Leu Asn Pro Asp Tyr Arg Glu Glu Asp Thr Gly Arg Pro Arg
                645                 650                 655

Glu Ser Gly Lys Lys Arg Lys Arg Lys Arg Leu Lys Pro Thr
            660                 665                 670

<210> SEQ ID NO 24
<211> LENGTH: 561
<212> TYPE: PRT
<213> ORGANISM: Artificial sequence
<220> FEATURE:
<223> OTHER INFORMATION: Synthetic chimera
<220> FEATURE:
<221> NAME/KEY: Linker
<222> LOCATION: (459)..(460)

<400> SEQUENCE: 24

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
    50                  55                  60

Lys Asn Asn Ala Thr Val His Glu Gln Val Gly Gly Pro Ser Leu Thr
65                  70                  75                  80

Ser Asp Leu Gln Ala Gln Ser Lys Gly Asn Pro Glu Gln Thr Pro Val
                85                  90                  95

Leu Lys Pro Glu Glu Glu Ala Pro Ala Pro Glu Val Gly Ala Ser Lys
            100                 105                 110

Pro Glu Gly Ile Asp Ser Arg Pro Glu Thr Leu His Pro Gly Arg Pro
        115                 120                 125

Gln Pro Pro Ala Glu Glu Glu Leu Cys Ser Gly Lys Pro Phe Asp Ala
    130                 135                 140

Phe Thr Asp Leu Lys Asn Gly Ser Leu Phe Ala Phe Arg Gly Gln Tyr
145                 150                 155                 160

Cys Tyr Glu Leu Asp Glu Lys Ala Val Arg Pro Gly Tyr Pro Lys Leu
                165                 170                 175

Ile Arg Asp Val Trp Gly Ile Glu Gly Pro Ile Asp Ala Ala Phe Thr
            180                 185                 190

Arg Ile Asn Cys Gln Gly Lys Thr Tyr Leu Phe Lys Gly Ser Gln Tyr
        195                 200                 205

Trp Arg Phe Glu Asp Gly Val Leu Asp Pro Asp Tyr Pro Arg Asn Ile
    210                 215                 220

Ser Asp Gly Phe Asp Gly Ile Pro Asp Asn Val Asp Ala Ala Leu Ala
225                 230                 235                 240
```

```
Leu Pro Ala His Ser Tyr Ser Gly Arg Glu Arg Val Tyr Phe Phe Lys
                245                 250                 255

Gly Lys Gln Tyr Trp Glu Tyr Gln Phe Gln His Gln Pro Ser Gln Glu
            260                 265                 270

Glu Cys Glu Gly Ser Ser Leu Ser Ala Val Phe Glu His Phe Ala Met
            275                 280                 285

Met Gln Arg Asp Ser Trp Glu Asp Ile Phe Glu Leu Leu Phe Trp Gly
            290                 295                 300

Arg Thr Ser Ala Gly Thr Arg Gln Pro Gln Phe Ile Ser Arg Asp Trp
305                 310                 315                 320

His Gly Val Pro Gly Gln Val Asp Ala Ala Met Ala Gly Arg Ile Tyr
                325                 330                 335

Ile Ser Gly Met Ala Pro Arg Pro Ser Leu Ala Lys Lys Gln Arg Phe
            340                 345                 350

Arg His Arg Asn Arg Lys Gly Tyr Arg Ser Gln Arg Gly His Ser Arg
            355                 360                 365

Gly Arg Asn Gln Asn Ser Arg Arg Pro Ser Arg Ala Thr Trp Leu Ser
            370                 375                 380

Leu Phe Ser Ser Glu Glu Ser Asn Leu Gly Ala Asn Asn Tyr Asp Asp
385                 390                 395                 400

Tyr Arg Met Asp Trp Leu Val Pro Ala Thr Cys Glu Pro Ile Gln Ser
                405                 410                 415

Val Phe Phe Phe Ser Gly Asp Lys Tyr Tyr Arg Val Asn Leu Arg Thr
            420                 425                 430

Arg Arg Val Asp Thr Val Asp Pro Pro Tyr Pro Arg Ser Ile Ala Gln
            435                 440                 445

Tyr Trp Leu Gly Cys Pro Ala Pro Gly His Leu Gly Gln Asn His His
            450                 455                 460

Glu Val Val Lys Phe Met Asp Val Tyr Gln Arg Ser Tyr Cys His Pro
465                 470                 475                 480

Ile Glu Thr Leu Val Asp Ile Phe Gln Glu Tyr Pro Asp Glu Ile Glu
                485                 490                 495

Tyr Ile Phe Lys Pro Ser Cys Val Pro Leu Met Arg Cys Gly Gly Cys
            500                 505                 510

Cys Asn Asp Glu Gly Leu Glu Cys Val Pro Thr Glu Glu Ser Asn Ile
            515                 520                 525

Thr Met Gln Ile Met Arg Ile Lys Pro His Gln Gly Gln His Ile Gly
            530                 535                 540

Glu Met Ser Phe Leu Gln His Asn Lys Cys Glu Cys Arg Pro Lys Lys
545                 550                 555                 560

Asp

<210> SEQ ID NO 25
<211> LENGTH: 2386
<212> TYPE: PRT
<213> ORGANISM: Homo sapiens

<400> SEQUENCE: 25

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
            35                  40                  45
```

```
Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
             100                 105                 110

Glu Arg Pro Lys Asp Ser Met Ile Trp Asp Cys Thr Cys Ile Gly Ala
         115                 120                 125

Gly Arg Gly Arg Ile Ser Cys Thr Ile Ala Asn Arg Cys His Glu Gly
     130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                 165                 170                 175

Trp Thr Cys Lys Pro Ile Ala Glu Lys Cys Phe Asp His Ala Ala Gly
             180                 185                 190

Thr Ser Tyr Val Val Gly Glu Thr Trp Glu Lys Pro Tyr Gln Gly Trp
         195                 200                 205

Met Met Val Asp Cys Thr Cys Leu Gly Glu Gly Ser Gly Arg Ile Thr
     210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                 245                 250                 255

Gln Cys Ile Cys Thr Gly Asn Gly Arg Gly Glu Trp Lys Cys Glu Arg
             260                 265                 270

His Thr Ser Val Gln Thr Thr Ser Ser Gly Ser Gly Pro Phe Thr Asp
         275                 280                 285

Val Arg Ala Ala Val Tyr Gln Pro Gln Pro His Pro Gln Pro Pro
     290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                 325                 330                 335

Gly Asn Gly Val Ser Cys Gln Glu Thr Ala Val Thr Gln Thr Tyr Gly
             340                 345                 350

Gly Asn Ser Asn Gly Glu Pro Cys Val Leu Pro Phe Thr Tyr Asn Gly
         355                 360                 365

Arg Thr Phe Tyr Ser Cys Thr Thr Glu Gly Arg Gln Asp Gly His Leu
     370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
                 405                 410                 415

Gly Ala Leu Cys His Phe Pro Phe Leu Tyr Asn Asn His Asn Tyr Thr
             420                 425                 430

Asp Cys Thr Ser Glu Gly Arg Arg Asp Asn Met Lys Trp Cys Gly Thr
         435                 440                 445

Thr Gln Asn Tyr Asp Ala Asp Gln Lys Phe Gly Phe Cys Pro Met Ala
     450                 455                 460

Ala His Glu Glu Ile Cys Thr Thr Asn Glu Gly Val Met Tyr Arg Ile
```

```
            465                 470                 475                 480
        Gly Asp Gln Trp Asp Lys Gln His Asp Met Gly His Met Met Arg Cys
                            485                 490                 495
        Thr Cys Val Gly Asn Gly Arg Gly Glu Trp Thr Cys Ile Ala Tyr Ser
                        500                 505                 510
        Gln Leu Arg Asp Gln Cys Ile Val Asp Asp Ile Thr Tyr Asn Val Asn
                    515                 520                 525
        Asp Thr Phe His Lys Arg His Glu Gly His Met Leu Asn Cys Thr
                530                 535                 540
        Cys Phe Gly Gln Gly Arg Gly Arg Trp Lys Cys Asp Pro Val Asp Gln
        545                 550                 555                 560
        Cys Gln Asp Ser Glu Thr Gly Thr Phe Tyr Gln Ile Gly Asp Ser Trp
                        565                 570                 575
        Glu Lys Tyr Val His Gly Val Arg Tyr Gln Cys Tyr Cys Tyr Gly Arg
                    580                 585                 590
        Gly Ile Gly Glu Trp His Cys Gln Pro Leu Gln Thr Tyr Pro Ser Ser
                595                 600                 605
        Ser Gly Pro Val Glu Val Phe Ile Thr Glu Thr Pro Ser Gln Pro Asn
            610                 615                 620
        Ser His Pro Ile Gln Trp Asn Ala Pro Gln Pro Ser His Ile Ser Lys
        625                 630                 635                 640
        Tyr Ile Leu Arg Trp Arg Pro Lys Asn Ser Val Gly Arg Trp Lys Glu
                        645                 650                 655
        Ala Thr Ile Pro Gly His Leu Asn Ser Tyr Thr Ile Lys Gly Leu Lys
                    660                 665                 670
        Pro Gly Val Val Tyr Glu Gly Gln Leu Ile Ser Ile Gln Gln Tyr Gly
                675                 680                 685
        His Gln Glu Val Thr Arg Phe Asp Phe Thr Thr Thr Ser Thr Ser Thr
            690                 695                 700
        Pro Val Thr Ser Asn Thr Val Thr Gly Glu Thr Thr Pro Phe Ser Pro
        705                 710                 715                 720
        Leu Val Ala Thr Ser Glu Ser Val Thr Glu Ile Thr Ala Ser Ser Phe
                        725                 730                 735
        Val Val Ser Trp Val Ser Ala Ser Asp Thr Val Ser Gly Phe Arg Val
                    740                 745                 750
        Glu Tyr Glu Leu Ser Glu Glu Gly Asp Glu Pro Gln Tyr Leu Asp Leu
                755                 760                 765
        Pro Ser Thr Ala Thr Ser Val Asn Ile Pro Asp Leu Leu Pro Gly Arg
        770                 775                 780
        Lys Tyr Ile Val Asn Val Tyr Gln Ile Ser Glu Asp Gly Glu Gln Ser
        785                 790                 795                 800
        Leu Ile Leu Ser Thr Ser Gln Thr Thr Ala Pro Asp Ala Pro Pro Asp
                        805                 810                 815
        Pro Thr Val Asp Gln Val Asp Asp Thr Ser Ile Val Val Arg Trp Ser
                    820                 825                 830
        Arg Pro Gln Ala Pro Ile Thr Gly Tyr Arg Ile Val Tyr Ser Pro Ser
                835                 840                 845
        Val Glu Gly Ser Ser Thr Glu Leu Asn Leu Pro Glu Thr Ala Asn Ser
            850                 855                 860
        Val Thr Leu Ser Asp Leu Gln Pro Gly Val Gln Tyr Asn Ile Thr Ile
        865                 870                 875                 880
        Tyr Ala Val Glu Glu Asn Gln Glu Ser Thr Pro Val Val Ile Gln Gln
                        885                 890                 895
```

-continued

```
Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro  Thr Asn Leu Gln Phe Val Asn Glu
        995                 1000                1005

Thr Asp Ser Thr Val Leu Val Arg Trp Thr Pro Pro Arg Ala Gln
    1010            1015            1020

Ile Thr Gly Tyr Arg Leu Thr Val Gly Leu Thr Arg Arg Gly Gln
    1025            1030            1035

Pro Arg Gln Tyr Asn Val Gly Pro Ser Val Ser Lys Tyr Pro Leu
    1040            1045            1050

Arg Asn Leu Gln Pro Ala Ser Glu Tyr Thr Val Ser Leu Val Ala
    1055            1060            1065

Ile Lys Gly Asn Gln Glu Ser Pro Lys Ala Thr Gly Val Phe Thr
    1070            1075            1080

Thr Leu Gln Pro Gly Ser Ser Ile Pro Pro Tyr Asn Thr Glu Val
    1085            1090            1095

Thr Glu Thr Thr Ile Val Ile Thr Trp Thr Pro Ala Pro Arg Ile
    1100            1105            1110

Gly Phe Lys Leu Gly Val Arg Pro Ser Gln Gly Gly Glu Ala Pro
    1115            1120            1125

Arg Glu Val Thr Ser Asp Ser Gly Ser Ile Val Val Ser Gly Leu
    1130            1135            1140

Thr Pro Gly Val Glu Tyr Val Tyr Thr Ile Gln Val Leu Arg Asp
    1145            1150            1155

Gly Gln Glu Arg Asp Ala Pro Ile Val Asn Lys Val Val Thr Pro
    1160            1165            1170

Leu Ser Pro Pro Thr Asn Leu His Leu Glu Ala Asn Pro Asp Thr
    1175            1180            1185

Gly Val Leu Thr Val Ser Trp Glu Arg Ser Thr Thr Pro Asp Ile
    1190            1195            1200

Thr Gly Tyr Arg Ile Thr Thr Thr Pro Thr Asn Gly Gln Gln Gly
    1205            1210            1215

Asn Ser Leu Glu Glu Val Val His Ala Asp Gln Ser Ser Cys Thr
    1220            1225            1230

Phe Asp Asn Leu Ser Pro Gly Leu Glu Tyr Asn Val Ser Val Tyr
    1235            1240            1245

Thr Val Lys Asp Asp Lys Glu Ser Val Pro Ile Ser Asp Thr Ile
    1250            1255            1260

Ile Pro Ala Val Pro Pro Thr Asp Leu Arg Phe Thr Asn Ile
    1265            1270            1275

Gly Pro Asp Thr Met Arg Val Thr Trp Ala Pro Pro Ser Ile
    1280            1285            1290
```

```
Asp Leu Thr Asn Phe Leu Val Arg Tyr Ser Pro Val Lys Asn Glu
    1295                1300                1305

Glu Asp Val Ala Glu Leu Ser Ile Ser Pro Ser Asp Asn Ala Val
    1310                1315                1320

Val Leu Thr Asn Leu Leu Pro Gly Thr Glu Tyr Val Val Ser Val
    1325                1330                1335

Ser Ser Val Tyr Glu Gln His Glu Ser Thr Pro Leu Arg Gly Arg
    1340                1345                1350

Gln Lys Thr Gly Leu Asp Ser Pro Thr Gly Ile Asp Phe Ser Asp
    1355                1360                1365

Ile Thr Ala Asn Ser Phe Thr Val His Trp Ile Ala Pro Arg Ala
    1370                1375                1380

Thr Ile Thr Gly Tyr Arg Ile Arg His His Pro Glu His Phe Ser
    1385                1390                1395

Gly Arg Pro Arg Glu Asp Arg Val Pro His Ser Arg Asn Ser Ile
    1400                1405                1410

Thr Leu Thr Asn Leu Thr Pro Gly Thr Glu Tyr Val Val Ser Ile
    1415                1420                1425

Val Ala Leu Asn Gly Arg Glu Glu Ser Pro Leu Leu Ile Gly Gln
    1430                1435                1440

Gln Ser Thr Val Ser Asp Val Pro Arg Asp Leu Glu Val Val Ala
    1445                1450                1455

Ala Thr Pro Thr Ser Leu Leu Ile Ser Trp Asp Ala Pro Ala Val
    1460                1465                1470

Thr Val Arg Tyr Tyr Arg Ile Thr Tyr Gly Glu Thr Gly Gly Asn
    1475                1480                1485

Ser Pro Val Gln Glu Phe Thr Val Pro Gly Ser Lys Ser Thr Ala
    1490                1495                1500

Thr Ile Ser Gly Leu Lys Pro Gly Val Asp Tyr Thr Ile Thr Val
    1505                1510                1515

Tyr Ala Val Thr Gly Arg Gly Asp Ser Pro Ala Ser Ser Lys Pro
    1520                1525                1530

Ile Ser Ile Asn Tyr Arg Thr Glu Ile Asp Lys Pro Ser Gln Met
    1535                1540                1545

Gln Val Thr Asp Val Gln Asp Asn Ser Ile Ser Val Lys Trp Leu
    1550                1555                1560

Pro Ser Ser Ser Pro Val Thr Gly Tyr Arg Val Thr Thr Thr Pro
    1565                1570                1575

Lys Asn Gly Pro Gly Pro Thr Lys Thr Lys Thr Ala Gly Pro Asp
    1580                1585                1590

Gln Thr Glu Met Thr Ile Glu Gly Leu Gln Pro Thr Val Glu Tyr
    1595                1600                1605

Val Val Ser Val Tyr Ala Gln Asn Pro Ser Gly Glu Ser Gln Pro
    1610                1615                1620

Leu Val Gln Thr Ala Val Thr Asn Ile Asp Arg Pro Lys Gly Leu
    1625                1630                1635

Ala Phe Thr Asp Val Asp Val Asp Ser Ile Lys Ile Ala Trp Glu
    1640                1645                1650

Ser Pro Gln Gly Gln Val Ser Arg Tyr Arg Val Thr Tyr Ser Ser
    1655                1660                1665

Pro Glu Asp Gly Ile His Glu Leu Phe Pro Ala Pro Asp Gly Glu
    1670                1675                1680

Glu Asp Thr Ala Glu Leu Gln Gly Leu Arg Pro Gly Ser Glu Tyr
```

```
                1685                1690                1695

Thr Val Ser Val Val Ala Leu His Asp Asp Met Glu Ser Gln Pro
    1700                1705                1710

Leu Ile Gly Thr Gln Ser Thr Ala Ile Pro Ala Pro Thr Asp Leu
    1715                1720                1725

Lys Phe Thr Gln Val Thr Pro Thr Ser Leu Ser Ala Gln Trp Thr
    1730                1735                1740

Pro Pro Asn Val Gln Leu Thr Gly Tyr Arg Val Arg Val Thr Pro
    1745                1750                1755

Lys Glu Lys Thr Gly Pro Met Lys Glu Ile Asn Leu Ala Pro Asp
    1760                1765                1770

Ser Ser Ser Val Val Ser Gly Leu Met Val Ala Thr Lys Tyr
    1775                1780                1785

Glu Val Ser Val Tyr Ala Leu Lys Asp Thr Leu Thr Ser Arg Pro
    1790                1795                1800

Ala Gln Gly Val Val Thr Thr Leu Glu Asn Val Ser Pro Pro Arg
    1805                1810                1815

Arg Ala Arg Val Thr Asp Ala Thr Glu Thr Thr Ile Thr Ile Ser
    1820                1825                1830

Trp Arg Thr Lys Thr Glu Thr Ile Thr Gly Phe Gln Val Asp Ala
    1835                1840                1845

Val Pro Ala Asn Gly Gln Thr Pro Ile Gln Arg Thr Ile Lys Pro
    1850                1855                1860

Asp Val Arg Ser Tyr Thr Ile Thr Gly Leu Gln Pro Gly Thr Asp
    1865                1870                1875

Tyr Lys Ile Tyr Leu Tyr Thr Leu Asn Asp Asn Ala Arg Ser Ser
    1880                1885                1890

Pro Val Val Ile Asp Ala Ser Thr Ala Ile Asp Ala Pro Ser Asn
    1895                1900                1905

Leu Arg Phe Leu Ala Thr Thr Pro Asn Ser Leu Leu Val Ser Trp
    1910                1915                1920

Gln Pro Pro Arg Ala Arg Ile Thr Gly Tyr Ile Ile Lys Tyr Glu
    1925                1930                1935

Lys Pro Gly Ser Pro Pro Arg Glu Val Val Pro Arg Pro Arg Pro
    1940                1945                1950

Gly Val Thr Glu Ala Thr Ile Thr Gly Leu Glu Pro Gly Thr Glu
    1955                1960                1965

Tyr Thr Ile Tyr Val Ile Ala Leu Lys Asn Asn Gln Lys Ser Glu
    1970                1975                1980

Pro Leu Ile Gly Arg Lys Lys Thr Asp Glu Leu Pro Gln Leu Val
    1985                1990                1995

Thr Leu Pro His Pro Asn Leu His Gly Pro Glu Ile Leu Asp Val
    2000                2005                2010

Pro Ser Thr Val Gln Lys Thr Pro Phe Val Thr His Pro Gly Tyr
    2015                2020                2025

Asp Thr Gly Asn Gly Ile Gln Leu Pro Gly Thr Ser Gly Gln Gln
    2030                2035                2040

Pro Ser Val Gly Gln Gln Met Ile Phe Glu Glu His Gly Phe Arg
    2045                2050                2055

Arg Thr Thr Pro Pro Thr Thr Ala Thr Pro Ile Arg His Arg Pro
    2060                2065                2070

Arg Pro Tyr Pro Pro Asn Val Gly Glu Glu Ile Gln Ile Gly His
    2075                2080                2085
```

Ile Pro Arg Glu Asp Val Asp Tyr His Leu Tyr Pro His Gly Pro
    2090             2095                 2100

Gly Leu Asn Pro Asn Ala Ser Thr Gly Gln Glu Ala Leu Ser Gln
    2105             2110                 2115

Thr Thr Ile Ser Trp Ala Pro Phe Gln Asp Thr Ser Glu Tyr Ile
    2120             2125                 2130

Ile Ser Cys His Pro Val Gly Thr Asp Glu Glu Pro Leu Gln Phe
    2135             2140                 2145

Arg Val Pro Gly Thr Ser Thr Ser Ala Thr Leu Thr Gly Leu Thr
    2150             2155                 2160

Arg Gly Ala Thr Tyr Asn Ile Ile Val Glu Ala Leu Lys Asp Gln
    2165             2170                 2175

Gln Arg His Lys Val Arg Glu Val Val Thr Val Gly Asn Ser
    2180             2185                 2190

Val Asn Glu Gly Leu Asn Gln Pro Thr Asp Asp Ser Cys Phe Asp
    2195             2200                 2205

Pro Tyr Thr Val Ser His Tyr Ala Val Gly Asp Glu Trp Glu Arg
    2210             2215                 2220

Met Ser Glu Ser Gly Phe Lys Leu Leu Cys Gln Cys Leu Gly Phe
    2225             2230                 2235

Gly Ser Gly His Phe Arg Cys Asp Ser Ser Arg Trp Cys His Asp
    2240             2245                 2250

Asn Gly Val Asn Tyr Lys Ile Gly Glu Lys Trp Asp Arg Gln Gly
    2255             2260                 2265

Glu Asn Gly Gln Met Met Ser Cys Thr Cys Leu Gly Asn Gly Lys
    2270             2275                 2280

Gly Glu Phe Lys Cys Asp Pro His Glu Ala Thr Cys Tyr Asp Asp
    2285             2290                 2295

Gly Lys Thr Tyr His Val Gly Glu Gln Trp Gln Lys Glu Tyr Leu
    2300             2305                 2310

Gly Ala Ile Cys Ser Cys Thr Cys Phe Gly Gly Gln Arg Gly Trp
    2315             2320                 2325

Arg Cys Asp Asn Cys Arg Arg Pro Gly Gly Glu Pro Ser Pro Glu
    2330             2335                 2340

Gly Thr Thr Gly Gln Ser Tyr Asn Gln Tyr Ser Gln Arg Tyr His
    2345             2350                 2355

Gln Arg Thr Asn Thr Asn Val Asn Cys Pro Ile Glu Cys Phe Met
    2360             2365                 2370

Pro Leu Asp Val Gln Ala Asp Arg Glu Asp Ser Arg Glu
    2375             2380                 2385

<210> SEQ ID NO 26
<211> LENGTH: 20
<212> TYPE: PRT
<213> ORGANISM: Artificial Sequence
<220> FEATURE:
<223> OTHER INFORMATION: Synthetic linker

<400> SEQUENCE: 26

Gly Gly Gly Gly Ser Gly Gly Gly Gly Ser Gly Gly Gly Gly Ser Gly
1               5                   10                  15

Gly Gly Gly Ser
            20

<210> SEQ ID NO 27

<211> LENGTH: 152
<212> TYPE: PRT
<213> ORGANISM: Artificial Sequence
<220> FEATURE:
<223> OTHER INFORMATION: Synthetic chimera

<400> SEQUENCE: 27

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
50                  55                  60

Gly Gly Gly Gly Ser Gly Gly Gly Ser Gly Gly Gly Ser Gly
65                  70                  75                  80

Gly Gly Gly Ser Asn Ser Asp Ser Glu Cys Pro Leu Ser His Asp Gly
                85                  90                  95

Tyr Cys Leu His Asp Gly Val Cys Met Tyr Ile Glu Ala Leu Asp Lys
            100                 105                 110

Tyr Ala Cys Asn Cys Val Val Gly Tyr Ile Gly Glu Arg Cys Gln Tyr
        115                 120                 125

Arg Asp Leu Lys Trp Trp Glu Leu Arg Gly Gly Gly Ser Gly Gly
    130                 135                 140

Gly Gly His His His His His His
145                 150
```

<210> SEQ ID NO 28
<211> LENGTH: 245
<212> TYPE: PRT
<213> ORGANISM: Artificial Sequence
<220> FEATURE:
<223> OTHER INFORMATION: Synthetic chimera

<400> SEQUENCE: 28

```
Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
            20                  25                  30

Thr Asp Tyr Thr Ala Glu Cys Lys Pro Gln Val Thr Arg Gly Asp Val
        35                  40                  45

Phe Thr Met Pro Glu Asp Glu Tyr Thr Val Tyr Asp Asp Gly Glu Glu
50                  55                  60

Gly Gly Gly Gly Ser Gly Gly Gly Ser Gly Gly Gly Ser Gly
65                  70                  75                  80

Gly Gly Gly Ser Pro Ala Leu Pro Glu Asp Gly Gly Ser Gly Ala Phe
                85                  90                  95

Pro Pro Gly His Phe Lys Asp Pro Lys Arg Leu Tyr Cys Lys Asn Gly
            100                 105                 110

Gly Phe Phe Leu Arg Ile His Pro Asp Gly Arg Val Asp Gly Val Arg
        115                 120                 125

Glu Lys Ser Asp Pro His Ile Lys Leu Gln Leu Gln Ala Glu Glu Arg
    130                 135                 140

Gly Val Val Ser Ile Lys Gly Val Cys Ala Asn Arg Tyr Leu Ala Met
145                 150                 155                 160

Lys Glu Asp Gly Arg Leu Leu Ala Ser Lys Cys Val Thr Asp Glu Cys
```

```
                165                 170                 175
Phe Phe Phe Glu Arg Leu Glu Ser Asn Asn Tyr Asn Thr Tyr Arg Ser
            180                 185                 190

Arg Lys Tyr Thr Ser Trp Tyr Val Ala Leu Lys Arg Thr Gly Gln Tyr
            195                 200                 205

Lys Leu Gly Ser Lys Thr Gly Pro Gly Gln Lys Ala Ile Leu Phe Leu
            210                 215                 220

Pro Met Ser Ala Lys Ser Gly Gly Gly Ser Gly Gly Gly His
225                 230                 235                 240

His His His His His
                245

<210> SEQ ID NO 29
<211> LENGTH: 262
<212> TYPE: PRT
<213> ORGANISM: Artificial Sequence
<220> FEATURE:
<223> OTHER INFORMATION: Synthetic chimera

<400> SEQUENCE: 29

Asp Gln Glu Ser Cys Lys Gly Arg Cys Thr Glu Gly Phe Asn Val Asp
1               5                   10                  15

Lys Lys Cys Gln Cys Asp Glu Leu Cys Ser Tyr Tyr Gln Ser Cys Cys
                20                  25                  30

Thr Asp Tyr Thr Ala Glu Cys Lys Pro Gln Val Thr Arg Gly Asp Val
            35                  40                  45

Phe Thr Met Pro Glu Asp Glu Tyr Thr Val Tyr Asp Asp Gly Glu Glu
        50                  55                  60

Gly Gly Gly Gly Ser Gly Gly Gly Ser Gly Gly Gly Ser Gly
65                  70                  75                  80

Gly Gly Ser Cys Asn Asp Met Thr Pro Glu Gln Met Ala Thr Asn
                85                  90                  95

Val Asn Cys Ser Ser Pro Glu Arg His Thr Arg Ser Tyr Asp Tyr Met
            100                 105                 110

Glu Gly Gly Asp Ile Arg Val Arg Arg Leu Phe Cys Arg Thr Gln Trp
        115                 120                 125

Tyr Leu Arg Ile Asp Lys Arg Gly Lys Val Lys Gly Thr Gln Glu Met
    130                 135                 140

Lys Asn Asn Tyr Asn Ile Met Glu Ile Arg Thr Val Ala Val Gly Ile
145                 150                 155                 160

Val Ala Ile Lys Gly Val Glu Ser Glu Phe Tyr Leu Ala Met Asn Lys
                165                 170                 175

Glu Gly Lys Leu Tyr Ala Lys Lys Glu Cys Asn Glu Asp Cys Asn Phe
            180                 185                 190

Lys Glu Leu Ile Leu Glu Asn His Tyr Asn Thr Tyr Ala Ser Ala Lys
        195                 200                 205

Trp Thr His Asn Gly Gly Glu Met Phe Val Ala Leu Asn Gln Lys Gly
    210                 215                 220

Ile Pro Val Arg Gly Lys Lys Thr Lys Lys Glu Gln Lys Thr Ala His
225                 230                 235                 240

Phe Leu Pro Met Ala Ile Thr Gly Gly Gly Gly Ser Gly Gly Gly Gly
                245                 250                 255

His His His His His His
            260
```